United States Patent
Hayama et al.

(10) Patent No.: US 6,413,979 B1
(45) Date of Patent: Jul. 2, 2002

(54) SUBSTITUTED 5-(2,2-DIFLUORO-1,3-BENZODIOXOL-5-YL) CYCLOPENTENOPYRIDINE DERIVATIVE

(75) Inventors: Takashi Hayama; Norikazu Otake; Masaru Nishikibe, all of Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/582,225

(22) PCT Filed: Jan. 18, 1999

(86) PCT No.: PCT/JP99/00131

§ 371 (c)(1), (2), (4) Date: Jul. 21, 2000

(87) PCT Pub. No.: WO99/37639

PCT Pub. Date: Jul. 29, 1999

(30) Foreign Application Priority Data

Jan. 21, 1998 (JP) ................................. 10-23979

(51) Int. Cl.[7] ..................... A61F 31/435; C07D 405/04; C07D 405/14
(52) U.S. Cl. ..................... 514/299; 546/112; 546/283.4; 546/283.7
(58) Field of Search ............................. 546/112, 283.7, 546/283.4; 514/299

(56) References Cited

U.S. PATENT DOCUMENTS

| | | | |
|---|---|---|---|
| 5,389,620 A | 2/1995 | Ishikawa et al. | 514/80 |
| 5,714,479 A | 2/1998 | Ishikawa et al. | 514/80 |
| 5,834,483 A | 11/1998 | Lynch, Jr. et al. | 514/299 |
| 6,087,360 A | 7/2000 | Lynch, Jr. et al. | 514/248 |

*Primary Examiner*—Charanjit S. Aulakh
(74) *Attorney, Agent, or Firm*—Oblon, Spivak, McClelland, Maier & Neustadt, P.C.

(57) ABSTRACT

The present invention relates to a cyclopentenopyridine derivative represented by general formula (I) or a pharmaceutically acceptable salt thereof, wherein Ar is a phenyl group or the like. $R^1$ is a mono- or di-$C_1$–$C_6$ alkylamino group or the like, and $R^2$ is a hydroxyl group or the like, a process for its production and its use.

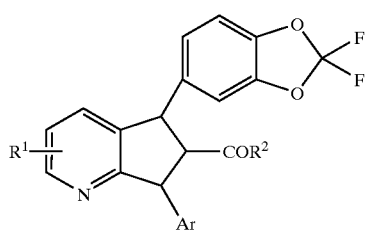

70 Claims, No Drawings

SUBSTITUTED 5-(2,2-DIFLUORO-1,3-BENZODIOXOL-5-YL) CYCLOPENTENOPYRIDINE DERIVATIVE

This application is a 371 of PCT/JP99/00131 filed Jan. 18, 1999.

TECHNICAL FIELD

The present invention relates to novel compounds having antagonism against three kinds of endothelin (endothelin-1, endothelin-2 and endothelin-3), which are physiologically highly active endogenous peptides in the field of medicines, processes for their preparation and their use as a drug.

BACKGROUND ART

Endothelin is a polypeptide compound of 21 amino acids, and it is produced by endothelial cells of human and pig. Endothelin has a potent vasoconstrictor effect and a sustained and potent pressor action (Nature, 32, 411–415 (1988)). Three endothelin family peptides (endothelin-1, endothelin-2 and endothelin-3), which resemble one another in structure, exist in the bodies of animals including human, and these peptides are known to have vasoconstriction and pressor effects (Proc. Natl. Acad. Sci. USA, 86, 2863–2867 (1989)).

It is clinically reported that the endothelin levels are clearly elevated in the blood of patients with essential hypertension, acute myocardial infarction, pulmonary hypertension, Raynaud's disease, diabetes or atherosclerosis, or in the washing fluids from the respiratory tract or the blood of asthmatics as compared with normal levels (Japan. J. Hypertension, 12, 79, (1989), J. Vascular Medicine Biology, 2, 207 (1990), Diabetologia, 33, 306–310 (1990), J. Am. Med. Association, 264, 2868 (1990), and The Lances, ii, 747–748 (1989) and ii, 1144–1147 (1990)).

Further, an increased sensitivity of the cerebral blood vessel to endothelin in an experimental model of cerebral vasospasm (Japan. Soc. Cereb. Blood Flow & Metabol., 1, 73 (1989)), an improved renal function by an endothelin antibody in an acute renal failure model (J. Clin. Invest., 83, 1762–1767 (1989), and inhibition of gastric ulcer development with an endothelin antibody in a gastric ulcer model (Extract of the 19th Meeting of Japanese Society of Experimental Gastric Ulcer, 50 (1991)) have been reported. Therefore, endothelin is assumed to be one of the mediators causing acute renal failure or cerebral vasospasm following subarachnoid hemorrhage.

Further, it is revealed that endothelin is secreted not only by vascular endothelial cells but also by tracheal epithelial cells and kidney cells (FEBS Letters, 249, 42–46 (1989), and ibid., 255, 129–132 (1989)).

Endothelin was also found to control the release of physiologically active endogenous peptides such as renin and atrial natriuretic hormone, and other physiologically active substances such as endothelium-derived relaxing factor (EDRF), thromboxane A2, prostacyclin, noradrenaline, angiotensin II and substance P (Biochem. Biophys. Res. Commun., 157, 1164–1168 (1988); ibid., 155, 167–172 (1989); Proc. Natl. Acad. SCi. USA, 85, 9797–9800 (1989); J. Cardiovasc. Pharmacol., 13, S89–S92 (1989); Japan. J. Hypertension, 12, 76 (1989) and Neuroscience Letters, 102, 179–184 (1989)). Further, endothelin causes contraction of the smooth muscle of the gastrointestinal tract and the uterine smooth muscle (FEBS Letters, 247, 337–340 (1989); Eur. J. Pharmacol., 154, 227–228 (1988); and Biochem. Biophys. Res. Commun., 159, 317–323 (1989)).

Further, endothelin was found to promote proliferation of rat vascular smooth muscle cells, suggesting a possible relevance to arterial hypertrophy (Atherosclerosis, 78, 225–228 (1989)). Furthermore, since it is known that the endothelin receptors are present in a high density not only in the peripheral tissues but also in the central nervous system, and cerebral administration of endothelin induces a behavioral change in animals, endothelin is likely to play an important role in controlling nervous functions (Neuroscience Letters, 97, 276–279 (1989)). Particularly, endothelin is suggested as one of the mediators for pain (Life Science, 49, PL61–PL65 (1989))

Further, endothelin is reported to appreciably promote endarterial hypertrophy induced by injury to rat coronary arterial endothelial cells by ballooning (J. Cardiovasc. Pharmacol., 22, 355–359 (1993)). Thus, it is suggested that endothelin is likely to be involved in restenosis following percutaneous transluminal angioplasty.

In recent years, it has been revealed that the human prostate has endothelin receptors A and B and shows a potent vasoconstrictor effect of endothelin (J. Urology, 151, 763–766 (1994); and Molecular Pharmacology, 45, 306–311 (1994)), which indicates that endothelin is involved in pathology of prostatism as one of the important factors.

On the other hand, endotoxin is one of the potential candidates to promote the release of endothelin. Remarkable elevation of the endothelin levels in the blood or in the supernatant of cultured endothelial cells was observed when endotoxin was exogenously administered to animals or added to the cultured endothelial cells, respectively. These findings suggest that endothelin is one of the important mediators for endotoxin-induced diseases (Biochem. Biophys. Res. Commun., 161, 1220 (1989); and Acta Physiol. Scand., 137, 317–318 (1989)).

Further, it was reported that cyclosporin remarkably increased endothelin secretion in a renal cell culture (LLC-PKI cells) (Eur. J. Pharmacol., 180, 191–192 (1990)). Further, cyclosporin-induced renal failure can be suppressed by the administration of endothelin antibody (Kidney Int., 37, 1487–1491 (1990)). Thus, it is assumed that endothelin is significantly involved in the pathogenesis of the cyclosporin-induced diseases. Such various effects of endothelin are caused by the binding of endothelin to endothelin receptors widely distributed in many tissues (Am. J. Physiol., 256, R856–R866 (1989)).

It is known that vasoconstriction by the endothelins is caused via at least two subtypes of endothelin receptors (J. Cardiovasc. Pharmacol., 17(Suppl.7), S119–S121 (1993)). One of the endothelin receptors is $ET_A$ receptor selective to ET-1 rather than ET-3, and the other is $ET_B$ receptor equally active to ET-1 and ET-3. These receptor proteins are reported to be different from each other (Nature, 348, 730–735 (1990)).

These two subtypes of endothelin receptors, which are different in selectivity to endothelin family peptides, are differently distributed in tissues. It is known that the $ET_A$ receptor is present mainly in the cardiovascular tissues, whereas the $ET_B$ receptor is widely distributed in various tissues such as the brain, the lung, the kidney, the heart and the vascular tissues.

In summary, endothelin is an endogenous substance which directly or indirectly (by controlling liberation of various endogenous substances) induces sustained contraction or relaxation of vascular or non-vascular smooth muscles, and its excessive production or excessive secretion is believed to be one of the pathogeneses for hypertension, pulmonary hypertension, Raynaud's disease, bronchial asthma, gastric ulcer, diabetes, arteriosclerosis, acute renal failure, heart failure, myocardial infarction, angina pectoris, cerebral infarction and cerebral vasospasm. Further, it is suggested that endothelin serves as an important mediator involved in diseases such as restenosis, prostatism, endotoxin shock, endotoxin-induced multiple organ failure or disseminated intravascular coagulation, and/or cyclosporin-induced renal failure or hypertension. Two endothelin receptors $ET_A$ and $ET_B$ are known so far. Not only an antagonist against both the $ET_A$ and $ET_B$ receptors but also a selective antagonist against the $ET_A$ receptor is promising as a drug.

The prior art representing general technical standards in this field includes, for example, EP526708A1 and WO93088799A1, which already disclose some peptidic compounds antagonistic to endothelin receptors.

The closest prior art includes WO9505374A1. WO9505374A1 discloses condensed aromatic heterocyclic cyclopentene derivatives having as Ar, a phenyl group having various substituents inclusive of a methylenedioxyphenyl group, but not a 2,2-difluoro-1,3-benzodioxole group.

While the compounds disclosed in WO9505374A1 are mostly antagonists against both the $ET_A$ and $ET_B$ receptors, the compounds of the present invention, which are structurally different only in the presence of two fluorine atoms on a 1,3-benzodioxole group as substituents, are selective antagonists against the $ET_A$ receptor.

Antagonists against endothelin receptors are classified as antagonistic to both the $ET_A$ and $ET_B$ receptors, selectively antagonistic to the $ET_A$ receptor or selectively antagonistic to the $ET_B$ receptor. Among them, antagonists against both the $ET_A$ and $ET_B$ receptors and selective antagonists against the $ET_A$ receptor competitively inhibit various physiological effects of endothelin and thus are promising as drugs in a wide variety of fields, as described above.

However, because endothelin acts differently from tissue to tissue via either the $ET_A$ or $ET_B$ receptor or via both of them, as described above, some experiments on animals have suggested that these two kinds of antagonists have different effects on several diseases (J. Cardiovasc. Pharmacol., 26, S322–S325 (1995); Br. J. Pharmacol., 112, 207–213 (1994) and ibid., 120, 319–325 (1997)).

Therefore, it is demanded that not only antagonists against both the $ET_A$ and $ET_B$ receptors but also non-peptidic compounds selectively antagonistic to the $ET_A$ receptor only are invented.

DISCLOSURE OF THE INVENTION

The present inventors have synthesized various cyclopentenopyridine derivatives having a 2,2-difluoro-1,3-benzodioxole group and have investigated their endothelin antagonistic activities. As a result, they have found that cyclopentenopyridine derivatives represented by general formula (I) and their pharmaceutically acceptable salts:

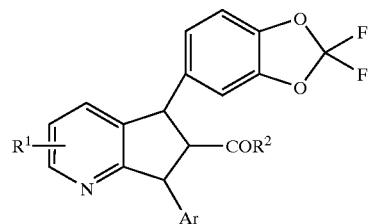

wherein Ar is a phenyl group, a thienyl group or a pyridyl group which may have one to three substituents selected from the group consisting of hydroxyl groups, amino groups, carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups, $R^1$ is a hydrogen atom, a hydroxyl group, a cyano group, a nitro group, a carboxyl group, an amino group, a halogen atom, a $C_1$–$C_6$ alkyl group, a $C_3$–$C_8$ cycloalkyl group, a $C_3$–$C_8$ cycloalkyl $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkylthio group, a formyl group, a $C_2$–$C_6$ alkanoyl group, an aroyl group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl)amino group, a $C_2$–$C_6$ alkanoylamino group, an aroylamino group, an N—($C_1$–$C_6$ alkyl)-N-(aroyl)amino group, a $C_1$–$C_6$ alkylsulfonylamino group, an aryl $C_1$–$C_6$ alkylamino group, an N-(aryl $C_1$–$C_6$ alkyl)-N-(aroyl)amino group, an arylsulfonylamino group, an aryl $C_1$–$C_6$ alkylsulfonylamino group, a $C_4$–$C_7$ cyclic imino group or a $C_1$–$C_6$ alkoxycarbonyl group, and $R^2$ is a hydroxyl group, an amino group, a $C_1$–$C_6$ alkoxy group, a mono- or di-$C_1$–$C_6$ alkylamino group, a $C_1$–$C_6$ alkylsulfonylamino group or an arylsulfonylamino or an aryl $C_1$–$C_6$ alkylsulfonylamino group which may have a $C_1$–$C_6$ alkyl group, have selective potent $ET_A$ receptor antagonistic activities. The present invention has been accomplished on the basis of this discovery. The invention of the novel cyclopentenopyridine derivatives provides novel treatments of the after-mentioned various diseases.

Now, the meanings of various abbreviations used in this specification will be given in Table 1.

TABLE 1

| Abbreviation | Meaning of abbreviation |
| --- | --- |
| Et | Ethyl |
| Me | Methyl |
| nPr | n-Propyl |
| iPr | Isopropyl |
| nBu | n-Butyl |
| tert-Bu | tert-Butyl |
| Ph | Phenyl |
| Bzl | Benzyl |
| c-Pent | Cyclopentyl |
| CDI | 1,1-Carbonyldiimidazole |
| DCC | N,N-Dicyclohexylcarbodiimide |
| DMAP | 4-(Dimethylamino)pyridine |
| DMF | N,N-Dimethylformamide |
| DMSO | Dimethyl sulfoxide |
| HMPA | Hexamethylphosphoric triamide |
| mCPBA | m-Chloroperbenzoic acid |
| NMM | N-Methylmorpholine |

TABLE 1-continued

| Abbreviation | Meaning of abbreviation |
| --- | --- |
| EDCHCl | 1-Ethyl-3-(3-dimethylaminopropyl)carbodiimide hydrochloride |
| TEA | Triethylamine |
| TFA | Trifluoroacetic acid |
| THF | Tetrahydrofuran |
| TsOH | p-Toluenesulfonic acid |
| HEPES | 2-[4-(2-Hydroxyethyl)-1-piperazinyl]ethanesulfonic acid |
| Tris | Tris(hydroxymethyl) aminomethane |

Now, the definitions of the various terms mentioned in this specification will be explained.

The halogen atom means fluorine, chlorine, bromine and iodine.

The $C_1$–$C_6$ alkyl group means a straight or branched alkyl group having 1 to 6 carbon atoms such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a 1-methylbutyl group, a 2-methylbutyl group, a 1,2-dimethylpropyl group, a 1-ethylbutyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1-ethylbutyl group, a 1,1,2-trimethylpropyl group, a 1,2,2-trimethylpropyl group, a 1-ethyl-1-methylpropyl group or a 1-ethyl-2-methylpropyl group. Among them, preferred is, for example, a methyl group, an ethyl group, a propyl group, a butyl group, an isobutyl group, a sec-butyl group or a pentyl group. Particularly preferred is, for example, a methyl group, an ethyl group, a propyl group or an isobutyl group.

The $C_3$–$C_8$ cycloalkyl group means a cycloalkyl group having 3 to 8 carbon atoms such as a cyclopropyl group, a cyclobutyl group, a cyclopentyl group, a cyclohexyl group, a cycloheptyl group, a cyclooctyl group, a 2-methylcyclopropyl group, a 1-methylcyclobutyl group, a 2-methylcyclopentyl group or a 2,2-dimethylcycloheyyl group. Among them, preferred is a cyclopropyl group, a cyclobutyl group, a cyclopentyl group or a cyclohexyl group. Particularly preferred is a cyclopentyl group or a cyclohexyl group.

The $C_2$–$C_6$ alkenyl group means a straight or branched alkenyl group having 2 to 6 carbon atoms such as a vinyl group, an allyl group, a 1-propenyl group, an isopropenyl group, a 3-butenyl group, a 2-butenyl group, a 1-butenyl group, a 1-methyl-2-propenyl group, a 1-methyl-1-propenyl group, a 1-ethyl-1-ethenyl group, a 2-methyl-2-propenyl group, a 2-methyl-1-propenyl group or a 4-pentenyl group. Among them, a vinyl group, an allyl group, a 1-propenyl group, a 3-butenyl group or a 1-methyl-1-propenyl group. Particularly preferred is a vinyl group, an allyl group or a 1-propenyl group.

The $C_2$–$C_6$ alkynyl group means a straight or branched alkynyl group having 2 to 6 carbon atoms such as an ethynyl group, a 1-propynyl group, a 2-propynyl group, a 1-butynyl group, a 2-butynyl group, a 3-butynyl group, a 1-methyl-2-propynyl group or a 1-pentynyl group. Among them, preferred is an ethynyl group, a 1-propynyl group, 2-propynyl group or a 2-butynyl group. Particularly preferred is a 1-propynyl group or a 2-propynyl group.

The $C_1$–$C_6$ alkoxy group means a straight or branched alkoxy group having 1 to 6 carbon atoms such as a methoxy group, an ethoxy group, a propoxy group, an isopropovy group, a butoxy group, an isobutoxy group, a sec-butoxy group, a tert-butoxy group, a pentyloxy group or a hexyloxy group. Among them, preferred is a methoxy group, an ethoxy group, a propoxy group or an isopropoxy group. Particularly preferred is a methoxy group or an ethoxy group.

The $C_1$–$C_6$ alkoxycarbonyl group means a carbonyl group having the above $C_1$–$C_6$ alkoxy group such as a methoxycarbonyl group, an ethoxycarbonyl group, a propoxycarbonyl group, an isopropoxycarbonyl group, a butyloxycarbonyl group, an isobutyloxycarbonyl group, a tert-butyloxycarbonyl group, a pentyloxycarbonyl group, an isopentyloxycarbonyl group or a hexyloxycarbonyl group. Among them, preferred is a methoxycarbonyl group, an ethoxycarbonyl group, a propoxycarbonyl group or a butyloxycarbonyl group. Particularly preferred is a methoxycarbonyl group or an ethoxycarbonyl group.

The mono- or di-$C_1$–$C_6$ alkylamino group means an amino group having one or two above-mentioned $C_1$–$C_6$ alkyl groups on the nitrogen atom such as a methylamino group, an ethylamino group, a propylamino group, an isopropylamino group, a butylamino group, an isobutylamino group, a tert-butylamino group, a pentylamino group, an isopentylamino group, a hexylamino group, a dimethylamino group, an ethylmethylamino group, a diethylamino group, an isopropylmethylamino group, a dipropylamino group, an ethylisopropylamino group, a diisopropylamino group, a dibutylamino group, a diisobutylamino group, a di-tert-butylamino group, a dipentylamino group, an ethylpentylamino group, a diisopentylamino group, an ethylhexylamino group or a dihexylamino group. Among them, preferred is a methylamino group, an ethylamino group, a propylamino group, an isopropylamino group, a butylamino group or a tert-butylamino group. Particularly preferred is an ethylamino group, a propylamino group, an isopropylamino group or a tert-butylamino group.

The mono- or di-$C_1$–$C_6$ alkylaminocarbonyl group means a carbonyl group having the above-mentioned mono- or di-$C_1$–$C_6$ alkylamino group such as a methylaminocarbonyl group, an ethylaminocarbonyl group, a propylaminocarbonyl group, an isopropylaminocarbonyl group, a butylaminocarbonyl group, an isobutylaminocarbonyl group, a tert-butylaminocarbonyl group, a pentylaminocarbonyl group, an isopentylaminocarbonyl group, a hexylaminocarbonyl group, a dimethylaminocarbonyl group, an ethylmethylaminocarbonyl group, a diethylaminocarbonyl group, an isopropylmethylaminocarbonyl group, a dipropylaminocarbonyl group, an ethylisopropylaminocarbonyl group, a diisopropylaminocarbonyl group, a dibutylaminocarbonyl group, a diisobutylaminocarbonyl group, a di-tert-butylaminocarbonyl group, a dipentylaminocarbonyl group, an ethylpentylaminocarbonyl group, a diisopentylaminocarbonyl group or an ethylhexylaminocarbonyl group. Among them, preferred is a methylaminocarbonyl group, an ethylaminocarbonyl group, a dimethylaminocarbonyl group, an ethylmethylaminocarbonyl group or a diethylaminocarbonyl group. Particularly preferred is a methylaminocarbonyl group or a dimethylaminocarbonyl group.

The $C_1$–$C_6$ alkylthio group means a straight or branched alkylthio group having 1 to 6 carbon atoms such as a methylthio group, an ethylthio group, a propylthio group, an isopropylthio group, a butylthio group, an isobutylthio group a sec-isobutylthio group, a tert-butylthio group, a pentylthio group or a hexylthio group. Among them, preferred is a methylthio group, an ethylthio group, a propylthio group, an isopropylthio group or a butylthio group. Particularly preferred is a methylthio group, an ethylthio group or a propylthio group.

The $C_2$–$C_6$ alkanoyl group means a straight or branched alkanoyl group having 2 to 6 carbon atoms such as an acetyl group, a propanoyl group, a butyryl group, an isobutyryl group, an isopropanoyl group, a pentanoyl group or a hexanoyl group. Among them, preferred is an acetyl group, a propanoyl group, a butyryl group, an isobutyryl group or a pentanoyl group. Particularly preferred is an acetyl group, a propanoyl group or a butyryl group.

The aryl group means an aromatic carbocyclic group having 6 to 14 carbon atoms or an aromatic heterocyclic group containing 1 to 4 hetero atoms selected from nitrogen atoms and sulfur atoms such as a phenyl group, a naphthyl group, a pyridyl group or a furyl group. Among them, preferred is a phenyl group, a naphthyl group or a pyridyl group. Particularly preferred is a phenyl group or a pyridyl group.

The aroyl group means an aroyl group having an aromatic mono- to tri-cyclic carbocyclic ring or an aromatic mono- to tri-cyclic heterocyclic ring containing 1 to 4 hetero atoms selected from the group consisting of nitrogen atoms and sulfur atoms such as a benzoyl group, a naphthoyl group, a pyridylcarbonyl group, a thienylcarbonyl group, a furylcarbonyl group, a thiazolylcarbonyl group, an oxazolylcarbonyl group, imidazolylcarbonyl group or a quinolylcarbonyl group. Among them, preferred is a benzoyl group, a naphthoyl group, a pyridylcarbonyl group or a thienylcarbonyl group. Particularly preferred is a benzoyl group or a pyridylcarbonyl group.

The $C_3$–$C_8$ cycloalkylamino group means an amino group having the above-mentioned $C_3$–$C_8$ cycloalkyl group such as a cyclopropylamino group, a cyclobutylamino group, a cyclopentylamino group, a cyclohexylamino group, a cycloheptylamino group, a cyclooctylamino group, a 2-methylcyclopropylamino group, a 1-methylcyclobutylamino group, a 2-methylcyclopentylamino group or a 2,2-dimethylcyclohexylamino group. Among them, preferred is a cyclopropylamino group, a cyclobutylamino group, a cyclopentylamino group or a cyclohexylamino group. Particularly preferred is a cyclobutylamino group or a cyclopentylamino group.

The $C_3$–$C_6$ cycloalkyl $C_1$–$C_6$ alkylamino group means the above-mentioned $C_1$–$C_6$ alkylamino group having a cycloalkyl group having 3 to 8 carbon atoms on the alkyl moiety such as a cyclopropylmethylamino group, a cyclobutylmethylamino group, a cyclopentylmethylamino group, a cyclohexylmethylamino group, a 1-cyclopropylethylamino group, a 2-cyclopropylethylamino group or a 3-cyclopropylpropylamino group. Among them, preferred is a cyclobutylmethylamino group, a cyclopentylmethylamino group or a cyclohexylmethylamino group. Particularly preferred is a cyclobutylmethylamino group or a cyclopentylmethylamino group.

The N—($C_1$–$C_6$ alkyl)-N—($C_3$–$C_8$ cycloalkyl)amino group means an N—($C_1$–$C_6$ alkyl)-N—($C_3$–$C_8$ cycloalkyl) amino group having 4 to 15 carbon atoms such as an N-methyl-N-cyclopropylamino group, an N-methyl-N-cyclobutylamino group, an N-methyl-N-cyclopentylamino group, an N-methyl-N-cyclohexylamino group, an N-methyl-N-cycloheptylamino group, an N-methyl-N-cyclooctylamino group, an N-ethyl-N-cyclopropylamino group, an N-butyl-N-cyclopropylamino group, an N-pentyl-N-cyclopropylamino group, an N-hexyl-N-cyclopropylamino group, an N-ethyl-N-cyclobutylamino group, an N-ethyl-N-cyclopentylamino group, an N-propyl-N-cyclobutylamino group or an N-pentyl-N-cyclopentylamino group. Among them, preferred is an N-methyl-N-cyclobutylamino group, an N-methyl-N-cyclopentylamino group or an N-methyl-N-cyclohexylamino group. Particularly preferred is an N-methyl-N-cyclobutylamino group or an N-methyl-N-cyclopentylamino group.

The $C_2$–$C_6$ alkanoylamino group means an amino group having the above-mentioned $C_2$–$C_6$ alkanoyl group such as an acetylamino group, a propanoylamino group, an isopropanoylamino group, a butanoylamino group, a 2-methylpropanoylamino group, a 2,2-dimethylpropanoylamino group, a pentanoylamino group, a 2-methylbutanoylamino group, a hexanoylamino group or a 2-methylpentanoylamino group. Among them, preferred is an acetylamino group, a propanoylamino group, an isopropanoylamino group or a butanoylamino group. Particularly preferred is an acetylamino group or a propanoylamino group.

The aroylamino group means an amino group having the above-mentioned aroyl group such as a benzoylamino group, a naphthoylamino group, a pyridylcarbonylamino group, a thienylcarbonylamino group, a furylcarbonylamino group, a thiazolylcarbonylamino group, an oxazolylcarbonylamino group or a quinolylcarbonylamino group. Among them, preferred is a benzoylamino group, a naphthoylamino group, a pyridylcarbonylamino group or a thienylcarbonylamino group. Particularly preferred is a benzoylamino group or a pyridylcarbonylamino group.

The N—($C_1$–$C_6$ alkyl)-N-(aroyl)amino group means an amino group having the above-mentioned $C_1$–$C_6$ alkyl and aroyl groups on the nitrogen atom and 6 to 12 carbon atoms such as an N-methyl-N-benzoylamino group, an N-(1-ethyl)-N-benzoylamino group, an N-(1-butyl)-N-benzoylamino group, an N-(1-pentyl)-N-benzoylamino group, an N-(2-ethyl)-N-benzoylamino group, an N-(2-propyl)-N-benzoylamino group, an N-(3-butyl)-N-benzoylamino group, an N-(4-pentyl)-N-benzoylamino group, an N-methyl-N-naphthoylamino group, an N-methyl-N-thienylcarbonylamino group, an N-methyl-N-furylcarbonylamino group, an N-methyl-N-pyridylcarbonylamino group or an N-methyl-N-imidazoylcarbonylamino group. Among them, preferred is an N-methyl-N-benzoylamino group, an N-methyl-N-naphthoylamino group or an N-methyl-N-thienylcarbonylamino group. Particularly preferred is an N-methyl-N-benzoylamino group or an N-methyl-N-naphthoylamino group.

The $C_1$–$C_6$ alkylsulfonylamino group means a sulfonylamino group having the above-mentioned $C_1$–$C_6$ alkyl group such as a methylsulfonylamino group, an ethylsulfonylamino group, a propylsulfonylamino group, an isopropylsulfonylamino group, a butylsulfonylamino group, an isobutylsulfonylamino group, a tert-butylsulfonylamino group, a pentylsulfonylamino group, an isopentylsulfonylamino group or a hexylsulfonylamino group. Among them, preferred is a methylsulfonylamino group, an ethylsulfonylamino group, a propylsulfonylamino group or an isopropylsulfonylamino group. Particularly preferred is a methylsulfonylamino group or an ethylsulfonylamino group.

The $C_1$–$C_6$ alkylsulfonylaminocarbonyl group means a carbonyl group having the above-mentioned $C_1$–$C_6$ alkylsulfonylamino group such as a methylsulfonylaminocarbonyl group, an ethylsulfonylaminocarbonyl group, a propylsulfonylaminocarbonyl group, an isopropylsulfonylaminocarbonyl group, a butylsulfonylaminocarbonyl group, an isobutylsulfonylaminocarbonyl group, a tert-butylsulfonylaminocarbonyl group, a pentylsulfonylaminocarbonyl group, an isopentylsulfonylaminocarbonyl group or a hexylsulfonylaminocarbonyl group. Among them, preferred is a methylsulfonylaminocarbonyl group, an ethylsulfonylaminocarbonyl group or a propylsulfonylaminocarbonyl group. Particularly preferred is a methylsulfonylaminocarbonyl group or an ethylsulfonylaminocarbonyl group.

The aryl $C_1$–$C_6$ alkylamino group means the above-mentioned $C_1$–$C_6$ alkylamino group having the above-mentioned aryl group on the alkyl moiety such as a benzylamino group, a phenylethylamino group, a phenylpropylamino group, a 1-methyl-2-phenylethylamino group, a phenylbutylamino group, a phenylpentylamino group, a phenylhexylamino group, a naphthylmethylamino group, a naphthylethylamino group, a naphthylpropylamino group, a thienylmethylamino group, a pyridylmethylamino group, a furylmethylamino group, a thienylethylamino group, a pyridylethylamino group, a furylethylamino group, a thienylpropylamino group, a pyridylbutylamino group, a furylpentylamino group or a thienylhexylamino group. Among them, preferred is a benzylamino group, a phenylethylamino group, a phenylpropylamino group or a phenylbutylamino group. Particularly preferred is a benzylamino group or a phenylethylamino group.

The N-(aryl $C_1$–$C_6$ alkyl)-N-(aroyl)amino group means an N-(aryl $C_1$–$C_6$ alkyl)-N-(aroyl)amino group which comprises the above-mentioned aryl $C_1$–$C_6$ alkylamino group and the above-mentioned aroyl group on the nitrogen atom and has 14 to 20 carbon atoms such as an N-benzyl-N-benzoylamino group, an N-(1-phenylethyl)-N-benzoylamino group, an N-(1-phenylpropyl)-N-benzoylamino group, an N-(1-phenylbutyl)-N-benzoylamino group, an N-(1-phenylpentyl)-N-benzoylamino group, an N-methyl-N-naphthoylamino group, an N-methyl-N-thienylcarbonylamino group, an N-benzyl-N-furylcarbonylamino group, an N-benzyl-N-pyridylcarbonylamino group or an N-benzyl-N-imidazoylcarbonylamino group. Among them, preferred is an N-benzyl-N-benzoylamino group, an N-(1-phenylethyl)-N-benzoylamino group or an N-(1-phenyloropyl)-N-benzoylamino group. Particularly preferred is an N-benzyl-N-benzoylamino group.

The arylsulfonylamino group means a sulfonylamino group having the above-mentioned aryl group such as a phenylsulfonylamino group, a naphthylsulfonylamino group, a pyridylsulfonylamino group or a furylsulfonylamino group. Among them, preferred is a phenylsulfonylamino group, a naphthylsulfonylamino group or a pyridylsulfonylamino group. Particularly preferred is a phenylsulfonylamino group or a pyridylsulfonylamino group.

The aryl $C_1$–$C_6$ alkylsulfonylamino group means an arylalkylsulfonylamino group comprising the above-mentioned $C_1$–$C_6$ alkylsulfonylamino group and the above-mentioned aryl group on the alkyl moiety such as a benzylsulfonylamino group, a phenylethylsulfonylamino group, a phenylpropylsulfonylamino group, a 1-methyl-2-phenylethylsulfonylamino group, a phenylbutylsulfonylamino group, a phenylpentylsulfonylamino group, a phenylhexylsulfonylamino group, a naphthylmethylsulfonylamino group, a naphthylethylsulfonylamino group, a naphthylpropylsulfonylamino group, a thienylmethylsulfonylamino group, a pyridylmethylsulfonylamino group, a furylmethylsulfonylamino group, a thienylethylsulfonylamino group, a pyridylethylsulfonylamino group, a furylethylsulfonylamino group, a thienylpropylsulfonylamino group, a pyridylbutylsulfonylamino group, a furylpentylsulfonylamino group or a thienylhexylsulfonylamino group. Among them, preferred is a benzylsulfonylamino group, a phenylethylsulfonylamino group or a pyridylmethylsulfonylamino group. Particularly preferred is a benzylsulfonylamino group or a phenylethylsulfonylamino group.

The $C_4$–$C_7$ cyclic imino group means a cyclic imino group having 4 to 7 carbon atoms such as a pyrrolidinyl group, a methylpyrrolidinyl group, a dimethylpyrrolidinyl group, a piperidino group, a methylpiperidino group, a dimethylpiperidino group, a morpholino group, a thiomorpholino group, a piperazino group, a methylpiperazino group or a hexamethyleneimino group. Among them, preferred is a pyrrolidinyl group, a piperidino group, a morpholino group or a piperazino group. Particularly preferred is a pyrrolidinyl group or a morpholino group.

The $C_3$–$C_8$ cycloalkyl $C_1$–$C_6$ alkyl group means a $C_1$–$C_6$ alkyl group having the above-mentioned $C_3$–$C_8$ cycloalkyl group such as a 1-cyclopropylethyl group, a 2-cyclopropylethyl group, a 2-cyclopropylpropyl group, a 3-cyclopropylpropyl group, a 4-cyclopropylbutyl group, a 5-cyclopropylpentyl group, a 6-cyclopropylhexyl group, a cyclobutylmethyl group, a 1-cyclobutylethyl group, a 2-cyclobutylethyl group, a cyclopentylmethyl group, a cyclohexylmethyl group or a cycloheptylmethyl group. Among them, preferred is a 2-cyclopropylethyl group, a 2-cyclobutylmethyl group, a cyclopentylmethyl group or a cyclohexylmethyl group. Particularly preferred is a 2-cyclobutylmethyl group or a cyclopentylmethyl group.

The carboxyl-protecting group means a lower alkyl group such as a methyl group, an ethyl group, a propyl group, an isopropyl group or a tert-butyl group; a lower haloalkyl group such as a 2,2,2-trichloroethyl group or a 2,2,2-trifluoroethyl group; a lower alkanoyloxyalkyl group such as an acetoxymethyl group, a propionyloxymethyl group, a pivaloyloxymethyl group, a 1-acetoxyethyl group or a 1-propionyloxyethyl group; a lower alkoxycarbonyloxyalkyl group such as a 1-(methoxycarbonyloxy)ethyl group, a 1-(ethoxycarbonyloxy)ethyl group or a 1-(isopropoxycarbonyloxy)ethyl group; a lower alkenyl group such as a 2-propenyl group, a 2-chloro-2-propenyl group, a 3-methoxycarbonyl-2-propenyl group, a 2-methyl-2-propenyl group, a 2-butenyl group or a cinnamyl group; an aralkyl group such as a benzyl group, a p-methoxybenzyl group, a 3,4-dimethoxybenzyl group, an o-nitrobenzyl group, a p-nitrobenzyl group, a benzhydryl group or a bis(p-methoxyphenyl)methyl group; a (5-substituted-2-oxo-1,3-dioxol-4-yl)methyl group such as a (5-methyl-2-oxo-1,3-dioxol-4-yl)methyl group; a lower alkylsilyl group such as a trimethylsilyl group or a tert-butyldimethylsilyl group; an indanyl group, a phthalidyl group or a methoxymethyl group. Particularly preferred is a 2-propenyl group, a p-nitrobenzyl group, a p-methoxybenzyl group, a benzhydryl group or a tert-butylmethylsilyl group.

The hydroxyl-protecting group means a lower alkylsilyl group such as a trimethylsilyl group or a tert-butyldimethylsilyl group; a lower alkoxymethyl group such as a methoxymethyl group or a 2-methoxyethoxyymethyl group; a tetrahydropyranyl group; an aralkyl group such as benzyl group, a p-methoxybenzyl group, a 2,4-dimethoxybenzyl group, an o-nitrobenzyl group, a p-nitrobenzyl group or a trityl group; an acyl group such as a formyl group or an acetyl group; a lower alkoxycarbonyl group such as a tert-butoxycarbonyl group, a 2-iodoethoxycarbonyl group or a 2,2,2-trichloroethoxycarbonyl group; an alkenyloxycarbonyl group such as a 2-propenyloxycarbonyl group, a 2-chloro-2-propenyloxycarbonyl group, a 3-methoxycarbonyl-2- propenyloxycarbonyl group, a 2-methyl-2-propenyloxycarbonyl group, a 2-butenyloxycarbonyl group or a cinnamyloxycarbonyl group; or an aralkyloycarbonyl group such as a benzyloxycarbonyl group, a p-methoxybenzyloxycarbonyl group, an o-nitrobenzyloxycarbonyl group or a p-nitrobenzyloxycarbonyl group. Particularly preferred is a 2-propenyloxycarbonyl group, a p-nitrobenzyloxycarbonyl group or a tert-butyldimethylsilyl group.

The amino-protecting group means an aralkylidene group such as a benzylidene group, a p-chlorobenzylidene group, a p-nitrobenzylidene group, a salicylidene group, an α-naphthylidene group or a β-naphthylidene group; an aralkyl group such as a benzyl group, a p-methoxybenzyl group, a 3,4-dimethoxybenzyl group, an o-nitrobenzyl group, a p-nitrobenzyl group, a benzhydryl group, a bis(p-methoxyphenyl)methyl group or a trityl group; a lower alkanoyl group such as a formyl group, an acetyl group, a propionyl group, a butyryl group, an oxalyl group, a succinyl group or a pivaloyl group; a lower haloalkanoyl group such as a chloroacetyl group, a dichloroacetyl group, trichloroacetyl group or a trifluoroacetyl group; an arylalkanoyl group such as a phenylacetyl group or a phenoxyacetyl group; a lower alkoxycarbonyl group such as a methoxycarbonyl group, an ethoxycarbonyl group, a propoxycarbonyl group or a tert-butoxycarbonyl group; a lower haloalkoxycarbonyl group such as a 2-iodoethoxycarbonyl group or a 2,2,2-trichloroethoxycarbonyl group; an alkenyloxycarbonyl group such as a 2-propenyloxycarbonyl group, a 2-chloro-2-propenyloxycarbonyl group, a 3-methoxycarbonyl-2-propenyloxycarbonyl group, a 2-methyl-2-propenyloxycarbonyl group, a 2-butenyloxycarbonyl group or a cinnamyloxycarbonyl group; an aralkyloxycarbonyl group such as a benzyloxycarbonyl group, an o-nitrobenzyloxycarbonyl group, a p-nitrobenzyloxycarbonyl group or a phenetyloxycarbonyl group; or a lower alkylsilyl group such as a trimethylsilyl group or a tert-butyldimethylsilyl group. Particularly preferred is a 2-propenyloxycarbonyl group, a tert-butoxycarbonyl group or a p-nitrobenzyloxycarbonyl group.

Now, the present invention will be described in more detail with reference to specific Examples for the various symbols used in general formulae.

Ar is a phenyl group, a thienyl group or a pyridyl group which may have one to three substituents selected from the group consisting of hydroxyl groups, amino groups, carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups Among them, preferred is a phenyl group or a pyridyl group which may have one to three substituents selected from the group consisting of hydroxyl groups, amino groups, carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups (hereinafter defined as $Ar^a$). Particularly preferred is a phenyl group which may have one to three substituents selected from the group consisting of hydroxyl groups, amino groups, carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups (hereinafter defined as $Ar^b$).

$Ar^c$ is a phenyl group, a thienyl group or a pyridyl group which may have one to three substituents selected from the group consisting of hydroxyl groups, amino groups, carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups.

$Ar^d$ is a phenyl group, a thienyl group or a pyridyl group which may have one to three substituents selected from the group consisting of hydroxyl groups, amino groups, carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups.

$Ar^0$ is a phenyl group, a thienyl group or a pyridyl group which may have one co three substituents selected from the group consisting of optionally protected hydroxyl groups, optionally protected amino groups, optionally protected carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups.

The above groups Ar, $Ar^a$, $Ar^b$, $Ar^c$, $Ar^d$ and $Ar^0$ may have one to three substituents selected from the group consisting of hydroxyl groups, amino groups, carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups. Among these substituents, preferred are hydroxyl groups, amino groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups. Particularly preferred are hydroxyl groups, $C_1$–$C_6$ alkyl groups, $C_1$–$C_6$ alkoxy groups, and mono- and di-$C_1$–$C_6$ alkylaminocarbonyl groups.

The above-mentioned $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups may further have one to three substituents selected from the group consisting of hydroxyl groups, amino groups, carboxyl groups, carbamoyl groups, $SO_3H$, $PO_3H_2$, $C_1$–$C_6$ alkoxy groups, $C_1$–$C_6$ alkoxycarbonyl groups, $C_1$–$C_6$ alkylsulfonylamino groups, $C_1$–$C_6$ alkylsulfonylaminocarbonyl groups, mono- and di-$C_1$–$C_6$ alkylamino groups, mono- and di-$C_1$–$C_6$ alkylaminocarbonyl groups, phenyl groups, pyridyl groups, imidazolyl groups, tetrazol-5-yl groups and tetrazol-5-ylaminocarbonyl groups, preferably one to three substituents selected from the group consisting of hydroxyl groups, amino groups, carboxyl groups, carbamoyl groups, $C_1$–$C_6$ alkoxy groups, $C_1$–$C_6$ alkoxycarbonyl groups, $C_1$–$C_6$ alkylsulfonylamino groups, $C_1$–$C_6$ alkylsulfonylaminocarbonyl groups, mono- and di-$C_1$–$C_6$ alkylamino groups and mono- and di-$C_1$–$C_6$ alkylaminocarbonyl groups, more preferably one to three substituents selected from the group consisting of hydroxyl groups, amino groups, carboxyl groups, carbamoyl groups, $C_1$–$C_6$ alkoxy groups, mono- and di-$C_1$–$C_6$ alkylamino groups and mono- and di-$C_1$–$C_6$ alkylaminocarbonyl groups. A hydroxyl group and a carboxyl group as substituents may form a lactone ring together.

$R^1$ is a hydrogen atom, a hydroxyl group, a cyano group, a nitro group, a carboxyl group, an amino group, a halogen atom, a $C_1$–$C_6$ alkyl group, a $C_3$–$C_8$ cycloalkyl group, a $C_3$–$C_8$ cycloalkyl $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkylthio group, a formyl group, a $C_2$–$C_6$ alkanoyl group, an aroyl group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl)amino group, a $C_2$–$C_6$ alkanoylamino group, an aroylamino group, an N—($C_1$–$C_6$ alkyl)-N-(aroyl)amino group, a $C_1$–$C_6$ alkylsulfonylamino group, an aryl $C_1$–$C_6$ alkylamino group, an N-(aryl $C_1$–$C_6$ alkyl)-N-(aroyl)amino group, an arylsulfonylamino group, an aryl $C_1$–$C_6$ alkylsulfonylamino group, a $C_4$–$C_7$ cyclic imino group or a $C_1$–$C_6$ alkoxycarbonyl group. Among them, preferred is a hydroxyl group, an amino group, a $C_1$–$C_6$ alkyl group, a $C_3$–$C_8$ cycloalkyl group, a $C_3$–$C_8$ cycloalkyl $C_1$–$C_6$ alkyl group, a $C_2$–$C_6$ alkenyl group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl)amino group, an aroylamino group, a $C_1$–$C_6$ alkylsulfonylamino group or a $C_4$–$C_7$ cyclic imino group (hereinafter defined as $R^{1a}$). Particularly preferred is a $C_1$–$C_6$ alkyl group, a mono- or di-$C_1$–$C_6$ alkylamino group, an aroylamino group or a $C_1$–$C_6$ alkylsulfonylamino group (hereinafter defined as $R^{1b}$).

$R^{1c}$ is an amino group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl)amino group, a $C_1$–$C_6$ alkanoylamino group, an aroylamino group, an N—($C_1$–$C_6$ alkyl)-N-(aroyl)amino group, a $C_1$–$C_6$ alkylsulfonylamino group, an aryl $C_1$–$C_6$ alkylamino group, an N-(aryl $C_1$–$C_6$ alkyl)-N-(aroyl)amino group, an arylsulfonylamino group, an aryl $C_1$–$C_6$ alkylsulfonylamino group or a $C_4$–$C_7$ cyclic imino group.

$R^{1d}$ is an amino group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl)amino group, an N—($C_1$–$C_6$ alkyl)-N-(aroyl) amino group or a $C_4$–$C_7$ cyclic imino group.

$R^1$, $R^{1a}$, $R^{1b}$, $R^{1c}$ and $R^{1d}$ may optionally have a substituent such as a hydroxyl group, an amino group, a $C_1$–$C_6$ alkyl group and a mono- or di-$C_1$–$C_6$ alkylamino group at any substitutable position, for example, on the alkyl moiety, the alkylene moiety or the aryl moiety. Specifically speaking, the $C_1$–$C_6$ alkyl group, the $C_3$–$C_8$ cycloalkyl group, the $C_3$–$C_8$ cycloalkyl $C_1$–$C_6$ alkyl group, the $C_2$–$C_6$ alkenyl group and the $C_2$–$C_6$ alkynyl group may have one to three substituents selected from the group consisting of hydroxyl groups, amino groups, $C_1$–$C_6$ alkoxy group and mono- and di-$C_1$–$C_6$ alkylamino groups, the mono- or di-$C_1$–$C_6$ alkylamino group may have a hydroxyl group on the alkyl moiety, the $C_3$–$C_8$ cycloalkylamino group, the $C_2$–$C_6$ alkanoylamino group, the N—($C_1$–$C_6$ alkyl)-N-(aroyl)amino group and the $C_1$–$C_6$ alkylsulfonylamino group may have a hydroxyl group on the alkyl moiety, the $C_3$–$C_8$ cycloalkyl $C_1$–$C_6$ alkylamino group and the N—($C_1$–$C_6$ alkyl)-N—($C_3$–$C_8$ cycloalkyl)amino group may have a hydroxyl group on the alkyl moiety or the alkylene moiety, the aryl $C_1$–$C_6$ alkylamino group, the N-(aryl $C_1$–$C_6$ alkyl)-N-(aroyl)amino group, the arylsulfonylamino group and the aryl $C_1$–$C_6$ alkylsulfonylamino group may have a $C_1$–$C_6$ alkyl group on the aryl moiety, and the $C_4$–$C_7$ cyclic imino group may have a hydroxy group on the alkylene moiety.

$R^2$ is a hydroxyl group, an amino group, a $C_1$–$C_6$ alkoxy group, a mono- or di-$C_1$–$C_6$ alkylamino group, a $C_1$–$C_6$ alkylsulfonylamino group or an arylsulfonylamino or an aryl $C_1$–$C_6$ alkylsulfonylamino group which may have a $C_1$–$C_6$ alkyl group. Among them, preferred is a hydroxyl group, a $C_1$–$C_6$ alkoxy group, a $C_1$–$C_6$ alkylsulfonylamino group or an arylsulfonylamino group which may have a $C_1$–$C_6$ alkyl group (hereinafter defined as $R^{2a}$). Particularly preferred is a hydroxyl group or an arylsulfonylamino group which may have a $C_1$–$C_6$ alkyl group (hereinafter defined as $R^{2b}$).

$R^{2c}$ is a hydroxyl group, an amino group, a $C_1$–$C_6$ alkoxy group, a mono- or di-$C_1$–$C_6$ alkylamino group, a $C_1$–$C_6$ alkylsulfonylamino group or an arylsulfonylamino or an aryl $C_1$–$C_6$ alkylsulfonylamino group which may have a $C_1$–$C_6$ alkyl group.

$R^{2d}$ is a hydroxyl group, an amino group, a $C_1$–$C_6$ alkoxy group, a mono- or di-$C_1$–$C_6$ alkylamino group, a $C_1$–$C_6$ alkylsulfonylamino group or an arylsulfonylamino or an aryl $C_1$–$C_6$ alkylsulfonylamino group which may have a $C_1$–$C_6$ alkyl group.

$R^3$ is a $C_1$–$C_6$ alkyl group.

$R^{3c}$ is a $C_1$–$C_6$ alkyl group.

$R^4$ is a hydrogen atom or a $C_1$–$C_6$ alkylcarbonyl group.

$R^5$ is a $C_1$–$C_6$ alkyl group or an aryl group.

$R^6$ is a hydroxyl-protecting group $R^7$ is a $C_1$–$C_6$ alkyl group, a $C_1$–$C_6$ cycloalkyl group or an aryl $C_1$–$C_6$ alkyl group.

$R^8$ is a hydrogen atom or an amino-protecting group, or a $C_1$–$C_6$ alkyl group, a $C_1$–$C_6$ cycloalkyl group or an aryl $C_1$–$C_6$ alkyl group.

$R^{10}$ is a hydrogen atom, an optionally protected hydroxyl group, a cyano group, a nitro group, an optionally protected carboxyl group, an optionally protected amino group, a halogen atom, a $C_1$–$C_6$ alkyl group, a $C_3$–$C_8$ cycloalkyl group, a $C_3$–$C_8$ cycloalkyl $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkylthio group, a formyl group, a $C_2$–$C_6$ alkanoyl group, an aroyl group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl)amino group, a $C_2$–$C_6$ alkanoylamino group, an aroylamino group, an N—($C_1$–$C_6$ alkyl)-N-(aroyl)amino group, a $C_1$–$C_6$ alkylsulfonylamino group, an aryl $C_1$–$C_6$ alkylamino group, an N-(aryl $C_1$–$C_6$ alkyl)-N-(aroyl)amino group, an arylsulfonylamino group, an aryl $C_1$–$C_6$ alkylsulfonylamino group, a $C_4$–$C_7$ cyclic imino group or a $C_1$–$C_6$ alkoxycarbonyl group.

Met is a metal atom.

X is a halogen atom.

Now, the compounds of general formula [I] will be described in more detail.

The compounds of the present invention are cyclopentenopyridine derivatives represented by general formula [I] or pharmaceutically acceptable salts thereof:

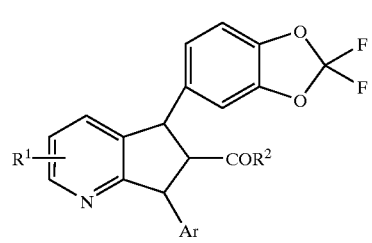

[I]

wherein Ar is a phenyl group, a thienyl group or a pyridyl group which may have one to three substituents selected from the group consisting of hydroxyl groups, amino groups, carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups, $R^1$ is a hydrogen atom, a hydroxyl group, a cyano group, a nitro group, a carboxyl group, an amino group, a halogen atom, a $C_1$–$C_6$ alkyl group, a $C_3$–$C_8$ cycloalkyl group, a $C_3$–$C_8$ cycloalkyl $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkylthio group, a formyl group, a $C_2$–$C_6$ alkanoyl group, an aroyl group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl)amino group, a $C_2$–$C_6$ alkanoylamino group, an aroylamino group, an N—($C_1$–$C_6$ alkyl)-N-(aroyl)amino group, a $C_1$–$C_6$ alkylsulfonylamino group, an aryl $C_1$–$C_6$ alkylamino group, an N-(aryl $C_1$–$C_6$ alkyl)-N-(aroyl)amino group, an arylsulfonylamino group, an aryl $C_1$–$C_6$ alkylsulfonylamino group, a $C_4$–$C_7$ cyclic imino group or a $C_1$–$C_6$ alkoxycarbonyl group, and $R^2$ is a hydroxyl group, an amino group, a $C_1$–$C_6$ alkoxy group, a mono- or di-$C_1$–$C_6$ alkylamino group, a $C_1$–$C_6$ alkylsulfonylamino group or an arylsulfonylamino or an aryl $C_1$–$C_6$ alkylsulfonylamino group which may have a $C_1$–$C_6$ alkyl group, preferably cyclopentenopyridine derivatives represented by general formula [I-a] or pharmaceutically acceptable salts thereof:

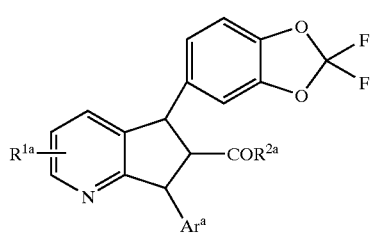

[I-a]

wherein $Ar^a$ is a phenyl group or a pyridyl group which may have one to three substituents selected from the group consisting of hydroxyl groups, amino groups, carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups, $R^{1a}$ is a hydroxyl group, an amino group, a $C_1$–$C_6$ alkyl group, a $C_3$–$C_8$ cycloalkyl group, a $C_3$–$C_8$ cycloalkyl $C_1$–$C_6$ alkyl group, a $C_2$–$C_6$ alkenyl group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl)amino group, an aroylamino group, a $C_1$–$C_6$ alkylsulfonylamino group or a $C_4$–$C_7$ cyclic imino group, and $R^{2a}$ is a hydroxyl group, a $C_1$–$C_6$ alkoxy group, a $C_1$–$C_6$ alkylsulfonylamino group or an arylsulfonylamino group which may have a $C_1$–$C_6$ alkyl group, and more preferably cyclopentenopyridine derivatives represented by general formula [I-b] or pharmaceutically acceptable salts thereof:

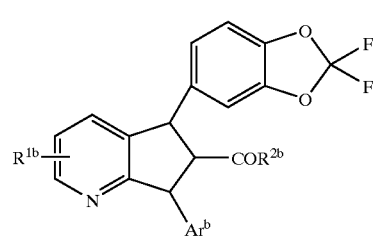

[I-b]

wherein $Ar^b$ is a phenyl group which may have one to three substituents selected from the group consisting of hydroxyl groups, amino groups, carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups, $R^{1b}$ is a $C_1$–$C_6$ alkyl group, a mono- or di-$C_1$–$C_6$ alkylamino group, an aroylamino group or a $C_1$–$C_6$ alkylsulfonylamino group, and $R^{2b}$ is a hydroxyl group or an arylsulfonylamino group which may have a $C_1$–$C_6$ alkyl group.

Next, specific examples of the compounds of general formula [I] are given in Table 2.

TABLE 2

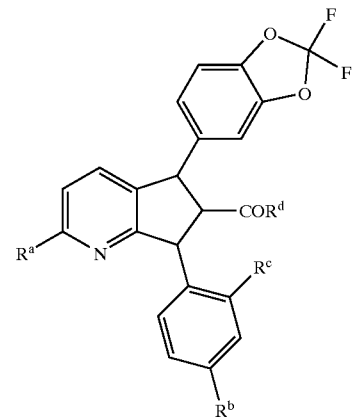

[I-e]

| No. | $R^a$ | $R^b$ | $R^c$ | $R^d$ |
|---|---|---|---|---|
| 1 | H | OMe | n-Pr | OH |
| 2 | H | OMe | n-Bu | OH |
| 3 | H | OMe | ⌁⌁ (allyl) | OH |
| 4 | H | OMe | —O—CH₂CH₂—Me | OH |
| 5 | H | OMe | —O—CH₂CH₂—OH | OH |
| 6 | H | OMe | —O—CH₂CH(Me)—OH | OH |
| 7 | H | OMe | —CH₂CH₂—OH | OH |
| 8 | H | OMe | —C(Me)₂—OH | OH |

TABLE 2-continued

[I-e]

(Structure: 2,2-difluoro-1,3-benzodioxol-5-yl group attached to a cyclopenta[b]pyridine core with R$^a$ on pyridine, R$^b$ on phenyl (para), R$^c$ on phenyl (ortho), and COR$^d$ substituent)

| No. | R$^a$ | R$^b$ | R$^c$ | R$^d$ |
|---|---|---|---|---|
| 9 | H | OMe | CH$_2$CH$_2$CH$_2$OH | OH |
| 10 | H | OMe | CH$_2$C(Me)$_2$OH | OH |
| 11 | H | OMe | CH(Me)CH$_2$OH (with ethyl) | OH |
| 12 | H | OMe | CH$_2$CH$_2$CO$_2$H | OH |
| 13 | H | OMe | CH(Me)CO$_2$H | OH |
| 14 | H | OMe | CH$_2$CH$_2$CH$_2$CO$_2$H | OH |
| 15 | H | OMe | CH(Me)CH$_2$CO$_2$H (with ethyl) | OH |
| 16 | H | OMe | CH(Me)CONH$_2$ | OH |
| 17 | H | OMe | CH(Me)CONHMe | OH |
| 18 | H | OMe | CH(Me)CONMe$_2$ | OH |
| 19 | NH$_2$ | OMe | n-Pr | OH |
| 20 | NH$_2$ | OMe | n-Bu | OH |
| 21 | NH$_2$ | OMe | CH$_2$CH$_2$OCH$_2$CH$_2$OH | OH |
| 22 | NH$_2$ | OMe | CH$_2$OCH$_2$CH(Me)CH$_2$OH | OH |
| 23 | NH$_2$ | OMe | CH(Me)CH$_2$OH (with ethyl branch) | OH |
| 24 | NH$_2$ | OMe | CH(Me)CH$_2$OMe (with ethyl) | OH |
| 25 | NH$_2$ | OMe | CH$_2$CH$_2$CONMe$_2$ | OH |
| 26 | NH$_2$ | OMe | CH(Me)CONH$_2$ | OH |
| 27 | NH$_2$ | OMe | CH(Me)CONMe$_2$ | OH |
| 28 | NHSO$_2$Me | OMe | n-Pr | OH |
| 29 | NHSO$_2$Me | OMe | n-Bu | OH |
| 30 | NHSO$_2$Me | OMe | CH(Me)CH$_2$OCH$_2$CH$_3$ | OH |
| 31 | NHSO$_2$Me | OMe | CH(Me)CH$_2$OH (with ethyl) | OH |
| 32 | NHSO$_2$Me | OMe | CH(Me)CH$_2$OMe (with ethyl) | OH |
| 33 | NHSO$_2$Me | H | n-Pr | OH |
| 34 | NHSO$_2$Me$_2$ | H | CH(Me)CH$_2$OH (with ethyl) | OH |
| 35 | NHSO$_2$Me | F | n-Pr | OH |

TABLE 2-continued

[I-e]

| No. | $R^a$ | $R^b$ | $R^c$ | $R^d$ |
|---|---|---|---|---|
| 36 | NHSO$_2$Me | F | 2-methylbutan-1-ol (Me, CH$_2$OH on ethyl) | OH |
| 37 | NHSO$_2$Et | OMe | n-Pr | OH |
| 38 | NHSO$_2$Et | OMe | 2-methylbutan-1-ol | OH |
| 39 | NHSO$_2$Et | H | 2-methylbutan-1-ol | OH |
| 40 | NHSO$_2$Et | F | 2-methylbutan-1-ol | OH |
| 41 | NH(n-Pr) | OMe | n-Pr | OH |
| 42 | NH(n-Pr) | OMe | 2-methylbutan-1-ol | OH |
| 43 | NH(iso-Pr) | OMe | n-Pr | OH |
| 44 | NH(iso-Pr) | OMe | n-Bu | OH |
| 45 | NH(iso-Pr) | OMe | CH$_2$CH$_2$OCH$_2$CH$_3$ (methoxypropyl) | OH |
| 46 | NH(iso-Pr) | OMe | CH$_2$CH$_2$OH | OH |
| 47 | NH(iso-Pr) | OMe | CH(Me)CH$_2$OH (propan-2-ol) | OH |
| 48 | NH(iso-Pr) | OMe | (CH$_2$)$_3$OH | OH |
| 49 | NH(iso-Pr) | OMe | C(Me)$_2$CH$_2$OH | OH |
| 50 | NH(iso-Pr) | OMe | (CH$_2$)$_4$OH | OH |
| 51 | NH(iso-Pr) | OMe | CH$_2$CH$_2$C(Me)$_2$OH | OH |
| 52 | NH(iso-Pr) | OMe | 2-methylbutan-1-ol | OH |
| 53 | NH(iso-Pr) | OMe | 2-methylbutyl methyl ether | OH |
| 54 | NH(iso-Pr) | OMe | OCH$_2$CH$_2$OH | OH |
| 55 | NH(iso-Pr) | OMe | OCH$_2$CH(Me)CH$_2$OH | OH |
| 56 | NH(iso-Pr) | OMe | CH$_2$CH$_2$CO$_2$H | OH |
| 57 | NH(iso-Pr) | OMe | CH(Me)$_2$CO$_2$H | OH |
| 58 | NH(iso-Pr) | OMe | CH(Et)(Me)CO$_2$H | OH |
| 59 | NH(iso-Pr) | OMe | CH(n-Pr)(Me)CO$_2$H | OH |
| 60 | NH(iso-Pr) | OMe | (CH$_2$)$_3$CO$_2$H | OH |
| 61 | NH(iso-Pr) | OMe | CH$_2$CH(Me)CO$_2$H | OH |
| 62 | NH(iso-Pr) | OMe | CH$_2$CH$_2$CONH$_2$ | OH |

TABLE 2-continued

[I-e]

| No. | $R^a$ | $R^b$ | $R^c$ | $R^d$ |
|---|---|---|---|---|
| 63 | NH(iso-Pr) | OMe | CH(Me)CONH$_2$ | OH |
| 64 | NH(iso-Pr) | OMe | CH(Me)CONHMe | OH |
| 65 | NH(iso-Pr) | OMe | CH(Me)CONMe$_2$ | OH |
| 66 | NH(iso-Pr) | OMe | CH$_2$CH$_2$CONH$_2$ | OH |
| 67 | NH(iso-Pr) | OMe | CH(Et)CONH$_2$ | OH |
| 68 | NH(iso-Pr) | OMe | CH(Et)CONMe$_2$ | OH |
| 69 | NH(iso-Pr) | H | OCH$_2$CH(Me)CH$_2$OH | OH |
| 70 | NH(iso-Pr) | H | CH(Et)CH$_2$OH | OH |
| 71 | NH(iso-Pr) | F | OCH$_2$CH(Me)CH$_2$OH | OH |
| 72 | NH(iso-Pr) | F | CH(Et)CH$_2$OH | OH |
| 73 | NH(n-Bu) | OMe | CH$_2$CH$_2$OH | OH |
| 74 | NH(n-Bu) | OMe | CH$_2$CH$_2$CH$_2$OH | OH |
| 75 | NH(n-Bu) | OMe | CH(Et)CH$_2$OH | OH |
| 76 | NH(n-Bu) | OMe | OCH$_2$CH$_2$OH | OH |
| 77 | NH(n-Bu) | OMe | OCH$_2$CH(Me)CH$_2$OH | OH |
| 78 | NH(n-Bu) | OMe | CH$_2$CH$_2$CO$_2$H | OH |
| 79 | NH(n-Bu) | OMe | CH(Me)CO$_2$H | OH |
| 80 | NH(n-Bu) | OMe | CH(Et)CO$_2$H | OH |
| 81 | NH(n-Bu) | OMe | CH$_2$CH$_2$CONMe$_2$ | OH |
| 82 | NH(n-Bu) | OMe | CH(Me)CONMe$_2$ | OH |
| 83 | NH-cyclopentyl | OMe | CH$_2$CH$_2$CH$_2$OH | OH |
| 84 | NH-cyclopentyl | OMe | CH(Et)CH$_2$OH | OH |
| 85 | NH-cyclopentyl | OMe | CH(Me)CO$_2$H | OH |
| 86 | NH-cyclopentyl | OMe | CH(Et)CO$_2$H | OH |

TABLE 2-continued

[I-e]

| No. | R$^a$ | R$^b$ | R$^c$ | R$^d$ |
|---|---|---|---|---|
| 87 | cyclopentyl-NH | OMe | -CH(Me)CONMe$_2$ | OH |
| 88 | cyclopentyl-NH | OMe | -CH(Me)CH$_2$CONMe$_2$ | OH |
| 89 | n-Pr | OMe | -CH$_2$CH$_2$OH | OH |
| 90 | n-Pr | OMe | -CH(Me)CH$_2$CH$_2$OH (Me branch) | OH |
| 91 | n-Pr | OMe | -CH$_2$CH$_2$CO$_2$H | OH |
| 92 | n-Pr | OMe | -CH(Me)CO$_2$H | OH |
| 93 | n-Pr | OMe | -CH(Et)CO$_2$H | OH |
| 94 | n-Pr | OMe | -CH(n-Pr)CO$_2$H | OH |
| 95 | n-Pr | OMe | -CH$_2$CH$_2$CH$_2$CO$_2$H | OH |
| 96 | n-Pr | OMe | -CH(Me)CH$_2$CO$_2$H | OH |
| 97 | n-Pr | OMe | -CH$_2$CH$_2$CONH$_2$ | OH |
| 98 | n-Pr | OMe | -CH$_2$CH$_2$CONMe$_2$ | OH |
| 99 | n-Pr | OMe | -CH(Me)CONMe$_2$ | OH |
| 100 | n-Pr | OMe | -CH$_2$CH$_2$CH$_2$CONMe$_2$ | OH |
| 101 | n-Pr | OMe | -CH(Me)CH$_2$CONMe$_2$ (Me/Et) | OH |
| 102 | n-Bu | OMe | -CH$_2$CH$_2$OH | OH |
| 103 | n-Bu | OMe | -CH$_2$CH$_2$CH$_2$OH | OH |
| 104 | n-Bu | OMe | -CH(Me)CH$_2$OH (Et branch) | OH |
| 105 | n-Bu | OMe | -CH$_2$OCH(CH$_2$OH)- | OH |
| 106 | n-Bu | OMe | -CH$_2$CH$_2$CO$_2$H | OH |
| 107 | n-Bu | OMe | -CH(Me)CO$_2$H | OH |
| 108 | n-Bu | OMe | -CH(n-Pr)CO$_2$H | OH |
| 109 | n-Bu | OMe | -CH(Me)CH$_2$CO$_2$H | OH |
| 110 | n-Bu | OMe | -CH(Me)CONH$_2$ | OH |
| 111 | n-Bu | OMe | -CH(Me)CONMe$_2$ | OH |

TABLE 2-continued

[I-e]

| No. | R$^a$ | R$^b$ | R$^c$ | R$^d$ |
|-----|-------|-------|-------|-------|
| 112 | n-Bu | OMe | Me–CH(–Et)–CONMe$_2$ | OH |
| 113 | NH(iso-Pr) | OMe | –CH$_2$CH$_2$OH | NHSO$_2$Me |
| 114 | NH(iso-Pr) | OMe | Me–CH(–Et)–CH$_2$OH | NHSO$_2$Me |
| 115 | NH(iso-Pr) | OMe | O–CH$_2$–CH(Me)–CH$_2$OH | NHSO$_2$Me |
| 116 | NH(iso-Pr) | OMe | Me–CH(–iPr)–CONMe$_2$ | NHSO$_2$Me |
| 117 | NH(iso-Pr) | OMe | Me–CH(–Et)–CONMe$_2$ | NHSO$_2$Me |

Among the compounds of general formula [I-e] given as specific examples, preferred compounds are (5S,6R,7R)-2-amino-6-carboxy-5-(2,2-difluoro-1,3-benzodioxol-5-yl)-7-[2-(3-hydroxy-2-methylpropyl)-4-methoxyphenyl]cyclopenteno[1,2,b]pyridine (Compound 23), (5S,6R,7R)-6-carboxy-5-(2,2-difluoro-1,3-benzodioxol-5-yl)-7-(2-propyl-4-methoxyphenyl)-2-(methanesulfonylamino)cyclopenteno[1,2,b]pyridine (Compound 28), (5S,6R,7R)-6-carboxy-5-(2,2-difluoro-1,3-benzodioxol-5-yl)-7-[2-(3-hydroxy-2-methylpropyl)-4-methoxyphenyl]-2-(methanesulfonylamino)cyclopenteno[1,2,b]pyridine (Compound 31), (5S,6R,7R)-6-carboxy-5-(2,2-difluoro-1,3-benzodioxol-5-yl)-7-[2-(3-hydroxy-2-methylpropyl)-4-methoxyphenyl]-2-N-propylaminocyclopenteno[1,2,b]pyridine (Compound 42), (5S,6R,7R)-6-carboxy-5-(2,2-difluoro-1,3-benzodioxol-5-yl)-7-(2-propyl-4-methoxyphenyl)-2-N-isopropylaminocyclopenteno[1,2,b]pyridine (Compound 43), (5S,6R,7R)-6-carboxy-5-(2,2-difluoro-1,3-benzodioxol-5-yl)-7-(2-hydroxymethyl-4-methoxyphenyl)-2-N-isopropylaminocyclopenteno[1,2,b]pyridine (Compound 46), (5S,6R,7R)-6-carboxy-5-(2,2-difluoro-1,3-benzodioxol-5-yl)-7-[2-(1-hydroxyethyl)-4-methoxyphenyl]-2-N-isopropylaminocyclopenteno[1,2,b]pyridine (Compound 47), (5S,6R,7R)-6-carboxy-5-(2,2-difluoro-1,3-benzodioxol-5-yl)-7-[2-(2-hydroxy-2-methylpropyl)-4-methoxyphenyl]-2-N-isopropylaminocyclopenteno[1,2,b]pyridine (Compound 49), (5S,6R,7R)-6-carboxy-5-(2,2-difluoro-1,3-benzodioxol-5-yl)-7-[2-(3-hydroxy-2-methylpropyl)-4-methoxyphenyl]-2-N-isopropylaminocyclopenteno[1,2,b]pyridine (Compound 52), (5S,6R,7R)-6-carboxy-5-(2,2-difluoro-1,3-benzodioxol-5-yl)-7-[2-(3-hydroxy-2-methylpropoxy)-4-methoxyphenyl]-2-N-isopropylaminocyclopenteno[1,2,b]pyridine (Compound 55), (5S,6R,7R)-6-carboxy-7-[2-(1-carboxyethyl)-4-methoxyphenyl]-5-(2,2-difluoro-1,3-benzodioxol-5-yl)-2-N-isopropylaminocyclopenteno[1,2,b]pyridine (Compound 57), (5S,6R,7R)-6-carboxy-7-[2-(1-carboxybutyl)-4-methoxyphenyl]-5-(2,2-difluoro-1,3-benzodioxol-5-yl)-2-N-isopropylaminocyclopenteno[1,2,b]pyridine (Compound 59), (5S,6R,7R)-6-carboxy-7-[2-(2-carboxypropyl)-4-methoxyphenyl]-5-(2,2-difluoro-1,3-benzodioxol-5-yl)-2-N-isopropylaminocyclopenteno[1,2,b]pyridine (Compound 61), (5S,6R,7R)-6-carboxy-5-(2,2-difluoro-1,3-benzodioxol-5-yl)-7-[2-(1-carbamoylethyl)-4-methoxyphenyl]-2-N-isopropylaminocyclopenteno[1,2,b]pyridine (Compound 63), (5S,6R,7R)-6-carboxy-5-(2,2-difluoro-1,3-benzodioxol-5-yl)-7-{2-[1-(N-methylaminocarbonyl)ethyl]-4-methoxyphenyl}-2-N-isopropylaminocyclopenteno[1,2,b]pyridine (Compound 64), (5S,6R,7R)-6-carboxy-5-(2,2-difluoro-1,3-benzodioxol-5-yl)-7-{2-[1-(N,N-dimethylaminocarbonyl)ethyl]-4-methoxyphenyl}-2-N-isopropylaminocyclopenteno[1,2,b]pyridine (Compound 65), (5S,6R,7R)-6-carboxy-5-(2,2-difluoro-1,3-benzodioxol-5-yl)-7-[2-(3-hydroxy-2-methylpropyl)phenyl]-2-N-isopropylaminocyclopenteno[1,2,b]pyridine (Compound 70), (5S,6R,7R)-6-carboxy-5-(2,2-difluoro-1,3-benzodioxol-5-yl)-7-[2-(3-hydroxy-2-methylpropoxy)-4-fluorophenyl]-2-N-isopropylaminocyclopenteno[1,2,b]pyridine (Compound 72), (5S,6R,7R)-6-carboxy-5-(2,2-difluoro-1,3-benzodioxol-5-yl)-7-(2-hydroxymethyl-4-methoxyphenyl)-2-N-butylaminocyclopenteno[1,2,b]pyridine (Compound 73), (5S,6R,7R)-6-carboxy-5-(2,2-difluoro-1,3-benzodioxol-5-yl)-7-[2-(3-hydroxy-2-methylpropyl)-4-methoxyphenyl]-2-N-butylaminocyclopenteno[1,2,b]pyridine (Compound 75), (5S,6R,7R)-6-carboxy-5-(2,2-difluoro-1,3-benzodioxol-5-yl)-7-[2-(3-hydroxy-2-methylpropoxy)-4-methoxyphenyl]-2-N-butylaminocyclopenteno[1,2,b]pyridine (Compound 77), (5S,6R,7R)-6-carboxy-7-[2-(1-carboxyethyl)-4-methoxyphenyl]-5-(2,2-difluoro-1,3-benzodioxol-5-yl)-2-propylcyclopenteno[1,2,b]pyridine (Compound 92), (5S,6R,7R)-6-carboxy-7-[2-(1-carboxyethyl)-4-methoxyphenyl]-5-(2,2-difluoro-1,3-benzodioxol-5-yl)-2-butylcyclopenteno[1,2,b]pyridine (Compound 107), (5S,6R,7R)-6-carboxy-7-[2-(1-carboxybutyl)-4-methoxyphenyl]-5-(2,2-difluoro-1,3-benzodioxol-5-yl)-2-butylcyclopenteno[1,2,b]pyridine (Compound 108), (5S,6R,7R)-6-carboxy-5-(2,2-difluoro-1,3-benzodioxol-5-yl)-7-{2-[1-(N,N-dimethylaminocarbonyl)ethyl]-4-methoxyphenyl}-2-butylcyclopenteno[1,2,b]pyridine (Compound 111) and (5S,6R,7R)-5-(2,2-difluoro-1,3-benzodioxol-5-yl)-7-{2-[1-(N,N-dimethylaminocarbonyl)ethyl]-4-methoxyphenyl}2-N-isopropylamino-6-methanesulfonylaminocarbonylcyclopenteno[1,2,b]pyridine (Compound 116). Among them, Compound 28, Compound 52, Compound 57, Compound 59, Compound 65, Compound 70, Compound 92 and Compound 107 are preferred. Particularly preferred is Compound 52.

The pharmaceutically acceptable salt of a compound of general formula [I] means a pharmaceutically acceptable common salt which may be a salt of a basic or acidic residue attributable to a functional group as the radical Ar, $R^1$ or $R^2$ such as a carboxyl group, a hydroxyl group or an amino group.

The base-addition salt of a carboxyl group, a hydroxyl group or an acidic residue may, for example, be an alkali metal salt such as a sodium salt or a potassium salt; an alkaline earth metal salt such as calcium salt or a magnesium salt; an ammonium salt; a trimethylamine salt or a triethylamine salt; an aliphatic amine salt such as a dicyclohexylamine salt, an ethanolamine salt, a diethanolamine salt, a triethanolamine salt or a procaine salt; a salt of an aralkylamine such as N,N'-dibenzylethylenediamine; an aromatic heterocyclic amine salt such as a pyridine salt, a picoline salt, a quinoline salt or an isoquinoline salt; a quaternary ammonium salt such as a tetramethylammonium salt, a tetraethylammonium salt, a benzyltrimethylammonium salt, a benzyltriethylammonium salt, a benzyltributylammonium salt, a methyltrioctylammonium salt or a tetrabutylammonium salt; or a basic amino acid salt such as an arginine salt or a lysine salt.

The acid-addition salt of a base may, for example, be an inorganic acid salt such as a hydrochloride, a sulfate, a nitrate, a phosphate, a carbonate, a hydrogencarbonate or a perchlorate; an organic acid salt such as an acetate, a propionate, a lactate, a maleate, a fumarate, a tartrate, a malate, a citrate or an ascorbate; a sulfonic acid salt such as a methanesulfonate, an isethionate, a benzenesulfonate or a p-toluenesulfonate; or an acidic amino acid salt such as an aspartate or an glutamate.

Now, processes for producing the compounds of the present invention will be described.

The compounds of the present invention represented by general formula [I] can be prepared by the following process A, B or C.

Process A

A compound represented by general formula [I] or its pharmaceutically acceptable salt:

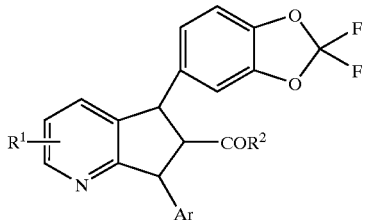

[I]

wherein Ar is a phenyl group, a thienyl group or a pyridyl group which may have one to three substituents selected from the group consisting of hydroxyl groups, amino groups, carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups, $R^1$ is a hydrogen atom, a hydroxyl group, a cyano group, a nitro group, a carboxyl group, an amino group, a halogen atom, a $C_1$–$C_6$ alkyl group, a $C_3$–$C_8$ cycloalkyl group, a $C_3$–$C_8$ cycloalkyl $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkylthio group, a formyl group, a $C_2$–$C_6$ alkanoyl group, an aroyl group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl)amino group, a $C_2$–$C_6$ alkanoylamino group, an aroylamino group, an N—($C_1$–$C_6$ alkyl)-N-(aroyl)amino group, a $C_1$–$C_6$ alkylsulfonylamino group, an aryl $C_1$–$C_6$ alkylamino group, an N-(aryl $C_1$–$C_6$ alkyl)-N-(aroyl)amino group, an arylsulfonylamino group, an aryl $C_1$–$C_6$ alkylsulfonylamino group, a $C_4$–$C_7$ cyclic imino group or a $C_1$–$C_6$ alkoxycarbonyl group, and $R^2$ is a hydroxyl group, an amino group, a $C_1$–$C_6$ alkoxy group, a mono- or di-$C_1$–$C_6$ alkylamino group, a $C_1$–$C_6$ alkylsulfonylamino group or an arylsulfonylamino or an aryl $C_1$–$C_6$ alkylsulfonylamino group which may have a $C_1$–$C_6$ alkyl group, can be prepared by reacting a compound represented by general formula [II]:

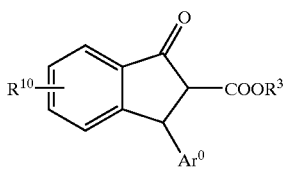

[II]

wherein $Ar^0$ is a phenyl group, a thienyl group or a pyridyl group which may have one to three substituents selected from the group consisting of optionally protected hydroxyl groups, optionally protected amino groups, optionally protected carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups, $R^3$ is $C_1$–$C_6$ alkyl group, and $R^{10}$ is a hydrogen atom, an optionally protected hydroxyl group, a cyano croup, a nitro group, an optionally protected carboxyl group, an optionally protected amino group, a halogen atom, a $C_1$–$C_6$ alkyl group, a $C_3$–$C_8$ cycloalkyl group, a $C_3$–$C_8$ cycloalkyl $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkylthio group, a formyl group, a $C_2$–$C_6$ alkanoyl group, an aroyl group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl)amino group, a $C_2$–$C_6$ alkanoylamino group, an aroylamino group, an N—($C_1$–$C_6$ alkyl)-N-(aroyl)amino group, a $C_1$–$C_6$ alkylsulfonylamino group, an aryl $C_1$–$C_6$ alkylamino group, an N-(aryl $C_1$–$C_6$ alkyl)-N-(aroyl)amino group, an arylsulfonylamino group, an aryl $C_1$–$C_6$ alkylsulfonylamino group, a $C_4$–$C_7$ cyclic imino group or a $C_1$–$C_6$ alkoxycarbonyl group, with an organic metal compound represented by general formula [III]:

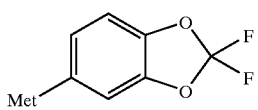

[III]

wherein Met is a metal atom, to obtain a compound represented by general formula [IV]:

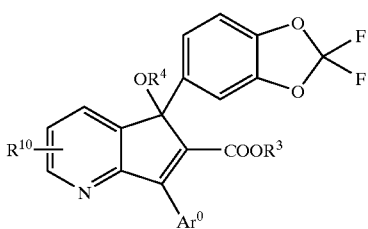

[IV]

wherein R⁴ is a hydrogen atom or a $C_1$–$C_6$ alkylcarbonyl group, and Ar⁰, R³ and R¹⁰ are the same as defined above, reducing the compound represented by general formula [IV] to obtain a compound represented by general formula [V]:

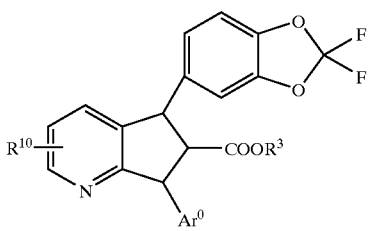

[V]

wherein Ar⁰, R³ and R¹⁰ are the same as defined above, and if necessary, subjecting the compound represented by general formula [V] to desired synthetically equivalent conversion of a functional group and/or removal of a protecting group, or conversion into a pharmaceutically acceptable salt thereof.

A compound of general formula [IV] can be prepared by reacting a compound of general formula [II] with from 1 to 4 equivalents, preferably from 1 to 2 equivalents of a compound of general formula [III], based on the compound of general formula [II] in a solvent such as THF, $Et_2O$ or dimethoxyethane at a temperature of from –100° C. to room temperature, preferably from –78° C. to –30° C., for from 0.5 to 4 hours, preferably from 0.5 to 2 hours.

The compound of general formula [IV] is treated with from 20 to 100 wt %, preferably from 50 to 100 wt % of an appropriate hydrogenation catalyst such as Pd—C, based on the compound of general formula [IV] in the presence of an appropriate acid such as acetic acid, sulfuric acid or perchloric acid under an atmosphere of hydrogen at a pressure of from atmospheric pressure to about 5 kg/cm², preferably from 1 to 3 kg/cm² at a temperature of from room temperature to 50° C., preferably from 20° C. to 40° C., or with from 5 to 15 equivalents, preferably from 8 to 12 equivalents of a mineral acid such as acetic acid or hydrochloric acid, based on the compound of general formula [IV], in a solvent mixture of an ethereal solvent such as THF, $Et_2O$ or dioxane and an alcoholic solvent such as methanol, ethanol or tert-butanol in the presence of from 5 to 15 equivalents, preferably from 8 to 12 equivalents of a metal such as zinc powder or iron powder, based on the compound of general formula [IV] at a temperature of from –78° C. to room temperature, preferably from 0° C. to 15° C., so that the double bond and the hydroxyl group of the compound of general formula [IV] can be reduced simultaneously, to obtain a compound of general formula [V].

After the reaction, conventional treatment is conducted to obtain a crude product of the compound represented by general formula [V], which may, if necessary, be appropriately converted without purification through desired synthetically equivalent conversion of a functional group, removal of a protecting group or hydrolysis of an ester group. It is preferred to subject the crude product [V] to crystallization or column chromatography using silica gel or the like for purification.

The compound of general formula [V] thus obtained can be converted into a compound of general formula [I] and if necessary, further into its pharmaceutically acceptable salt by properly combining conversion of a functional group into a desired synthetically equivalent one and reactions for removing protecting groups for a hydroxyl group, an amino group and a carboxyl group.

The desired synthetically equivalent conversion of a functional group means conversion of a substituent on the group Ar of the compound of general formula [V] into a desired substituent through reduction, oxidation, $C_1$–$C_6$ alkylation or the like. Specifically speaking, when the group Ar has an ester as a substituent, the compound of general formula [V] can be converted into an alcohol through its reduction, into an ether through $C_1$–$C_6$ alkylation of the alcohol, into a carboxylic acid through hydrolysis of the ester, into an amide through amidation. Thus, it means that the compound of general formula [V] is converted into a desired derivative through conversion of a functional group.

Removal of a protecting group can be achieved by an ordinary method, for example, solvolysis, chemical reduction or hydrogenation depending upon the type of the protecting group.

When the compound of general formula [V] has a hydroxyl group and/or an amino group protected with an aralkyloxycarbonyl group such as a benzyloxycarbonyl group or a p-nitrobenzyloxycarbonyl group, or a carboxyl group protected with an aralkyl group such as a benzyl group, a p-nitrobenzyl group or a benzhydryl group, the protecting group can be removed by catalytic hydrogenation using a platinum catalyst such as platinum oxide, platinum wire or platinum black; or a palladium catalyst such as palladium black, palladium oxide, palladium-carbon or palladium hydroxide-carbon.

For the catalytic hydrogenation, methanol, ethanol, tetrahydrofuran, dioxane or acetic acid or a mixture of such an organic solvent with water or phosphate or other buffer solution may be used as the solvent.

The catalytic hydrogenation is performed under a stream of hydrogen gas at from 1 to 4 atom, preferably at from 1 to 3 atom, at a temperature of from 0 to 50° C., preferably from 15 to 35° C., for from 0.5 to 24 hours, preferably from 5 to 15 hours.

When there is a hydroxyl group and/or an amino group protected with an allyloxycarbonyl group, or a carboxyl group protected with an allyl group in general formula [V], the protecting group can be removed by reaction with an organic solvent-soluble palladium complex catalyst in an inert organic solvent containing an allyl scavenger (the method of W. McCombie et al., J. Org. Chem., 47, 587–590 (1982) and the method of F. Guibé et al., ibid., 52, 4984–4993 (1987)).

For the reaction, water, acetone, diethylether, tetrahydrofuran, dioxane, ethyl acetate, acetonitrile, methylene chloride and chloroform and their mixtures may be used as a solvent.

Palladium complexes preferable for the reaction include for example, palladium-carbon, palladium hydroxide-carbon, palladium chloride (II), palladium acetate (II), tetrakis(triphenylphosphine)palladium (0), tetrakis (triphenoxyphosphine)palladium (0), tetrakis (triethoxyphosphine)palladium (0), bis[ethylenebis (diphenylphosphine)]palladium (0), tetrakis[tri(2-furyl) phosphine]palladium (0), bis(triphenylphosphine)palladium (II) chloride and bis(triphenylphosphine)palladium (II) acetate.

As the allyl scavenger, for example, dimedone, formic acid, acetic acid, ammonium formate, sodium formate, sodium 2-ethylhexanoate, potassium 2-ethylhexanoate, pyrrolidine, piperidine or tributyryltin hydride may be mentioned.

The reaction is conducted by using from 0.01 to 0.5 equivalent, preferably from 0.1 to 0.3 equivalent of a catalyst, and from 1 to 6 equivalents, preferably from 1 to 3 equivalents of a nucleophile, at a temperature of from $-10$ to $50°$ C., preferably from 0 to $30°$ C., and usually finishes in from 0.5 to 3 hours.

When there is a hydroxyl group and/or an amino group protected with an o-nitrobenzyloxycarbonyl group, or a carboxyl group protected by an o-nitrobenzyl group in general formula [V], the protecting group can be removed by photo reaction (the method of Amit et al., J. Org. Chem., 39 192–196 (1974)).

Removal of protecting groups is followed by usual treatment such as column chromatography using silica gel or an adsorptive resin, lyophilization or crystallization to isolate the compound of general formula [I].

A compound of general formula [I] can be converted into its pharmaceutically acceptable salt by an ordinary method.

A compound of general formula [II] can be prepared in accordance with the disclosure in WO9505374A1. A compound of general formula [III] is a known compound or, otherwise, can be prepared by known methods (Org. Synth., 3, 200–202 (1955) and Org. React., 6, 339–366 (1951))

Process B

A compound represented by general formula [I] or its pharmaceutically acceptable salt:

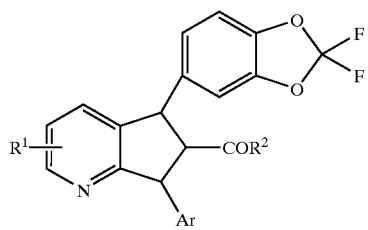

[I]

wherein Ar is a phenyl group, a thienyl group or a pyridyl group which may have one to three substituents selected from the group consisting of hydroxyl groups, amino groups, carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups, $R^1$ is a hydrogen atom, a hydroxyl group, a cyano group, a nitro group, a carboxyl group, an amino group, a halogen atom, a $C_1$-$C_6$ alkyl group, a $C_3$–$C_8$ cycloalkyl group, a $C_3$–$C_8$ cycloalkyl $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkylthio group, a formyl group, a $C_2$–$C_6$ alkanoyl group, an aroyl group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl)amino group, a $C_1$–$C_6$ alkanoylamino group, an aroylamino group, an N—($C_1$–$C_6$ alkyl)-N-(aroyl)amino group, a $C_1$–$C_6$ alkylsulfonylamino group, an aryl $C_1$–$C_6$ alkylamino group, an N-(aryl $C_1$–$C_6$ alkyl)-N-(aroyl)amino group, an arylsulfo- nylamino group, an aryl $C_1$–$C_6$ alkylsulfonylamino group, a $C_4$–$C_7$ cyclic imino group or a $C_1$–$C_6$ alkoxycarbonyl group, and $R^2$ is a hydroxyl group, an amino group, a $C_1$–$C_6$ alkoxy group, a mono- or di-$C_1$–$C_6$ alkylamino group, a $C_1$–$C_6$ alkylsulfonylamino group or an arylsulfonylamino or an aryl $C_1$–$C_6$ alkylsulfonylamino group which may have a $C_1$–$C_6$ alkyl group, can be prepared by reacting a compound represented by general formula [VI]:

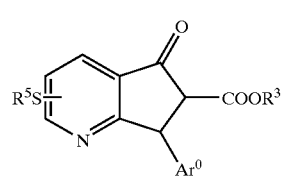

[VI]

wherein $Ar^0$ is a phenyl group, a thienyl group or a pyridyl group which may have one to three substituents selected from the group consisting of optionally protected hydroxyl groups, optionally protected amino groups, optionally protected carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups, $R^3$ is a $C_1$–$C_6$ alkyl group, and $R^5$ is a $C_1$–$C_6$ alkyl group or an aryl group, with an organic metal compound represented by general formula [III]:

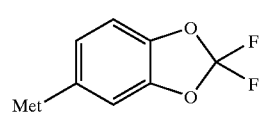

[III]

wherein Met is a metal atom, to obtain a compound represented by general formula [VII]:

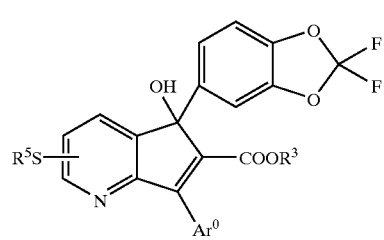

[VII]

wherein $Ar^0$, $R^3$ and $R^5$ are the same as defines above, then protecting the hydroxyl group of the compound represented by general formula [VII] to obtain a compound represented by general formula [VIII]:

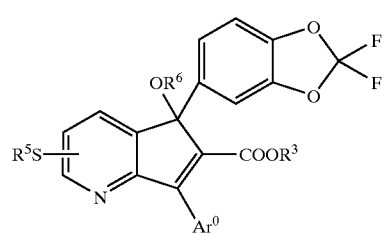

[VIII]

wherein $R^6$ is a hydroxyl-protecting group, and $Ar^0$, $R^3$ and $R^5$ are the same as defines above, further reacting the compound represented by general formula [VIII] with an oxidizing agent to obtain a compound represented by general formula [IX]:

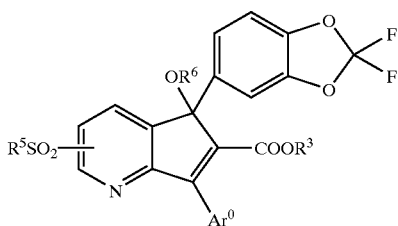

[IX]

wherein $Ar^0$, $R^3$, $R^5$ and $R^6$ are the same as defines above, reacting the compound represented by general formula [IX] with a compound represented by general formula [X]:

$R^{10}$-Met  [X]

wherein $R^{10}$ is a hydrogen atom, an optionally protected hydroxyl group, a cyano group, a carboxyl group, an optionally protected amino group, a $C_1$–$C_6$ alkyl group, a $C_3$–$C_8$ cycloalkyl group, a $C_3$–$C_8$ cycloalkyl $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkylthio group, a formyl group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl)amino group, a $C_2$–$C_6$ alkanoylamino group, an aroylamino group, an N—($C_1$–$C_6$ alkyl)-N-(aroyl)amino group, a $C_4$–$C_7$ cyclic imino group or a $C_1$–$C_6$ alkoxycarbonyl group, and Met is the same as defined above, co obtain a compound represented by the general formula:

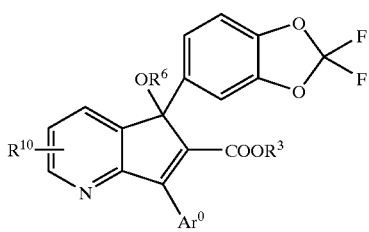

[XI]

wherein $Ar^0$, $R^3$, $R^6$ and $R^{10}$ are the same as defines above, then reducing the compound represented by general formula [XI] to obtain a compound represented by general formula [V]:

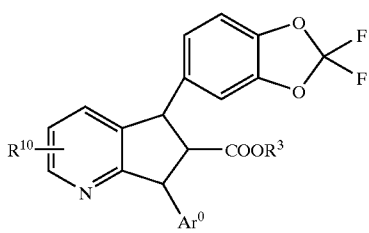

[V]

wherein $Ar^0$, $R^3$ and $R^{10}$ are the same as defines above, and if necessary, subjecting the compound represented by general formula [V] to desired synthetically equivalent conversion of a functional group and/or removal of a protecting group, or conversion into a pharmaceutically acceptable salt thereof.

The reactions except the reaction for production of the compound of general formula [XI] from the compound of general formula [IX] can be conducted in the same manners as those in Process A to give the compound of general formula [I].

A compound of general formula [XI] can be prepared by reacting a compound of general formula [IX] with from 1 to 5 equivalents, preferably from 1 to 3 equivalents of a compound of general formula [X], based on the compound of general formula [IX], in an inert solvent such as THF or Et$_2$O at a temperature of from −100° C. to room temperature, preferably from −78° C. to 25° C., for from 0.5 to 5 hours, preferably from 0.5 to 3 hours.

Specific examples of the compound of general formula [X] include organic lithium reagents, and nucleophiles having an anion moiety represented by $R^{10}$ such as lithium amide, mercaptide and alkoxide. These nucleophiles are known compounds or, otherwise, can be prepared by known methods.

A compound of general formula [I] can be prepared by the corresponding reactions in Process A of the compound [XI] resulting from substitution of the substituted sulfonyl group on the pyridine ring by the nucleophile.

A compound of general formula [VI] can be prepared in accordance with the disclosure in WO9505374A1.

Process C

Among the compounds of general formula [I] of the present invention, those having, on the pyridine ring, an amino group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl)amino group, a $C_2$–$C_6$ alkanoylamino group, an aroylamino group, an N—($C_1$–$C_6$ alkyl)-N-(aroyl)amino group, a $C_1$–$C_6$ alkylsulfonylamino group, an aryl $C_1$–$C_6$ alkylamino group, an N-(aryl $C_1$–$C_6$ alkyl)-N-(aroyl)amino group, an arylsulfonylamino group, an aryl $C_1$–$C_6$ alkylsulfonylamino group or a $C_4$–$C_7$ cyclic imino group, preferably an amino group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl)amino group, an N—($C_1$–$C_6$ alkyl)-N-(aroyl) amino group or a $C_4$–$C_7$ cyclic imino group, namely the cyclopentenopyridine derivatives represented by general formula [I-c] or their pharmaceutically acceptable salts:

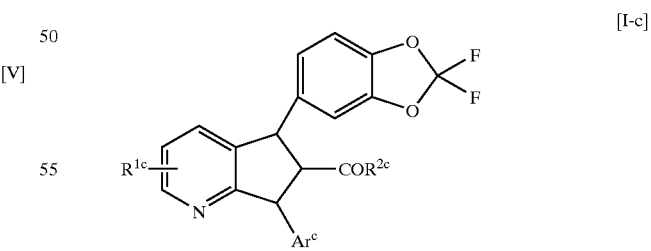

[I-c]

wherein $Ar^c$ is a phenyl group, a thienyl group or a pyridyl group which may have one to three substituents selected from the group consisting of hydroxyl groups, amino groups, carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups, $R^{1c}$ is an amino group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_1$–$C_8$ cycloalkyl)amino group, a $C_2$–$C_6$ alkanoylamino group, an aroylamino group, an N—($C_1$–$C_6$ alkyl)-N-(aroyl)amino group, a $C_1$–$C_6$ alkylsulfonylamino group, an aryl $C_1$–$C_6$ alkylamino group, an N-(aryl $C_1$–$C_6$ alkyl)-N-(aroyl)amino group, an arylsulfonylamino group, an aryl $C_1$–$C_6$ alkylsulfonylamino group or a $C_4$–$C_7$ cyclic imino group, and $R^{2c}$ is a hydroxyl group, an amino group, a $C_1$–$C_6$ alkoxy group, a mono- or di-$C_1$–$C_6$ alkylamino group, a $C_1$–$C_6$ alkylsulfonylamino group or an arylsulfonylamino or an aryl $C_1$–$C_6$ alkylsulfonylamino group which may have a $C_1$–$C_6$ alkyl group, preferably the cyclopentenopyridine derivatives represented by general formula [I-d] or their pharmaceutically acceptable salts:

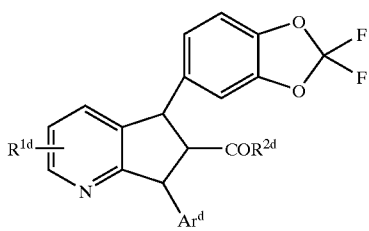

[I-d]

wherein $Ar^d$ is a phenyl group, a thienyl group or a pyridyl group which may have one to three substituents selected from the group consisting of hydroxyl groups, amino groups, carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$-$C_6$ alkylamino groups and mono- and di-$C_1$-$C_6$ alkylaminocarbonyl groups, $R^{1d}$ is an amino group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl)amino group, an N—($C_1$–$C_6$ alkyl)-N-(aroyl)amino group or a $C_4$–$C_7$ cyclic imino group, and $R^{2d}$ is a hydroxyl group, an amino group, a $C_1$–$C_6$ alkoxy group, a mono- or di-$C_1$–$C_6$ alkylamino group, a $C_1$–$C_6$ alkylsulfonylamino group or an arylsulfonylamino or an aryl $C_1$–$C_6$ alkylsulfonylamino group which may have a $C_1$–$C_6$ alkyl group, can be prepared by Process A and Process B mentioned above and also by the process described below.

Namely, a compound represented by general formula [I-c] or its pharmaceutically acceptable salt:

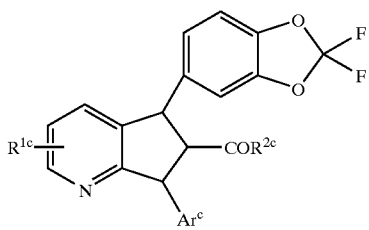

[I-c]

wherein $Ar^c$ is a phenyl group, a thienyl group or a pyridyl group which may have one to three substituents selected from the group consisting of hydroxyl groups, amino groups, carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups, $R^{1c}$ is a hydrogen atom, a hydroxyl group, a cyano group, a nitro group, a carboxyl group, an amino group, a halogen atom, a $C_1$–$C_6$ alkyl group, a $C_3$–$C_8$ cycloalkyl group, a $C_3$–$C_8$ cycloalkyl $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkylthio group, a formyl group, a $C_2$–$C_6$ alkanoyl group, an aroyl group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl)amino group, a $C_2$–$C_6$ alkanoylamino group, an aroylamino group, an N—($C_1$–$C_6$ alkyl)-N-(aroyl)amino group, a $C_1$–$C_6$ alkylsulfonylamino group, an aryl $C_1$–$C_6$ alkylamino group, an N-(aryl $C_1$–$C_6$ alkyl)-N-(aroyl)amino group, an arylsulfonylamino group, an aryl $C_1$–$C_6$ alkylsulfonylamino group, a $C_4$–$C_7$ cyclic imino group or a $C_1$–$C_6$ alkoxycarbonyl group, and $R^{2c}$ is a hydroxyl group, an amino group, a $C_1$–$C_6$ alkoxy group, a mono- or di-$C_1$–$C_6$ alkylamino group, a $C_1$–$C_6$ alkylsulfonylamino group or an arylsulfonylamino or an aryl $C_1$–$C_6$ alkylsulfonylamino group which may have a $C_1$–$C_6$ alkyl group, can be prepared by reacting a compound represented by general formula [XII]:

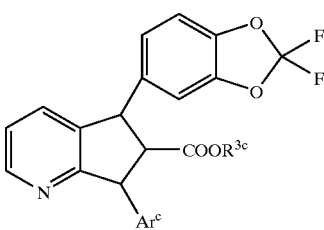

[XII]

wherein $R^{3c}$ is a $C_1$–$C_6$ alkyl group, and $Ar^c$ is the same as defined above, with an oxidizing agent to obtain a compound represented by general formula [XIII]:

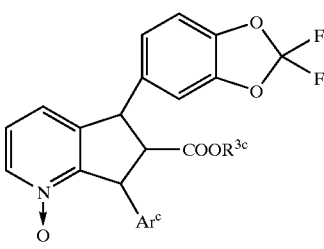

[XIII]

wherein $Ar^c$ and $R^{3c}$ are the same as defined above, then reacting the compound represented by general formula [XIII] with a compound represented by general formula [XIV]:

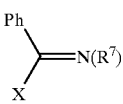

[XIV]

wherein $R^7$ is a $C_1$–$C_6$ alkyl group, a $C_1$–$C_6$ cycloalkyl group or an aryl $C_1$–$C_6$ alkyl group, and X is a halogen atom, to obtain a compound represented by general formula [XV]:

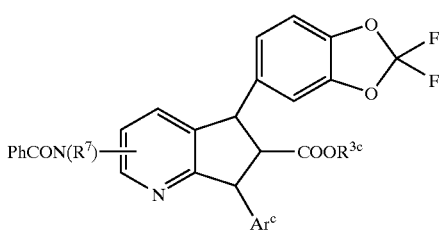

[XV]

wherein $Ar^c$, $R^{3c}$ and $R^7$ are the same as defined above, then if necessary, subjecting the compound represented by general formula [XV] to debenzoylation and/or dearyl $C_1$–$C_6$ alkylation, to obtain a compound represented by general formula [XVI]:

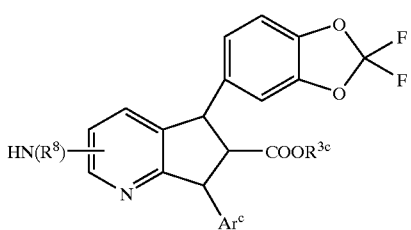

[XVI]

wherein $R^8$ is a hydrogen atom or an amino-protecting group, a $C_1$–$C_6$ alkyl group, a $C_1$–$C_6$ cycloalkyl group or an aryl $C_1$–$C_6$ alkyl group, and $Ar^c$ and $R^{3c}$ are the same as defined above, then if necessary, subjecting the compound represented by general formula [XVI] to one or two reactions in appropriate combination selected from the group consisting of $C_1$–$C_6$ alkylation, $C_3$–$C_8$ cycloalkylation, $C_3$–$C_8$ cycloalkyl $C_1C_6$ alkylation, $C_2$–$C_6$ alkanoylation, aroylation, sulfonylation, $C_f$–$C_6$ alkylsulfonylation, aryl $C_1$–$C_6$ alkylation, arylsulfonylation, aryl $C_1$–$C_6$ alkylsulfonylation and $C_4$–$C_7$ cyclic imination, and if necessary, subjecting the resulting compound to desired synthetically equivalent conversion of a functional group and/or removal of a protecting group, or conversion into a pharmaceutically acceptable salt thereof.

A compound of general formula [XIII] can be prepared by reacting a compound of general formula [XII] with from 1 to 3 equivalents, preferably from 1 to 1.5 equivalents, based on the compound of general formula [XII], of an oxidizing agent such as metachloroperbenzoic acid or sodium periodate in a solvent such as methylene chloride or chloroform at a temperature from −40° C. to room temperature, preferably from −20° C. to 5° C.

A compound of general formula [XV] can be prepared by reacting a compound of general formula [XIII] with from 2 to 30 equivalents, preferably from 2 to 5 equivalents, based on the compound of general formula [XIII], of a compound of general formula [XIV] (imidoyl halide) in a solvent such as methylene chloride, chloroform or 1,2-dichloroethane at a temperature from room temperature to the boiling point of the solvent, preferably from 40° C. to 70° C. The reaction is preferably carried out in the presence of from 10 to 50 equivalents, preferably from 3 to 10 equivalents of an inorganic base such as potassium hydrogencarbonate or cesium fluoride or an organic base such as triethylamine.

The imidoyl halide can be prepared by reacting the N-benzoyl form of a primary amine with a halogenating reagent such as thionyl chloride or phosphorus pentachloride in the absence of solvent or in the presence of an inert solvent such as benzene or toluene at a temperature of from room temperature to reflux temperature, preferably from 80° C. to 120° C. When the primary amine as the precursor of the imidoyl halide has a hydroxyl group as a substituent, it is preferred to protect the hydroxyl group beforehand by a protecting group such as an acetyl group, a benzyl group or a benzoyl group.

A compound of general formula [XVI] can, if necessary, be prepared by debenzoylation of a compound of general formula [XV] in the presence of 3 to 20 equivalents, preferably from 3 to 10 equivalents of a base such as sodium hydroxide, based on the compound of general formula [XV], in a solvent such as methanol or 1,4-dioxane, or in the presence of a reducing agent such as $BH_3$, 9-BBN or diisobutylaluminium hydride in a solvent such as THF or $Et_2O$ to remove the N-benzoyl group from the compound of general formula [XV], and, when $R^8$ is a substituted benzyl group, if necessary, subsequent dearyl $C_1$–$C_6$ alkylation by catalytic hydrogenation.

The above-mentioned debenzoylation and dearyl $C_1$–$C_6$ alkylation can be achieved by known methods (J. Am. Chem. Soc., 92, 204–205 (1970) and Tetrahedron. Lett., 38, 1717–1720 (1979)).

If necessary, the compound resulting from these reactions can be subjected to one or two reactions in appropriate combination selected from the group consisting of $C_1$–$C_6$ alkylation, $C_3$–$C_8$ cycloalkylation, $C_3$–$C_8$ cycloalkyl $C_1$–$C_6$ alkylation, $C_2$–$C_6$ alkanoylation, aroylation, sulfonylation, $C_1$–$C_6$ alkylsulfonylation, aryl $C_1$–$C_6$ alkylation, arylsulfonylation, aryl $C_1$–$C_6$ alkylsulfonylation and $C_4$–$C_7$ cyclic imination to introduce a desired substituent onto the amino or imino group of the compound.

The above-mentioned $C_1$–$C_6$ alkylation, $C_3$–$C_8$ cycloalkylation, $C_3$–$C_8$ cycloalkyl $C_1$–$C_6$ alkylation, $C_2$–$C_6$ alkanoylation, aroylation, sulfonylation, $C_1$–$C_6$ alkylsulfonylation, aryl $C_1$–$C_6$ alkylation, arylsulfonylation, aryl $C_1$–$C_6$ alkylsulfonylation and $C_4$–$C_7$ cyclic imination can be achieved by known methods (J. Chem. Soc., 992–994 (1970) and Org. Synth., 5, 88–91 (1951)).

Preferable examples include sulfonylation, $C_2$–$C_6$ alkanoylation and aroylation of the amino group; deprotection when $R^8$ is a $C_1$–$C_6$ alkyl group, a $C_1$–$C_6$ cycloalkyl group or an aryl $C_1$–$C_6$ alkyl group having a hydroxyl-deprotection; $C_1$–$C_6$ alkylation of the imino group through intramolecular or intermolecular nucleophilic substitution or intramolecular or intermolecular reductive alkylation; aroylation of the imino group; the above-mentioned desired synthetically equivalent conversion of a functional group; deprotection; or conversion into a pharmaceutically acceptable salt.

The above-mentioned nucleophilic substitution is preferably achieved by treatment with an alkyl halide such as an alkyl bromide or an alkyl iodide using a bulky strong base such as lithium hexamethyldisilazide or LDA in a solvent such a THF or ether at a temperature from −78° C. to room temperature, preferably from −20° C. to 25° C. The intramolecular substitution can be performed similarly after conversion of a hydroxyl group at a desired position into a leaving group such as a halide. The reductive alkylation is achieved by treatment with formalin or acetaldehyde in the presence of a reducing agent such as formic acid or sodium cyanoborohydride, at a temperature of from −20° C. to the boiling point of the solvent, preferably from 0° C. to 5° C. Intramolecular reductive alkylation is performed in the same manner as the intermolecular one after conversion into an aldehyde through selective oxidation of the hydroxyl group at a desired position.

A compound of general formula [XII] as the starting compound is a compound of general formula [V] wherein $R^{10}$ is a hydrogen atom and can be prepared from the corresponding compound of general formula [ii].

Among the compounds of general formula [I-c], particularly preferable compounds are the cyclopentenopyridine derivatives represented by general formula [I-c'] or their pharmaceutically acceptable salts:

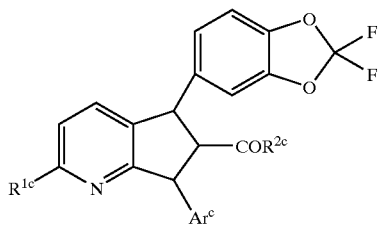

[I-c']

wherein $Ar^c$, $R^{1c}$ and $R^{2c}$ are the same as defined above.

Among the compounds of general formula [I] of the present invention, those for which no production process is not mentioned in detail above, can be prepared by appropriate combinations of the above-mentioned various reactions, various conversions of functional groups described in examples and known chemical reactions for protection or deprotection.

Intermediates and final products produced in Process A, Process B and Process C described above can be purified by known purification techniques such as recrystallization, reprecipitation, partitioning, normal or reversed phase chromatography or ion exchange chromatography.

Then, various pharmacological tests on the endothelin antagonistic activities of compounds of general formula [I] were conducted to demonstrate the usefulness of the present invention. The results of the tests will be described.

Test Example 1
Endothelin Binding Inhibition Test on Human Endothelin Recepters

The human neuroblastoma SK-N-MC cells or the human Giradi heart cells, purchased from Dainippon Seiyaku (Japan), were cultured in minimal essential medium supplemented with fetal calf serum. The cells were collected and homogenized in 10 mM MOPS buffer (pH 7.4) containing 154 mM NaCl, 10 mM KCl, 0.8 mM $CaCl_2$ and 20% sucrose at 4° C. using a polytron homogenizer. The homogenate was then centrifuged at 10,000×g for 15 minutes. The supernatant was centrifuged at 100,000×g for 1 hour at 4° C. Then the pellet was washed with 5 mM HEPES/Tris buffer (pH 7.4). The resulting membranes (50 $\mu$l) were mixed with [$^{125}$I]endothelin-1 (20 pM) and 4 $\mu$l of DMSO solution of a test compound in 67 mM Tris/HCl buffer (pH 7.4) containing 0.13 mM phenylmethanesulfonyl fluoride, 1.3 $\mu$M pepstatin, 2.7 $\mu$M leupeptin, 1.3 mM 1,10-phenanthroline, 1.3 mM EDTA, 13 $\mu$M $CaCl_2$, 13 $\mu$M $MgCl_2$ and 0.13% bovine serum albumin (BSA) in a total volume of 0.35 ml. After 4 hours incubation, cold 5 mM HEPES/Tris buffer (pH 7.4) containing 0.3% BSA (Buffer B) was added to the mixture, and free and bound [$^{125}$I]endothelin-1 were separated by filtration using Whatman GF/C glass fiber filters. After the filtration, the filters were washed with buffer B, and the radioactivity on the filters was measured in a γ counter. Nonspecific binding was determined in the presence of 200 nM endothelin-1.

The concentration of a test compound of the present invention causing 50% inhibition of [$^{125}$I]endothelin-1 binding ($IC_{50}$ value) was derived by the following [$^{125}$I] endothelin-1 binding inhibition D (%):

$$D\ (\%) = 100 - \frac{(C) - (A)}{(B) - (A)} \times 100$$

where (A): for nonspecific binding including 200 nM of unlabeled endothelin-1 as the final concentration, (B): for total binding including labeled endothelin-1 without a test compound, and (C): for binding including labeled endothelin-1 with a concentration of a test compound, show the radioactivity.

As is clear from the results indicated in Table 3, the diastereomer A prepared in Example 18 which is representative of the present invention, exhibited the excellent $IC_{50}$ values for ET receptors and far higher binding-inhibitory activity to $ET_A$ receptor than to $ET_B$ receptor. Furthermore, it was found that the selectivity of the compound was much higher than that of the corresponding methylenedioxyphenyl analogues.

TABLE 3

Inhibitory Effects on binding to $ET_A$ and $ET_B$ receptors

| | |
|---|---|
| X = F | $ET_A$ = 0.056 nM |
| Diastereomer A of | $ET_B$ = 78 nM |
| example 18 | $ET_B/ET_A$ = 1400 |
| X = H | $ET_A$ = 0.042 nM |
| Diastereomer A of | $ET_B$ = 1.0 nM |
| Reference Compound | $ET_B/ET_A$ = 24 |

Test Example 2
Effect on Endothelin-induced Contraction of Iliac Artery Specimen from Rabbit The iliac artery was excised from a rabbit and made into a spiral specimen of 1 mm wide and 10 mm long. The specimen was stripped of the endothelial cells and suspended in a 5 ml Magnus tube filled with Krebs-Henseleit solution saturated with a gas mixture of $O_2$ (95%) and $CO_2$ (5%), and the change in tension was isometrically measured and recorded.

The effects of a compound of the present invention on the dose-response curve obtained by cumulative addition of endothelin-1 to the Magnus tube were investigated. A compound of the present invention was added to the Magnus tube at a final concentration of 10 $\mu$M 20 minutes before the addition of endothelin-1.

The diastereomer A prepared in Example 14, which is representative of the compounds of the present invention, appreciably shifted the dose-response curve for endothelin-1 to the right at concentrations from 0.1 $\mu$M to 10 $\mu$M with no change in the maximum response. The compound of the present invention had no effect on the artery specimen by itself. As described above, the compounds of the present invention showed remarkable antagonism against endothelin-induced contraction of the artery specimen.

Test Example 3
Concentration in Rat Plasma after Oral Administration

SD male rats (8 weeks old, n=3) were subjected to cannulation of the carotid artery beforehand and after the recovery from the surgery, subjected to a fast of one night for the test. The sodium salt of the diastereomer A prepared in Example 14, which is a representative compound of the present invention, was dissolved in water, and the resulting aqueous solution (concentration: 2.0 mg/ml) was forcibly administrated into the stomach in an amount of 10 mg/kg by gavage. Before the administration and 1, 4 and 8 hours after the administration, 120 $\mu$l of the blood was withdrawn from the cannulae in the carotid arteries with the aid of heparin and the plasma was separated by cold centrifugation. 25 $\mu$l of portions of the plasma were deproteinized by adding 100 $\mu$l of ethanol and centrifuged (10,000×g, 10 minutes, 0° C.) under cooling. 80 $\mu$l portions of the supernatants was used for a bioassay of the concentration in plasma. The results showed that the diastereomer A prepared in Example 14, which is a representative compound of the present invention, remained in the rat plasma at concentrations of 452 ng/ml, 124 ng/ml and 203 ng/ml, 1, 4 and 8 hours after the oral administration.

Thus, it was found that the compound of the present invention appreciable oral absorbability and persistency in blood.

Thus, the compounds of the present invention have excellent endothelin antagonistic activities against the endothelin receptor and are useful as vasodilators or bronchodilators in the field of the medicines, and they can be drugs for treating one or more diseases selected from the group consisting of hypertension, pulmonary hypertension, Raynaud's disease, acute renal failure, heat failure, myocardial infarction, angina pectoris, cerebral infarction, cerebral vasospasm, arteriosclerosis, asthma, gastric ulcer, diabetes, restenosis, prostatism, endotoxin-induced multiple organ failure, disseminated intravascular coagulation, and cyclosporin-introduced renal failure and hypertension. When used as drugs for treating such diseases, the compounds of the present invention can be used alone or in combination with other drugs for treatment.

The compounds of the present invention may be used in the form of drug formulations suitable for parenteral administration, oral administration or external administration by mixing them with solid or liquid excipient carriers known in this field mainly for regional parenteral administration or parenteral administration by injection (intravenous injection or intramuscular injection). The drug formulations include a liquid formulation such as an injection formulation, a syrup formulation or an emulsion, a solid formulation such as tablets, capsules or granules, and an external drug such as an ointment or a suppository. Further, these drug formulations may contain additives which are commonly employed, such as a base, an adjuvant, a stabilizer, a wetting agent, an emulsifier, a sorbefacient or a surfactant, as the case requires.

As the additives, distilled water for injection, Ringer's solution, glucose, sucrose syrup, gelatin, vegetable oil, cacao butter, ethylene glycol, sucrose, corn starch, magnesium stearate and talc may be mentioned.

The dose of a compound of the present invention as an endothelin antagonist varies depending upon the condition, body weight, age and sex of the patient and the mode and frequency of administration. However, a typical administration method for an adult is oral administration or parenteral administration. The daily dose in the case of oral administration to an adult patient is from 0.1 to 100 mg/kg body weight, and the daily dose in the case of parenteral administration is from 0.01 to 10 mg/kg body weight.

EXAMPLES and REFERENCE EXAMPLES

The following Examples illustrate the present invention more specifically. It should be understood that the present invention is not limited to these examples alone.

Example 1

(5S,6R,7R)-6-Carboxy-5-(2,2-difluoro-1,3-benzodioxol-5-yl)-7-{2-[1-(N-methylaminocarbonyl)ethyl]-4-methoxyphenyl}-2-N-isopropylaminocyclopenteno[1,2,b]pyridine (1) (5RS,6SR,7SR)-6-tert-Butoxycarbonyl-5-(2,2-difluoro-1,3-benzodioxol-5-yl)-7-[2-(1-ethoxycarbonylvinyl)-4-methoxyphenyl]cyclopenteno[1,2,b]pyridine To (5RS,6SR,7SR)-6-tert-butoxycarbonyl-5-(2,2-difluoro-1,3-benzodioxol-5-yl)-7-(4-methoxy-2-trifluoromethanesulfonyloxyphenyl)cyclopenteno[1,2,b]pyridine (7.47 g, 11.9 mmol) in DMF (120 ml), ethyl 2-(tributylstannyl)acrylate (6.9 ml), bis(tri-o-tolylphosphine)palladium chloride (551 mg, 1.81 mmol) and lithium chloride (1.55 g, 36.6 mmol) were added, and the resulting reaction solution was stirred in a stream of nitrogen at 120° C. for 1 hour. The reaction solution was allowed to cool to room temperature and stirred with aqueous potassium fluoride at the same temperature for 30 minutes. The reaction mixture was filtered though celite and diluted with ethyl acetate, and the organic layer was washed with water three times and further with saturated aqueous sodium chloride, dried over $MgSO_4$ and concentrated under reduced pressure. Purification of the resulting residue by silica gel chromatography (Wacogel™ C-300, hexane-ethyl acetate) gave the above-identified compound (4.93 g, yield: 72%).

$^1$H-NMR (300 MHz, $CDCl_3$, $\delta$ ppm) 1.29 (3H, t, J=7.3 Hz), 1.30 (9H, s), 3.24 (1H, dd, J=9.9, 9.5 Hz), 3.79 (3H, s), 4.21 (2H, q, J=7.3 Hz), 4.54 (1H, d, J=9.5 Hz), 4.87 (1H, d, J=9.9 Hz), 5.92 (1H, d, J=1.2 Hz), 6.55 (1H, d, J=1.5 Hz), 6.77–8.46 (9H, m)

(2) (5RS,6SR,7SR)-6-tert-Butoxycarbonyl-5-(2,2-difluoro-1,3-benzodioxol-5-yl)-7-[2-(1-ethoxycarbonylethyl)-4-methoxyphenyl]cyclopenteno[1,2,b]pyridine To (5RS,6SR,7SR)-6-tert-butoxycarbonyl-5-(2,2-difluoro-1,3-benzodioxol-5-yl)-7-[2-(1-ethoxycarbonylvinyl)-4-methoxyphenyl]cyclopenteno[1,2,b]pyridine (4.93 g, 8.49 mmol) in ethanol (80 ml), 10% Pd—C (5.0 g) was added, and the resulting solution was heated to 70° C. and stirred with ammonium formate (2.70 g, 42.4 mmol) at the same temperature for 1 hour. The reaction mixture was filtered through celite, and the filtrate was concentrated under reduced pressure. The resulting residue was extracted with ethyl acetate. The organic layer was washed with water and saturated aqueous sodium chloride successively, dried over MgSO$_4$ and concentrated under reduced pressure to give a diastereomeric mixture of the above-identified compound (4.61 g, yield: 93%).

$^1$H-NMR (300 MHz, CDCl$_3$, δ ppm) 1.19 (3H, t, J=7.1 Hz), 1.31, 1.35 (9H, each s), 1.54, 1.59 (3H, each d, J=7.0 Hz), 3.29 (1H, dd, J=9.8, 9.3 Hz), 3.55–3.70 (1H, m), 3.77, 3.79 (3H, each s), 4.14 (2H, q, J=7.1 Hz ), 4.59 (1H, d, J=9.3 Hz ), 5.02 (1H, d, J=9.8 Hz), 6.74–8.47 (9H, m)

(3) (5RS,6SR,7SR)-6-tert-Butoxycarbonyl-5-(2,2-difluoro-1,3-benzodioxol-5-yl)-7-[2-(1-ethoxycarbonylethyl)-4-methoxyphenyl]-2-N-isopropylaminocyclopenteno[1,2,b]pyridine To (5RS,6SR,7SR)-6-tert-butoxycarbonyl-5-(2,2-difluoro-1,3-benzodioxol-5-yl)-7-[2-(1-ethoxycarbonylethyl)-4-methoxyphenyl]cyclopenteno[1,2,b]pyridine (4.61 g, 7.93 mmol) in chloroform (50 ml), metachloroperbenzoic acid (4.79 g, 27.7 mmol) was added in a stream of nitrogen at 0° C., and the resulting reaction solution was stirred at the same temperature overnight. After addition of Na$_2$S$_2$O$_3$, the reaction solution was washed with aqueous NaHCO$_3$ and saturated aqueous sodium chloride successively. Drying of the organic layer over MgSO$_4$ followed by concentration under reduced pressure gave (5RS,6SR,7SR)-6-tert-butoxycarbonyl-5-(2,2-difluoro-1,3-benzodioxol-5-yl)-7-[2-(1-ethoxycarbonylethyl)-4-methoxyphenyl]cyclopenteno[1,2,b]pyridine N-oxide (5.15 g, 7.93 mmol). To the compound in chloroform (45 ml), triethylamine (7.2 ml, 51.6 mmol) and N-isopropylbenzimidoyl chloride (4.8 g, 26.4 mmol) were added, and the resulting reaction solution was stirred in a stream of nitrogen at 70° C. for 7 hours. After addition of water, the reaction solution was extracted with ethyl acetate. The organic layer was washed with saturated aqueous sodium chloride, dried over MgSO$_4$ and concentrated under reduced pressure. The resulting residue was dissolved in THF (50 ml), 9-BBN (0.5 M THF solution, 50 ml) was added in a stream of nitrogen at room temperature, and the resulting reaction solution was stirred at the same temperature for 4 hours. The reaction solution was further stirred with 1N sodium hydroxide (70 ml) and 30% aqueous hydrogen peroxide (35 ml) for another 1 hour. The reaction mixture was extracted with ethyl acetate, and the organic layer was washed with aqueous Na$_2$S$_2$O$_3$ and saturated aqueous sodium chloride successively, dried over MgSO$_4$ and concentrated under reduced pressure. Purification of the resulting residue by silica gel chromatography (Wacogel™ C-200, hexane-ethyl acetate) gave a diastereomeric mixture of the above-identified compound (3.26 g, yield: 61%).

$^1$H-NMR (300 MHz, CDCl$_3$, δ ppm) 1.14 (3H, t, J=6.6 Hz), 1.18 (3H, d, J=6.7 Hz), 1.33 (3H, d, J=6.7 Hz), 1.37 (9H, s), 1.53 (3H, d, J=7.0 Hz), 3.08–3.18 (1H, m), 3.59–3.70 (1H, m), 3.76, 3.78 (3H, each s), 4.12 (2H, q, J=6.6 Hz), 4.22–4.51 (2H, m), 4.63–4.90 (1H, m), 6.17–7.35 (8H, m)

(4) (5RS,6SR,7SR)-6-tert-Butoxycarbonyl-5-(2,2-difluoro-1,3-benzodioxol-5-yl)-7-[2-(1-carboxyethyl)-4-methoxyphenyl]-2-N-isopropylaminocyclopenteno[1,2,b]pyridine To (5RS,6SR,7SR)-6-tert-butoxycarbonyl-5-(2,2-difluoro-1,3-benzodioxol-5-yl)-7-[2-(1-ethoxycarbonylethyl)-4-methoxyphenyl]-2-N-isopropylaminocyclopenteno[1,2,b]pyridine (3.26 g, 5.24 mmol) in methanol (95 ml), 4N sodium hydroxide (15 ml) was added, and the resulting reaction solution was stirred at room temperature overnight. The reaction solution was neutralized with 1N hydrochloric acid and concentrated under reduced pressure, and the resulting residue was extracted ethyl acetate. The organic layer was washed with saturated aqueous sodium chloride, dried over MgSO$_4$ and concentrated under reduced pressure. Purification by silica gel chromatography (Wacogel™ C-300, chloroform-methanol) separated the resulting residue into the diastereomer A (1.78 g, yield: 57%) and diastereomer B (731 mg, yield: 23%) of the above-identified compound.

Diastereomer A $^1$H-NMR (300 MHz, CDCl$_3$, δ ppm): 1.15–1.20 (6H, m), 1.29 (9H, s), 1.44 (3H, d, J=6.7 Hz), 2.94–3.08 (1H, m) 3.59–3.74 (1H, m), 3.79 (3H, s), 4.46 (1H, d, J=9.6 Hz), 4.60–4.80 (2H, brs), 6.25–7.25 (8H, m)

Diastereomer B $^1$H-NMR (300 MHz, CDCl$_3$, δ ppm) 1.16 (3H, d, J=6.3 Hz), 1.19 (3H, d, 6.3 Hz), 1.32 (9H, s), 1.52 (3H, d, J=6.8 Hz), 3.49–3.60 (1H, m), 3.59 (1H, dd, J=9.8, 8.8 Hz), 3.79 (3H, s), 4.17 (1H, q, J=6.8 Hz), 4.56 (1H, d, J=8.8 Hz), 4.91 (1H, d, J=9.8 Hz), 6.29 (1H, d, J=8.5 Hz), 6.78–7.16 (7H, m)

(5) Optical resolution of the diastereomer A (1.02 g) of (5RS,6SR,7SR)-6-tert-butoxycarbonyl-5-(2,2-difluoro-1,3-benzodioxol-5-yl)-7-[2-(1-ethoxycarbonylethyl)-4-methoxyphenyl]-2-N-isopropylaminocyclopenteno[1,2,b] pyridine using an optically active column (CHRALPAC™ AD, Dycel Kagaku Co., Ltd., hexane:isopropanol=95:5, flow rate=7 ml/min, tR=14.8 min, tR=17.0 min) gave the (5S,6R,7R) form (380 mg, yield: 32%) and (5R,6S,7S) form (392 mg, yield: 33%) of the diastereomer A. Similar optical resolution of the diastereomer B (1.10 g) gave the (5S,6R,7R) form (390 mg, yield: 35%) and (5R,6S,7S) form (385 mg, yield: 35%) of the diastereomer B.

(6) (5S,6R,7R)-6-tert-Butoxycarbonyl-5-(2,2-difluoro-1,3-benzodioxol-5-yl)-7-{2-[1-(N-methylaminocarbonyl)ethyl]-4-methoxyphenyl}-2-(N-isopropylamino)cyclopenteno[1,2,b]pyridine To the diastereomer A (363 mg, 0.61 mmol) of (5S,6R,7R)-6-tert-butoxycarbonyl-5-(2,2-difluoro-1,3-benzodioxol-5-yl)-7-[2-(1-carboxyethyl)-4-methoxyphenyl]-2-(N-isopropylamino)cyclopenteno[1,2,b]pyridine in DMF (7.0 ml), methylamine hydrochloride (574 mg, 8.50 mmol), HOBT (392 mg, 2.56 mmol), EDCI (498 mg, 2.60 mmol), DMAP (10 mg) and triethylamine (1.2 ml, 8.60 mmol) were added, and the resulting reaction solution was stirred in a stream of nitrogen at 0° C. overnight. The reaction solution was neutralized with 1N hydrochloric acid, poured into water and extracted with ethyl acetate. The organic layer was washed with saturated aqueous NaHCO$_3$ and saturated aqueous sodium chloride, dried over MgSO$_4$ and concentrated under reduced pressure. Purification of the resulting residue by silica gel chromatography (Wacogel™ C-300, chloroform-methanol) gave the above-identified compound (269 mg, yield: 69%).

$^1$H-NMR (300 Hz, CDCl$_3$, δ ppm): 1.12 (6H, d, J=6.7 Hz), 1.30 (9H, s), 2.70 (3H, d, J=5.2 Hz), 3.08–3.23 (1H, br), 3.56–3.78 (1H, m), 3.79 (3H, s), 4.31–4.62 (3H, br), 6.64–7.20 (8H, m)

(7) To the diastereomer A (269 mg, 0.443 mmol) of (5S,6R,7R)-6-tert-butoxycarbonyl-5-(2,2-difluoro-1,3-benzodioxol-5-yl)-7-{2-(1-(N-methylaminocarbonyl)ethyl]-4-methoxyphenyl}-2-(N-isopropylamino)cyclopenteno[1,2,b]pyridine, TFA (4.0 ml) was added, and the resulting reaction solution was stirred at room temperature for 1 hour. The reaction solution was concentrated under reduced pressure, and the resulting residue was extracted with ethyl acetate. The organic layer was washed with saturated aqueous NaHCO$_3$ three times and then with saturated aqueous sodium chloride, dried over MgSO$_4$ and concentrated under reduced pressure. Purification of the resulting residue by silica gel chromatography (Wacogelv C-300, chloroform-methanol) gave the diastereomer A (122 mg, yield: 50%) of the title compound.

Diastereomer A

High resolution FAB-MS (m/e, (as C$_{30}$H$_{32}$F$_2$N$_2$O$_6$+H)$^+$): Anal. Calcd 568.2259 Anal. Found 568.2258

$^1$H-NMR (300 MHz, CDCl$_3$, δ ppm): 1.13 (3H, d, J=6.2 Hz), 1.17 (3H, d, J=6.2 Hz), 1.33 (3H, d, J=5.6 Hz), 2.50–2.70 (3H, brs), 3.01–3.10 (1H, m), 3.58–3.75 (2H, m), 3.69 (3H, s), 4.48 S (1H, d, J=8.7 Hz), 4.68–4.90 (1H, br), 6.23–7.17 (8H, m)

Rf: 0.30 (Merck, Kieselgel™ 60F$_{254}$/chloroform:methanol=10:1)

The diastereomer B of the title compound was prepared by similar reaction (122 mg, yield: 50%).

Diastereomer B

High resolution FAB-MS (m/e, (C$_{30}$H$_{32}$F$_2$N$_2$O$_6$+H)$^+$): Anal. Calcd 568.2259 Anal. Found 568.2248

$^1$H-NMR (300 MHz, CDCl$_3$, δ ppm): 1.14 (6H, d, J=6.3 Hz), 1.43 (3H, d, J=6.6 Hz), 2.65 (3H, d, J=4.0 Hz), 3.22–3.24 (1H, m), 3.58–3.64 (1H, m), 3.70 (3H, s), 4.08–4.16 (1H, m), 4.46 (1H, d, J=9.0 Hz), 4.83 (1H, d, J=9.5 Hz), 6.23–7.12 (8H, m)

Rf: 0.30 (Merck, Kieselgel™ 60F$_{254}$/chloroform:methanol=10:1)

Example 2

(5R,6S,7S)-6-Carboxy-5-(2,2-difluoro-1,3-benzodioxol-5-yl)-7-{2-[1-(N-methylaminocarbonyl)ethyl]-4-methoxyohenyl}-2-N-isopropylaminocyclopenteno[1,2,b]pyridine Reactions similar to those in Example 1-(6) and Example 1-(7) using (5R,6S,7S)-6-tert-butoxycarbonyl-5-(2,2-difluoro-1,3-benzodioxol-5-yl)-7-[2-(1-ethoxycarbonylethyl)-4-methoxyphenyl]-2-N-isopropylaminocyclopenteno[1,2,b]pyridine obtained by the resolution in Example 1-(5) gave the title compound. The spectral data (NMR and MS) of the diastereomers A and B were the same as those obtained in Example 1.

Examples 3 to 6

Reactions similar to those in Example 1 using the intermediates obtained in Example 1 gave the following compounds.

Example 3

(5S,6R,7R)-6-Carboxy-5-(2,2-difluoro-1,3-benzodioxol-5-yl)-7-{2-[1-(N,N-dimethylaminocarbonyl)ethyl]-4-methoxyphenyl}-2-N-isopropylaminocyclopenteno[1,2,b]pyridine Diastereomer A $^1$H-NMR (300 MHz, CDCl$_3$, δ ppm): 1.10 (3H, d, J=6.3 Hz), 1.13 (3H, d, J=6.3 Hz), 1.44 (3H, d, J=6.7 Hz), 2.64 (3H, s), 2.82 (3H, s), 3.09 (1H, m), 3.60–3.71 (4H, m), 4.26 (1H, m), 4.38 (1H, d, J=8.2 Hz), 4.77 (1H, d, J=8.6 Hz), 6.60–6.72 (2H, m), 6.86–6.98 (4H, m), 7.03 (1H, d, J=8.6 Hz)

FAB-MS m/z 582 (M+H)$^+$

Rf: 0.32 (Merck, Kieselgel™ 60F$_{254}$/chloroform:methanol=9:1)

Diastereomer B $^1$H-NMR (300 MHz, CDCl$_3$, δ ppm): 1.08 (6H, d, J=6.3 Hz), 1.11 (3H, d, J=6.4 Hz), 1.29 (3H, d, J=6.6 Hz), 2.90 (3H, s), 2.93 (3H, s), 3.08 (1H, m), 3.64 (1H, m), 3.69 (3H, s), 4.18 (1H, m), 4.49 (1H, d, J=8.3 Hz), 4.90 (1H, d, J=8.6 Hz), 6.20 (1H, d, J=8.6 Hz), 6.69–6.99 (6H, m), 7.03 (1H, d, J=8.6 Hz)

FAB-MS m/z 582 (M+H)$^+$

Rf: 0.32 (Merck, Kieselgel™ 60F$_{254}$/chloroform:methanol=9:1)

Example 4

(5R,6S,7S)-6-Carboxy-5-(2,2-difluoro-1,3-benzodioxol-5-yl)-7-{2-[1-(N,N-dimethylaminocarbonyl)ethyl]-4-methoxyphenyl}-2-N-isopropylaminocyclopenteno[1,2,b]pyridine Diastereomer A and Diastereomer B The spectral data (NMR and MS) of the diastereomers A and B were the same as those in obtained in Example 3.

Example 5

(5S,6R,7R)-6-Carboxy-5-(2,2-difluoro-1,3-benzodioxol-5-yl)-7-[2-(N,N-dimethylaminocarbonylmethyl)-4-methoxyphenyl]-2-N-isopropylaminocyclopenteno[1,2,]pyridine $^1$H-NMR (300 MHz, CDCl$_3$, δ ppm): 1.13 (6H, d, J=6.3 Hz), 1.17 (3H, d, J=6.3 Hz), 2.90 (6H, s), 3.05 (1H, dd, J=9.9, 9.5 Hz), 3.68 (3H, s), 3.50–3.98 (3H, m), 6.27–7.12 (8H, m)

Rf: 0.35 (Merck, Kieselgel™ 60F$_{254}$/chloroform:methanol=10:1)

Example 6

(5R,6S,7S)-6-Carboxy-5-(2,2-difluoro-1,3-benzodioxol-5-yl)-7-[2-(N,N-dimethylaminocarbonylmethyl)-4-methoxyphenyl]-2-N-isopropylaminocyclopenteno[1,2,b]pyridine The spectral data (NMR and MS) of the diastereomers A and B were the same as those in obtained in Example 5.

Example 7

(5S,6R,7R)-6-Carboxy-7-[2-(1-carboxyethyl)-4-methoxyphenyl]-5-(2,2-difluoro-1,3-benzodioxol-5-yl)-2-N-isopropylaminocyclopenteno[1,2,b]pyridine Diastereomer A $^1$H-NMR (300 MHz, CDCl$_3$, δ ppm): 1.10 (3H, d, J=6.3 Hz), 1.15 (3H, d, J=6.4 Hz), 1.47 (3H, d, J=7.1 Hz), 3.09 (1H, m), 3.76 (4H, m), 4.21 (1H, m), 4.53 (1H, d, J=8.0 Hz), 4.87 (1H, m), 6.41 (1H, d, J=7.8 Hz), 6.75–7.18 (7H, m)

FAB-MS m/z 555 (M+H)$^+$

Rf: 0.11 (Merck, Kieselgel™ 60F$_{254}$/chloroform:methanol=9:1)

Diastereomer B $^1$H-NMR (300 MHz, CDCl$_3$, δ ppm): 1.14 (6H, d, J=6.3 Hz), 1.17 (3H, d, J=7.5 Hz), 1.40 (3H, brs), 3.25 (1H, m), 3.77 (4H, m), 4.20 (1H, m), 4.56 (1H, m), 5.09 (1H, m), 6.51 (1H, m), 6.78–6.92 (2H, m), 7.09–7.27 (5H, m)

FAB-MS m/z 555 (M+H)$^+$

Rf: 0.12 (Merck, Kieselgel™ 60F$_{254}$/chloroform:methanol=9:1)

Example 8

(5R,6S,7S)-6-Carboxy-7-[2-(1-carboxyethyl)-4-methoxyphenyl]-5-(2,2-difluoro-1,3-benzodioxol-5-yl)-2-N-isopropylaminocyclopenteno[1,2,b]pyridine Diastereomer A and Diastereomer B The spectral data (NMR and MS) of the diastereomers A and B were the same as those in obtained in Example 7.

Example 9

(5S,6R,7R)-6-Carboxy-7-[2-(1-carboxybutyl)-4-methoxyphenyl]-5-(2,2-difluoro-1,3-benzodioxol-5-yl)-2-N-isopropylaminocyclopenteno[1,2,b]pyridine Diastereomer A $^1$H-NMR (300 MHz, CD$_3$OD, δ ppm): 0.88 (3H, m), 1.15 (3H, m), 1.31 (2H, m), 1.61 (1H, m), 2.01 (1H, m), 3.25 (1H, m), 3.75 (4H, m), 4.08 (1H, m), 4.54 (1H, m), 5.15 (1H, m), 6.25–7.25 (2H, m)

FAB-MS m/z 583 (M+H)$^+$

Rf: 0:36 (Merck, Kieselgel™ 60F$_{254}$/chloroform:methanol=9:1)

Diastereomer B $^1$H-NMR (300 MHz, CD$_3$OD, δ ppm): 0.93 (3H, d, J=7.3 Hz), 1.10 (3H, d, J=6.3 Hz), 1.15 (3H, d, J=6.3 Hz), 1.39 (2H, m), 1.76 (1H, m), 2.03 (1H, m), 3.11 (1H, m), 3.69–3.84 (4H, m), 4.08 (1H, m), 4.54 (1H, d, J=7.6 Hz), 4.92 (1H, d, J=8.2 Hz), 6.43 (1H, d, J=8.6 Hz), 6.74–7.19 (7H, m)

FAB-MS m/z 583 (M+H)$^+$

Rf: 0.40 (Merck, Kieselgel™ 60F$_{254}$/chloroform:methanol=9:1)

Example 10

(5R,6S,7S)-6-Carboxy-7-[2-(1-carboxybutyl)-4-methoxyphenyl]-5-(2,2-difluoro-1,3-benzodioxol-5-yl)-2-N-isopropylaminocyclopenteno[1,2,b]pyridine Diastereomer A and Diastereomer B The spectral data (NMR and MS) of the diastereomers A and B were the same as those in obtained in Example 9.

Example 11

(5S,6R,7R)-6-Carboxy-5-(2,2-difluoro-1,3-benzodioxol-5-yl)-7-(2-hydroxymethyl-4-methoxyphenyl)-2-N-isopropylaminocyclopenteno[1,2,b]pyridine (1) (5RS,6SR,7SR)-6-tert-Butoxycarbonyl-5-(2,2-difluoro-1,3-benzodioxol-5-yl)-7-(2-hydroxymethyl-4-methoxyphenyl)cyclopenteno[1,2,b]pyridine To the compound obtained in Reference Example 1 (2.50 g, 3.97 mmol) in DMF (40 ml), tributylvinyltin (1.70 ml, 5.96 mmol), lithium chloride (526 mg, 12.4 mmol) and bis(triphenylphosphine)palladium chloride (286 mg, 0.41 mmol) were added, and the resulting reaction solution was stirred at 130° C. under heating for 1 hour and worked up. The resulting compound was dissolved in THF (20 ml)-H$_2$O (20 ml), and osmium tetroxide (0.05 M-H$_2$O, 1.6 ml) and N-methylmorpholine-N-oxide (650 mg, 5.55 mmol), were added. The resulting reaction solution was stirred overnight. The reaction mixture was worked up, the resulting diol was dissolved in THF (20 ml)-H$_2$O (20 ml), and the resulting reaction solution was mixed with sodium periodate (1.63 g, 7.62 mmol) at 0° C. and stirred for 30 minutes. The reaction solution was reduced by addition of sodium borohydride (1.2 g, 31.7 mmol), worked up and concentrated under reduced pressure. Purification of the resulting residue by silica gel chromatography (Wacogel™ C-300, hexane-ethyl acetate) gave the above-identified compound (700 mg, yield: 34%)

$^1$H-NMR (300 MHz, CDCl$_3$, δ ppm): 1.32 (9H, s), 3.58 (1H, dd, J=9.8, 9.4 Hz ), 3.81 (3H, s), 3.86 (1H, dd, J=9.2, 8.9 Hz), 4.62 (1H, d, J=9.9 Hz), 4.70 (1H, d, J=9.4 Hz), 4.93 (1H, d, J=9.9 Hz), 5.22 (1H, d, J=9.8 Hz), 6.81–7.10 (8H, m), 8.39 (1H, d, J=5.2 Hz)

(2) Reaction and optical resolution similar to that in Example 1 using (5RS,6SR,7SR)-6-tert-butoxycarbonyl-5-(2,2-difluoro-1,3-benzodioxol-5-yl)-7-(2-hydroxymethyl-4-methoxyphenyl)cyclopenteno[1,2,b]pyridine gave the title compound.

High resolution FAB-MS (m/e, (C$_{27}$H$_{27}$F$_2$N$_2$O$_6$+H)$^+$): Anal. Calcd 513.1837 Anal. Found 513.1812

$^1$H-NMR (300 MHz, CDCl$_3$, δ ppm): 1.24–1.28 (6H, m), 3.59–3.70 (1H, m), 3.76 (3H, s), 3.86 (1H, dd, J=9.2, 8.9 Hz), 4.60 (1H, d, J=9.2 Hz), 4.62 (1H, d, J=12.8 Hz), 4.98 (1H, d, J=12.8 Hz), 5.50 (1H, d, J=8.9 Hz), 6.55–7.41 (8H, m)

Rf: 0.35 (Merck, Kieselgel™ 60F$_{254}$/chloroform:methanol=15:1)

Examples 12 to 18

Reactions similar to those in Example 11 using the compound obtained in Reference Example 1 gave the following compounds.

Example 12

(5S,6R,7R)-6-Carboxy-5-(2,2-difluoro-1,3-benzodioxol-5-yl)-7-[2-(1-hydroxyethyl)-4-methoxyphenyl]-2-N-isopropylaminocyclopenteno[1,2,b]pyridine Diastereomer A High resolution FAB-MS m/e, (C$_{28}$H$_{29}$F$_2$N$_2$O$_6$+H)$^+$): Anal. Calcd 527.1994 Anal. Found 527.1977

$^1$H-NMR (300 MHz, CDCl$_3$, δ ppm): 1.25 (6H, d, J=5.5 Hz ), 1.43–1.49 (3H, br), 3.28–3.43 (1H, br), 3.58–3.68 (1H, m), 3.74 (3H, s), 4.60 (1H, br), 5.02 (1H, br), 5.72–5.90 (1H, br), 6.29–7.21 (8H, m)

Rf: 0.30 (Merck, Kieselgel™ 60F$_{254}$/chloroform:methanol=15:1)

Diastereomer B

High resolution FAB-MS m/e, (C$_{28}$H$_{29}$F$_2$N$_2$O$_6$+H)$^+$): Anal. Calcd 527.1994 Anal. Found 527.1987

$^1$H-NMR (300 MHz, CDCl$_3$, δ ppm): 1.10–1.13 (6H, m), 1.30–1.50 (3H, m), 3.11–3.23 (1H, br), 3.42–3.78 (1H, m), 3.63 (3H, s), 4.46 (1H, d, J=8.4 Hz), 4.90–5.01 (1H, br), 5.04–5.18 (1H, br), 6.29–7.21 (8H, m)

Rf: 0.30 (Merck, Kieseigel™ 60F$_{254}$/chloroform:methanol=15:1)

Example 13

(5R,6S,7S)-6-Carboxy-5-(2,2-difluoro-1,3-benzodioxol-5-yl)-7-[2-(1-hydroxyethyl)-4-methoxyphenyl]-2-N-isopropylaminocyclopenteno[1,2,b]pyridine Diastereomer A and Diastereomer B The spectral data (NMR and MS) of the diastereomers A and B were the same as those in obtained in Example 12.

Example 14

(5S,6R,7R)-6-Carboxy-5-(2,2-difluoro-1,3-benzodioxol-5-yl)-7-[2-(3-hydroxy-2-methylpropyl)-4-methoxyphenyl]-2-N-isopropylaminocyclopenteno[1,2,b]pyridine Diastereomer A High resolution FAB-MS (m/e, (C$_{30}$H$_{33}$F$_2$N$_2$O$_6$+H)$^+$): Anal. Calcd 555.2307 Anal. Found 555.2291

$^1$H-NMR (300 MHz, CDCl$_3$, δ ppm): 1.05 (3H, d, J=6.3 Hz), 1.10 (3H, d, J=6.3 Hz), 1.15 (3H, d, J=6.3 Hz), 1.98–2.10 (1H, m). 2.47–2.58 (1H, m), 2.98 (1H, dd, J=10.2, 10.0 Hz), 3.10–3.17 (1H, m), 3.31–3.50 (2H, m), 3.64 (1H, m), 3.78 (3H, s), 4.50 (1H, d, J=10.0 Hz), 5.06 (1H, d, J=10.2 Hz), 6.21 (1H, d, J=8.5 Hz), 6.68–7.02 (6H, m), 7.04 (1H, d, J=8.5 Hz)

Rf: 0.25 (Merck, Kieselgel™ 60F$_{254}$/ chloroform:methanol=10:1)

Diastereomer B

High resolution FAB-MS (m/e, (C$_{30}$H$_{33}$F$_2$N$_2$O$_6$+H)$^+$): Anal. Calcd 555.2307 Anal. Found 555.2280

$^1$H-NMR (300 MHz, CDCl$_3$, δ ppm): 0.90 (3H, d, J=6.9 Hz), 1.13 (3H, d, J=6.9 Hz), 1.15 (3H, d, J=6.5 Hz), 1.84–2.00 (1H, m), 2.42–2.59 (1H, m), 2.62–2.68 (1H, m), 3.06 (1H, d, J=9.2, 8.8 Hz), 3.27–3.48 (2H, m), 3.59–3.70 (1H, m), 3.71 (3H, s), 4.46 (1H, m), 4.87 (1H, d, J=9.2 Hz), 6.20–7.10 (8H, m)

Rf: 0.25 (Merck, Kieselgel™ 60F$_{254}$/ chloroform:methanol=10:1)

Example 15

(5R,6S,7S)-6-Carboxy-5-(2,2-difluoro-1,3-benzodioxol-5-yl)-7-[2-(3-hydroxy-2-methylpropyl)-4-methoxyphenyl]-2-N-isopropylaminocyclopenteno[1,2,b]pyridine Diastereomer A and Diastereomer B The spectral data (NPE and MS) of the diastereomers A and B were the same as those in obtained in Example 14.

Example 16

(5S,6R,7R)-6-Carboxy-5-(2,2-difluoro-1,3-benzodioxol-5-yl)-7-[2-(1-carboxyethyl)-4-methoxophenyl]-2-butylcyclopenteno[1,2,b]pyridine Diastereomer A $^1$H-NMR (300 MHz, CDCl$_3$, δ ppm): 0.89 (3H, t, J=7.3 Hz), 1.27–1.35 (2H, m), 1.52 (3H, d, J=6.3 Hz), 1.51–1.56 (2H, m), 2.72 (2H, t, J=7.5 Hz), 3.80 (3H, s), 3.83 (1H, dd, J=9.3, 9.8 Hz), 4.70 (1H, d, J=9.3 Hz), 5.11 (1H, d, J=9.8 Hz), 6.80–7.32 (8H, m)

Diastereomer B $^1$H-NMR (300 MHz, CDCl$_3$, δ ppm): 0.87 (3H, t, J=7.3 Hz), 1.26–1.33 (2H, m), 1.53–1.64 (2H, m), 1.63 (3H, d, J=6.9 Hz), 2.69 (2H, t, J=7.5 Hz), 3.26 (1H, dd, J=9.4, 10.0 Hz), 3.77 (3H, s), 4.30–4.44 (1H, br), 4.56 (1H, d, J=9.4 Hz), 5.13 (1H, d, J=9.8 Hz), 6.76–7.28 (8H, m)

Example 17

(5S,6R,7R)-6-Carboxy-5-(2,2-difluoro-1,3-benzodioxol-5-yl)-7-[2-(1-carboxybutyl)-4-methoxyphenyl]-2-butylcyclopenteno[1,2,b]pyridine Diastereomer A $^1$H-NMR (300 MHz, CDCl$_3$, δ ppm) 0.81 (3H, t, J=7.2 Hz), 0.87 (3H, t, J=7.3 Hz), 1.24–2.21 (8H, m), 2.72 (2H, t, J=7.5 Hz), 3.78 (3H, s), 3.83 (1H, dd, J=9.5, 9.9 Hz), 4.01–4.03 (1H, m), 4.69 (1H, d, J=9.5 Hz), 5.12 (1H, d, J=9.9 Hz), 6.78–7.32 (8H, m)

Diastereomer B $^1$H-NMR (300 MHz, CDCl$_3$, δ ppm) 0.82–1.00 (6H, br), 1.23–2.00 (8H, m), 2.63–2.80 (2H, m), 3.15–3.32 (1H, m), 3.64–3.82 (3H, m), 4.13–4.40 (1H, m), 4.50–4.62 (1H, m), 4.98–5.16 (1H, m), 6.72–7.20 (8H, m)

Example 18

(5S,6R,7R)-6-Carboxy-5-(2,2-difuluoro-1,3-benzodioxol-5-yl)-7-[2-(2-carboxypropyl)-4-methoxyphenyl]-2-isopropylamino[1,2,b]pyridine Diastereomer A $^1$H-NMR (300 MHz, CDCl$_3$, δ ppm): 1.13–1.36 (9H, m), 2.51–3.22 (4H, m), 3.62–3.70 (1H, m), 3.71 (3H, s), 4.58 (1H, d, J=9.0 Hz), 5.12–5.30 (1H, br), 6.48–7.61 (8H, m).

FAB-MS m/z 569 (M+H)$^+$

Reference Example 1

(5RS,6SR,7SR)-6-tert-Butoxycarbonyl-5-(2,2-difluoro-1,3-benzodioxol-5-yl)-7-(4-methoxy-2-trifluoromethanesufonyloxyphenyl)cyclopenteno[1,2,b]pyridine (1) 7-(2-Benzyloxy-4-methoxyphenyl)-6-tert-butoxycarbonyl-5-(2,2-difluoro-1,3-benzodioxol-5-yl)-5-hydroxycyclopenta-1,3-dieno[1,2,b]pyridine To 7-(2-benzyloxy-4-methoxyphenyl)-6-tert-butoxycarbonyl-5-oxocyclopenta-1,3-dieno[1,2,b]pyridine (compound disclosed in WO9505374A1; 70.0 g, 0.158 mol) in THF (1.24 L), 2,2-difluoro-1,3-benzodioxol-5-ylmagnesium bromide (0.316 mol) in THF was added dropwise in a stream of nitrogen at −78° C. After addition of saturated NH$_4$Cl solution at −78° C., the reaction solution was warmed to room temperature and extracted with ethyl acetate. The organic layer was washed with saturated aqueous sodium chloride and dried over MgSO$_4$, and the solvent was distilled away under reduced pressure. Isopropyl ether was added to the resulting residue, and the resulting pale yellow powder was filtered off and dried to give the above-identified compound (91.5 g, yield: 96%).

$^1$H-NMR (300 MHz, CDCl$_3$, δ ppm): 1.19 (9H, s), 3.87 (3H, s), 4.45 (1H, s), 5.04 (2H, s), 6.67–8.53 (14H, m)

(2) 5-Acetoxy-7-(2-benzyloxy-4-methoxyphenyl)-6-tert-butoxycarbonyl-5-(2,2-difluoro-1,3-benzodioxol-5-yl) cyclopenta-1,3-dieno[1,2,b]pyridine To 7-(2-benzyloxy-4-methoxyphenyl)-6-tert-butoxycarbonyl-5-(2,2-difluoro-1,3-benzodioxol-5-yl)-5-hydroxycycloenta-1,3-dieno[1,2,b]pyridine (90 g, 0.15 mol) in chloroform (800 ml), DMAP (73 g, 0.60 mol) and acetic anhydride (31 g, 0.30 mol) were added, and the resulting reaction solution was stirred in a stream of nitrogen under reflux for 2 hours. The reaction solution was concentrated under reduced pressure, and ethyl acetate (500 ml) and hexane (1 L) were added to the residue. The organic layer was washed with 1N hydrochloric acid, saturated aqueous NaHCO$_3$ and saturated aqueous sodium chloride successively, dried over MgSO$_4$ and concentrated under reduced pressure to give the above-identified compound (96 g, yield: 100%).

$^1$H-NMR (300 MHz, CDCl$_3$, δ ppm): 1.18 (9H, s), 2.18 (3H, s), 3.86 (3H, s), 5.04 (2H, s), 6.65–8.56 (14H, m)

(3) (5RS,6RS,7SR)-6-tert-Butoxycarbonyl-5-(2,2-difluoro-1,3-benzodioxol-5-yl)-7-(2-hydroxy-4-methoxyphenyl)cyclopenteno[1,2,b]pyridine 5-Acetoxy-7-(2-benzyloxy-4-methoxyphenyl)-6-tert-butoxycarbonyl-5-(2,2-difluoro-1,3-benzodioxol-5-yl) cyclopenta-1,3-dieno[1,2,b]pyridine (96.0 g, 0.15 mol) in a mixture of THF (700 ml)-methanol (350 ml) was stirred with 10% Pd—C (100 g) in a stream of hydrogen at ordinary pressure at room temperature for 2 days. The reaction mixture was filtered through celite for removal of the catalyst, and the filtrate was concentrated under reduced pressure. Isopropyl ether was added to the residue, and the precipitate was filtered off and dried to give the above-identified compound (50.5 g, yield: 68%) as a white powder.

$^1$H-NMR (300 MHz, CDCl$_3$, δ ppm): 0.91 (9H, s), 3.74 (3H, s), 3.97 (1H, t, J=6.8 Hz), 4.81 (1H, d, J=6.8 Hz), 5.03 (1H, d, J=6.8 Hz), 6.35–8.40 (9H, m)

(4) (5RS,6SR,7SR)-6-tert-Butoxycarbonyl-5-(2,2-difluoro-1,3-benzodioxol-5-yl)-7-(2-hydroxy-4-methoxyphenyl)cyclopenteno[1,2,b]pyridine (5RS,6RS,7SR)-6-tert-Butoxycarbonyl-5-(2,2-difluoro-1,3-benzodioxol-5-yl)-7-(2-hydroxy-4-methoxyphenyl)cyclopenteno[1,2,b]pyridine (49.0 g, 98.5 mmol) in a mixture of THF (500 ml) and tert-butanol (250 ml) was stirred with potassium tert-butoxide (24.3 g, 217 mmol) under a stream of nitrogen at room temperature for 30 minutes. The reaction solution was mixed with saturated aqueous $NH_4Cl$ and extracted with ethyl acetate. The organic layer was washed with saturated aqueous sodium chloride, dried over $MgSO_4$ and concentrated under reduced pressure to give the above-identified compound, which was directly used for the next reaction without purification.

$^1$H-NMR (300 MHz, $CDCl_3$, δ ppm): 1.27 (9H, s), 3.55 (1H, dd, J=10.3, 9.2 Hz), 3.77 (3H, s), 4.64 (1H, d, J=9.2 Hz), 5.03 (1H, d, J=10.3 Hz), 6.42–8.42 (9H, m)

(5) To (5RS,6SR,7SR)-6-tert-butoxycarbonyl-5-(2,2-difluoro-1,3-benzodioxol-5-yl)-7-(2-hydroxy-4-methoxyphenyl)cyclopenteno[1,2,b]pyridine (49.0 g) in chloroform (500 ml), DMAP (44.2 g, 394 mmol) and trifluoromethanesulfonic anhydride (21.5 ml, 128 mmol) were added under cooling with ice, and the resulting reaction mixture was stirred at the same temperature for 30 minutes. Hexane (2 L) was added to the reaction mixture, and the organic layer was washed with 1N hydrochloric acid, saturated aqueous $NaHCO_3$ and saturated aqueous sodium chloride successively, dried over $MgSO_4$ and concentrated under reduced pressure. Purification of the resulting residue by silica gel chromatography (hexane-ethyl acetate) gave the title compound (42.3 g, yield: 68%).

$^1$H-NMR (300 MHz, $CDCl_3$, δ ppm): 1.35 (9H, s), 3.24 (1H, dd, J=10.5, 9.8 Hz), 3.77 (3H, s), 4.69 (1H, d, J=9.8 Hz), 4.86 (1H, d, J=10.5 Hz), 6.89–8.49 (9H, m)

INDUSTRIAL APPLICABILITY

The compounds of the present invention have a strong affinity selectively for endothelin receptor subtypes and are useful as vasodilators and bronchodilators in the field of medicines. They exert the effect of relaxing smooth muscle such as a vasodilator effect and a bronchodilator effect by inhibiting the binding of endothelin and can be used in the field of medicines, as drugs for treating one or more diseases selected from the group consisting of hypertension, pulmonary hypertension, Raynaud's disease, acute renal failure, heart failure, myocardial infarction, angina pectoris, cerebral infarction, cerebral vasospasm, arteriosclerosis, asthma, gastric ulcer, diabetes, restenosis, prostatism, endotoxin shock, endotoxin-induced multiple organ failure, disseminated intravascular coagulation and cyclosporin-induced renal failure and hypertension.

What is claimed is:
1. A compound represented by formula [I] or a pharmaceutically acceptable salt thereof:

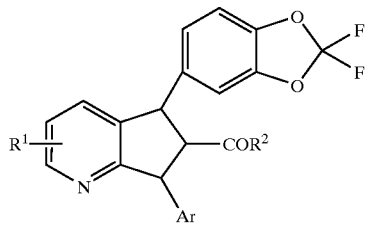

[I]

wherein Ar is a phenyl group, a thienyl group or a pyridyl group which may have one to three substituents selected from the group consisting of hydroxyl groups, amino groups, carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups, $R^1$ is a hydrogen atom, a hydroxyl group, a cyano group, a nitro group, a carboxyl group, an amino group, a halogen atom, a $C_1$–$C_6$ alkyl group, a $C_3$–$C_8$ cycloalkyl group, a $C_3$–$C_8$ cycloalkyl $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkylthio group, a formyl group, a $C_2$–$C_6$ alkanoyl group, an aroyl group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl)amino group, a $C_2$–$C_6$ alkanoylamino group, an aroylamino group, an N—($C_1$–$C_6$ alkyl)-N-(aroyl)amino group, a $C_1$–$C_6$ alkylsulfonylamino group, an aryl $C_1$–$C_6$ alkylamino group, an N-(aryl $C_1$–$C_6$ alkyl)-N-(aroyl)amino group, an arylsulfonylamino group, an aryl $C_1$–$C_6$ alkylsulfonylamino group, a $C_4$–$C_7$ cyclic imino group or a $C_1$–$C_6$ alkoxycarbonyl group, and $R^2$ is a hydroxyl group, an amino group, a $C_1$–$C_6$ alkoxy group, a mono- or di-$C_1$–$C_6$ alkylamino group, a $C_1$–$C_6$ alkylsulfonylamino group or an arylsulfonylamino or an aryl $C_1$–$C_6$ alkylsulfonylamino group which may have a $C_1$–$C_6$ alkyl group.

2. The compound according to claim 1, which is represented by formula [I-a] or a pharmaceutically acceptable salt thereof:

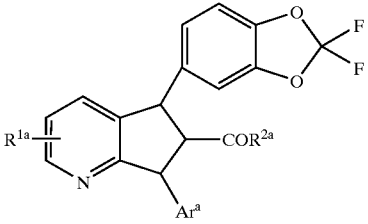

[I-a]

wherein $Ar^a$ is a phenyl group or a pyridyl group which may have one to three substituents selected from the group consisting of hydroxyl groups, amino groups, carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups, $R^{1a}$ is a hydroxyl group, an amino group, a $C_1$–$C_6$ alkyl group, a $C_3$–$C_8$ cycloalkyl group, a $C_3$–$C_8$ cycloalkyl $C_1$–$C_6$ alkyl group, a $C_2$–$C_6$ alkenyl group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl)amino group, an aroylamino group, a $C_1$–$C_6$ alkylsulfonylamino group or a $C_4$–$C_7$ cyclic imino group, and $R^{2a}$ is a hydroxyl group, a $C_1$–$C_6$ alkoxy group, a $C_1$–$C_6$ alkylsulfonylamino group or an arylsulfonylamino group which may have a $C_1$–$C_6$ alkyl group.

3. The compound according to claim 1, which is represented by formula [I-b] or a pharmaceutically acceptable salt thereof:

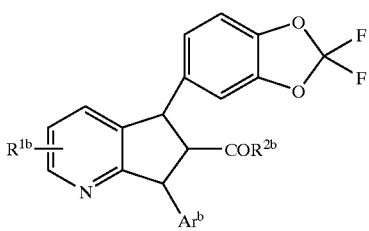

[I-b]

herein $Ar^b$ is a phenyl group which may have one to three substituents selected from the group consisting of hydroxyl groups, amino groups, carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups, $R^{1b}$ is a $C_1$–$C_6$ alkyl group, a mono- or di-$C_1$–$C_6$ alkylamino group, an aroylamino group or a $C_1$–$C_6$ alkylsulfonylamino group, and $R^{2b}$ is a hydroxyl group or an arylsulfonylamino group which may have a $C_1$–$C_6$ alkyl group.

4. The compound according to claim 1, which is represented by formula [I-c] or a pharmaceutically acceptable salt thereof:

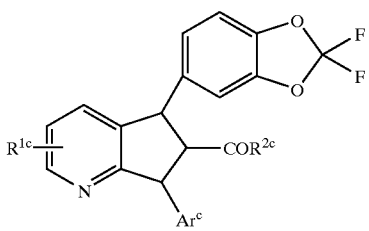

[I-c]

wherein $Ar^c$ is a phenyl group, a thienyl group or a pyridyl group which may have one to three substituents selected from the group consisting of hydroxyl groups, amino groups, carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups, $R^{1c}$ is an amino group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl) amino group, a $C_2$–$C_6$ alkanoylamino group, an aroylamino group, an N—($C_1$–$C_6$ alkyl)-N-(aroyl)amino group, a $C_1$–$C_6$ alkylsulfonylamino group, an aryl $C_1$–$C_6$ alkylamino group, an N-(aryl $C_1$–$C_6$ alkyl)-N-(aroyl)amino group, an arylsulfonylamino group, an aryl $C_1$–$C_6$ alkylsulfonylamino group or a $C_4$–$C_7$ cyclic imino group, and $R^{2c}$ is a hydroxyl group, an amino group, a $C_1$–$C_6$ alkoxy group, a mono- or di-$C_1$–$C_6$ alkylamino group, a $C_1$–$C_6$ alkylsulfonylamino group or an arylsulfonylamino or an aryl $C_1$–$C_6$ alkylsulfonylamino group which may have a $C_1$–$C_6$ alkyl group.

5. The compound according to claim 1, wherein said compound is selected from the group consisting of (5S,6R, 7R)-2-amino-carboxy-5-(2,2-difluoro-1,3-benzodioxol-5-yl)-7-[2-(3-hydroxy-2-methylpropyl)-4-methoxyphenyl] cyclopenteno[1,2,b]pyridine, (5S,6R,7R)-6-carboxy-5-(2,2-difluoro-1,3-benzodioxol-5-yl)-7-(2-propyl-4-methoxyphenyl)-2-(methanesulfonylamino)cyclopenteno[1,2,b]pyridine, (5S,6R,7R)-6-carboxy-5-(2,2-difluoro-1,3-benzodioxol-5-yl)-7-[2-(3-hydroxy-2-methylpropyl)-4-methoxyphenyl]-2-(methanesulfonylamino)cyclopenteno[1,2,b]pyridine, (5S,6R,7R)-6-carboxy-5-(2,2-difluoro-1,3-benzodioxol-5-yl)-7-[2-(3-hydroxy-2-methylpropyl)-4-methoxyphenyl]-2-N-propylaminocyclopenteno[1,2,b]pyridine, (5S,6R,7R)-6-carboxy-5-(2,2-difluoro-1,3-benzodioxol-5-yl)-7-(2-propyl-4-methoxyphenyl)-2-N-isopropylaminocyclopenteno[1,2,b]pyridine, (5S,6R,7R)-6-carboxy-5-(2,2-difluoro-1,3-benzodioxol-5-yl)-7-(2-hydroxymethyl-4-methoxyphenyl)-2-N-isopropylaminocyclopenteno[1,2,b]pyridine, (5S,6R,7R)-6-carboxy-5-(2,2-difluoro-1,3-benzodioxol-5-yl)-7-[2-(1-hydroxyethyl)-4-methoxyphenyl]-2-N-isopropylaminocyclopenteno[1,2,b]pyridine, (5S,6R,7R)-6-carboxy-5-(2,2-difluoro-1,3-benzodioxol-5-yl)-7-[2-(2-hydroxy-2-methylpropyl)-4-methoxyphenyl]-2-N-isopropylaminocyclopenteno[1,2,b]pyridine, (5S,6R,7R)-6-carboxy-5-(2,2-difluoro-1,3-benzodioxol-5-yl)-7-[2-(3-hydroxy-2-methylpropyl)-4-methoxyphenyl]-2-N-isopropylaminocyclopenteno[1,2,b]pyridine, (5S,6R,7R)-6-carboxy-5-(2,2-difluoro-1,3-benzodioxol-5-yl)-7-[2-(3-hydroxy-2-methylpropoxy)-4-methoxyphenyl]-2-N-isopropylaminocyclopenteno[1,2,b]pyridine, (5S,6R,7R)-6-carboxy-7-[2-(1-carboxyethyl)-4-methoxyphenyl]-5-(2,2-difluoro-1,3-benzodioxol-5-yl)-2-N-isopropylaminocyclopenteno[1,2,b]pyridine, (5S,6R,7R)-6-carboxy-7-[2-(1-carboxybutyl)-4-methoxyphenyl]-5-(2,2-difluoro-1,3-benzodioxol-5-yl)-2-N-isopropylaminocyclopenteno[1,2,b]pyridine, (5S,6R,7R)-6-carboxy-7-[2-(2-carboxypropyl)-4-methoxyphenyl]-5-(2,2-difluoro-1,3-benzodioxol-5-yl)-2-N-isopropylaminocyclopenteno[1,2,b]pyridine, (5S,6R,7R)-6-carboxy-5-(2,2-difluoro-1,3-benzodioxol-5-yl)-7-[2-(1-carbamoylethyl)-4-methoxyphenyl]-2-N-isopropylaminocyclopenteno[1,2,b]pyridine, (5S,6R,7R)-6-carboxy-5-(2,2-difluoro-1,3-benzodioxol-5-yl)-7-{2-[1-(N-methylaminocarbonyl)ethyl]-4-methoxyphenyl}-2-N-isopropylaminocyclopenteno[1,2,b]pyridine, (5S,6R,7R)-6-carboxy-5-(2,2-difluoro-1,3-benzodioxol-5-yl)-7-{2-[1-(N,N-dimethylaminocarbonyl)ethyl]-4-methoxyphenyl}-2-N-isopropylaminocyclopenteno[1,2,b]pyridine, (5S,6R,7R)-6-carboxy-5-(2,2-difluoro-1,3-benzodioxol-5-yl)-7-[2-(3-hydroxy-2-methylpropoxy)phenyl]-2-N-isopropylaminocyclopenteno[1,2,b]pyridine, (5S,6R,7R)-6-carboxy-5-(2,2-difluoro-1,3-benzodioxol-5-yl)-7-[2-(3-hydroxy-2-methylpropoxy)-4-fluorophenyl]-2-N-isopropylaminocyclopenteno[1,2,b]pyridine, (5S,6R,7R)-6-carboxy-5-(2,2-difluoro-1,3-benzodioxol-5-yl)-7-(2-hydroxymethyl-4-methoxyphenyl)-2-N-butylaminocyclopenteno[1,2,b]pyridine, (5S,6R,7R)-6-carboxy-5-(2,2-difluoro-1,3-benzodioxol-5-yl)-7-[2-(3-hydroxy-2-methylpropyl)-4-methoxyphenyl]-2-N-butylaminocyclopenteno[1,2,b]pyridine, (5S,6R,7R)-6-carboxy-5-(2,2-difluoro-1,3-benzodioxol-5-yl)-7-[2-(3-hydroxy-2-methylpropoxy)-4-methoxyphenyl]-2-N-butylaminocyclopenteno[1,2,b]pyridine, (5S,6R,7R)-6-carboxy-7-[2-(1-carboxyethyl)-4-methoxyphenyl]-5-(2,2-difluoro-1,3-benzodioxol-5-yl)-2-propylaminocyclopenteno[1,2,b]pyridine, (5S ,6R,7R)-6-carboxy-7-[2-(1-carboxyethyl)-4-methoxyphenyl]-5-(2,2-difluoro-1,3-benzodioxol-5-yl)-2-butylcyclopenteno[1,2,b]pyridine, (5S, 6R,7R)-6-carboxy-7-[2-(1-carboxybutyl)-4-methoxyphenyl]-5-(2,2-difluoro-1,3-benzodioxol-5-yl)-2-butylcyclopenteno[1,2,b]pyridine, (5S,6R,7R)-6-carboxy-5-(2,2-difluoro-1,3-benzodioxol-5-yl)-7-{2-[1-(N,N-dimethylaminocarbonyl)ethyl]-4-methoxyphenyl}-2-butylcyclopenteno[1,2,b]pyridine and (5S,6R,7R)-5-(2,2-difluoro-1,3-benzodioxol-5-yl)-7-{2-[1(N,N-dimethylaminocarbonyl)ethyl]-4-methoxyphenyl}-2-N-isopropylamino-6-methanesulfonylaminocarbonylcyclopenteno[1,2,b]pyridine, or a pharmaceutically acceptable salt thereof.

6. The compound according to claim 1, wherein said compound is selected from the group consisting of (5S,6R,7R)-6-carboxy-5(2,2-difluoro-1,3-benzodioxol-5-yl)-7-(2-propyl-4-methoxyphenyl)-2-(methanesulfonylamino)cyclopenteno[1,2,b]pyridine, (5S,6R,7R)-6-carboxy-5-(2,2-difluoro-1,3-benzodioxol-5-yl)-7-[2-(3-hydroxy-2-methylpropyl)-4-methoxyphenyl]-2-N-isopropylaminocyclopenteno[1,2,b]pyridine, (5S,6R,7R)-6-carboxy-7-[2-(1-carboxyethyl)-4-methoxyphenyl]-5-(2,2-difluoro-1,3-benzodioxol-5-yl)-2-N-isopropylaminocyclopenteno[1,2,b]pyridine, (5S,6R,7R)-6-carboxy-7-[2-(1-carboxybutyl)-4-methoxyphenyl]-5-(2,2-difluoro-1,3-benzodioxol-5-yl)-2-N-isopropylaminocyclopenteno[1,2,b]pyridine, (5S,6R,7R)-6-carboxy-5-(2,2-difluoro-1,3-benzodioxol-5-yl)-7-{2-[1-(N,N-dimethylaminocarbonyl)ethyl]-4-methoxyphenyl)-2-N-isopropylaminocyclopenteno[1,2,b]pyridine, (5S,6R,7R)-6-carboxy-5-(2,2-difluoro-1,3-benzodioxol-5-yl)-7-[2-(3-hydroxy-2-methylpropyl)phenyl]-2-N-isopropylaminocyclopenteno[1,2,b]pyridine, (5S,6R,7R)-6-carboxy-7-[2-(1-carboxyethyl)-4-methoxyphenyl]-5-(2,2-difluoro-1,3-benzodioxol-5-yl)-2-propylcyclopenteno[1,2,b]pyridine and (5S,6R,7R)-6-carboxy-7-[2-(1-carboxyethyl)-4-methoxyphenyl)-5-(2,2-difluoro-1,3-benzodioxol-5-yl)-2-butylcyclopenteno[1,2,b]pyridine, or a pharmaceutically acceptable salt thereof.

7. The compound according to claim 1, wherein said compound is (5S,6R,7R)-6-carboxy-5(2,2-difluoro-1,3-benzodioxol-5-yl)-7-[2-(3-hydroxy-2-methylpropyl)-4-methoxyphenyl]-2-N-isopropylaminocyclopenteno[1,2,b]pyridine or a pharmaceutically acceptable salt thereof.

8. A process for producing a compound represented by formula [I] or a pharmaceutically acceptable salt thereof:

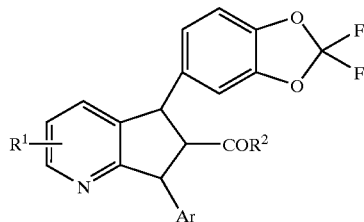

[I]

wherein Ar is a phenyl group, a thienyl group or a pyridyl group which may have one to three substituents selected from the group consisting of hydroxyl groups, amino groups, carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups, $R^1$ is a hydrogen atom, a hydroxyl group, a cyano group, a nitro group, a carboxyl group, an amino group, a halogen atom, a $C_1$–$C_6$ alkyl group, a $C_3$–$C_8$ cycloalkyl group, a $C_3$–$C_8$ cycloalkyl $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkylthio group, a formyl group, a $C_2$–$C_6$ alkanoyl group, an aroyl group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl)amino group, a $C_2$–$C_6$ alkanoylamino group, an aroylamino group, an N—($C_1$–$C_6$ alkyl)-N-(aroyl)amino group, a $C_1$–$C_6$ alkylsulfonylamino group, an aryl $C_1$–$C_6$ alkylamino group, an N-(aryl $C_1$–$C_6$ alkyl)-N-(aroyl)amino group, an arylsulfonylamino group, an aryl $C_1$–$C_6$ alkylsulfonylamino group, a $C_4$–$C_7$ cyclic imino group or a $C_1$–$C_6$ alkoxycarbonyl group, and $R^2$ is a hydroxyl group, an amino group, a $C_1$–$C_6$ alkoxy group, a mono- or di-$C_1$–$C_6$ alkylamino group, a $C_1$–$C_6$ alkylsulfonylamino group or an arylsulfonylamino or an aryl $C_1$–$C_6$ alkylsulfonylamino group which may have a $C_1$–$C_6$ alkyl group, which comprises reacting a compound represented by formula [II]:

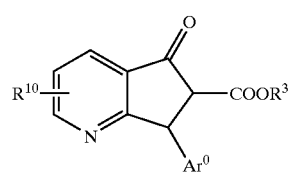

[II]

wherein $Ar^0$ is a phenyl group, a thienyl group or a pyridyl group which may have one to three substituents selected from the group consisting of optionally protected hydroxyl groups, optionally protected amino groups, optionally protected carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups, $R^3$ is a $C_2$–$C_6$ alkyl group, and $R^{10}$ is a hydrogen atom, an optionally protected hydroxyl group, a cyano group, a nitro group, an optionally protected carboxyl group, an optionally protected amino group, a halogen atom, a $C_1$–$C_6$ alkyl group, a $C_3$–$C_8$ cycloalkyl group, a $C_3$–$C_8$ cycloalkyl $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkylthio group, a formyl group, a $C_2$–$C_6$ alkanoyl group, an aroyl group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl)amino group, a $C_2$–$C_6$ alkanoylamino group, an aroylamino group, an N—($C_1$–$C_6$ alkyl)-N-(aroyl)amino group, a $C_1$–$C_6$ alkylsulfonylamino group, an aryl $C_1$–$C_6$ alkylamino group, an N-(aryl $C_1$–$C_6$ alkyl)-N-(aroyl)amino group, an arylsulfonylamino group, an aryl $C_1$–$C_6$ alkylsulfonylamino group, a $C_4$–$C_7$ cyclic imino group or a $C_1$–$C_6$ alkoxycarbonyl group, with an organic metal compound represented by formula [III]:

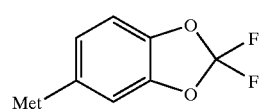

[III]

wherein Met is a metal atom, to obtain a compound represented by formula [IV]:

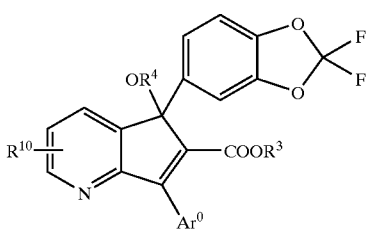

wherein $R^4$ is a hydrogen atom or a $C_1$–$C_6$ alkylcarbonyl group, and $Ar^0$, $R^3$ and $R^{10}$ are the same as defined above, reducing the compound represented by formula [IV] to obtain a compound represented by formula [V]:

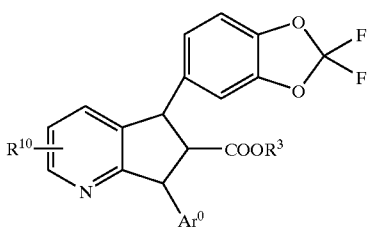

wherein $Ar^0$, $R^3$ and $R^{10}$ are the same as defined above, and if necessary, subjecting the compound represented by formula [V] to desired synthetically equivalent conversion of a functional group and/or removal of a protecting group, or conversion into a pharmaceutically acceptable salt thereof.

9. A process for producing a compound represented by formula [I] or a pharmaceutically acceptable salt thereof:

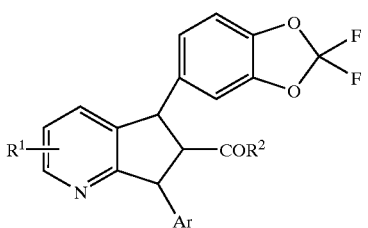

wherein Ar is a phenyl group, a thienyl group or a pyridyl group which may have one to three substituents selected from the group consisting of hydroxyl groups, amino groups, carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups, $R^1$ is a hydrogen atom, a hydroxyl group, a cyano group, a nitro group, a carboxyl group, an amino group, a halogen atom, a $C_1$–$C_6$ alkyl group, a $C_3$–$C_8$ cycloalkyl group, a $C_3$–$C_8$ cycloalkyl $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkylthio group, a formyl group, a $C_2$–$C_6$ alkanoyl group, an aroyl group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl)amino group, a $C_2$–$C_6$ alkanoylamino group, an aroylamino group, an N—($C_1$–$C_6$ alkyl)-N-(aroyl)amino group, a $C_1$–$C_6$ alkylsulfonylamino group, an aryl $C_1$–$C_6$ alkylamino group, an N-(aryl $C_1$–$C_6$ alkyl)-N-(aroyl)amino group, an arylsulfonylamino group, an aryl $C_1$–$C_6$ alkylsulfonylamino group, a $C_4$–$C_7$ cyclic imino group or a $C_1$–$C_6$ alkoxycarbonyl group, and $R^2$ is a hydroxyl group, an amino group, a $C_1$–$C_6$ alkoxy group, a mono- or di-$C_1$–$C_6$ alkylamino group, a $C_1$–$C_6$ alkylsulfonylamino group or an arylsulfonylamino or an aryl $C_1$–$C_6$ alkylsulfonylamino group which may have a $C_1$–$C_6$ alkyl group, which comprises reacting a compound represented by formula [VI]:

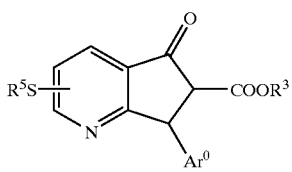

wherein $Ar^0$ is a phenyl group, a thienyl group or a pyridyl group which may have one to three substituents selected from the group consisting of optionally protected hydroxyl groups, optionally protected amino groups, optionally protected carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups, $R^3$ is a $C_1$–$C_6$ alkyl group, and $R^5$ is a $C_1$–$C_6$ alkyl group or an aryl group, with an organic metal compound represented by formula [III]:

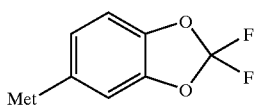

wherein Met is a metal atom, to obtain a compound represented by formula [VII]:

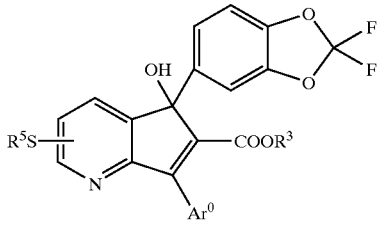

wherein $Ar^0$, $R^3$ and $R^5$ are the same as defined above, then protecting the hydroxyl group of the compound represented by formula [VII] to obtain a compound represented by formula [VIII]:

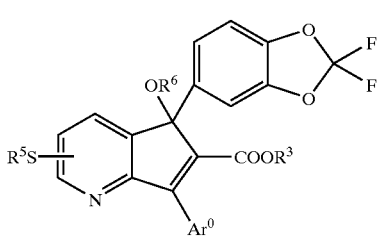

wherein $R^6$ is a hydroxyl-protecting group, and $Ar^0$, $R^3$ and $R^5$ are the same as defined above, further reacting the compound represented by formula [VIII] with an oxidizing agent to obtain a compound represented by formula [IX]:

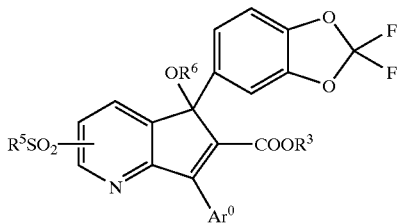

[IX]

wherein $Ar^0$, $R^3$ $R^5$ and $R^6$ are the same as defined above, reacting the compound represented by formula [IX] with a compound represented by formula [X]:

$$R^{10}\text{-Met} \qquad [X]$$

wherein $R^{10}$ is a hydrogen atom, an optionally protected hydroxyl group, a cyano group, a carboxyl group, an optionally protected amino group, a $C_1$–$C_6$ alkyl group, a $C_3$–$C_8$ cycloalkyl group, a $C_3$–$C_8$ cycloalkyl $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkylthio group, a formyl group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl)amino group, a $C_2$–$C_6$ alkanoylamino group, an aroylamino group, an N—($C_1$–$C_6$ alkyl)-N-(aroyl)amino group, a $C_4$–$C_7$ cyclic imino group or a $C_1$–$C_6$ alkoxycarbonyl group, and Met is the same as defined above, to obtain a compound represented by formula [XI]:

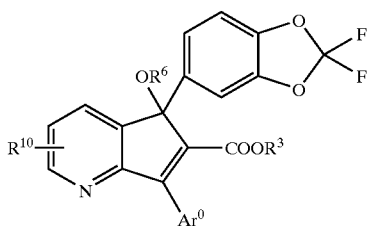

[XI]

wherein $Ar^0$, $R^3$, $R^6$ and $R^{10}$ are the same as defined above, then reducing the compound represented by formula [XI] to obtain a compound represented by formula [V]:

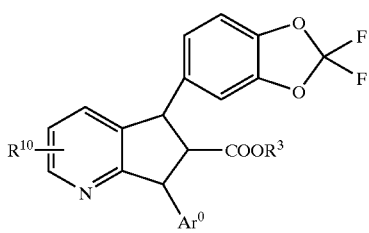

[V]

wherein $Ar^0$, $R^3$ and $R^{10}$ are the same as defined above, and if necessary, subjecting the compound represented by formula [V] to desired synthetically equivalent conversion of a functional group and/or removal of a protecting group, or conversion into a pharmaceutically acceptable salt thereof.

10. A process for producing a compound represented by formula [I-c] or a pharmaceutically acceptable salt thereof:

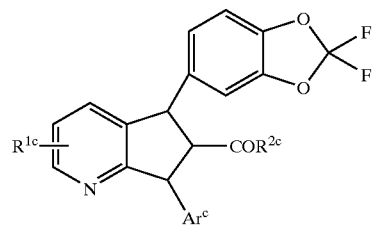

[I-c]

wherein $Ar^c$ is a phenyl group, a thienyl group or a pyridyl group which may have one to three substituents selected from the group consisting of hydroxyl groups, amino groups, carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups, $R^{1c}$ is an amino group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl) amino group, a $C_2$–$C_6$ alkanoylamino group, an aroylamino group, an N—($C_1$–$C_6$ alkyl)-N-(aroyl)amino group, a $C_1$–$C_6$ alkylsulfonylamino group, an aryl $C_1$–$C_6$ alkylamino group, an N-(aryl $C_1$–$C_6$ alkyl)-N-(aroyl)amino group, an arylsulfonylamino group, an aryl $C_1$–$C_6$ alkylsulfonylamino group or a $C_4$–$C_7$ cyclic imino group, and $R^{2c}$ is a hydroxyl group, an amino group, a $C_1$–$C_6$ alkoxy group, a mono- or di-$C_1$–$C_6$ alkylamino group, a $C_1$–$C_6$ alkylsulfonylamino group or an arylsulfonylamino or an aryl $C_1$–$C_6$ alkylsulfonylamino group which may have a $C_1$–$C_6$ alkyl group, which comprises reacting a compound represented by formula [XII]:

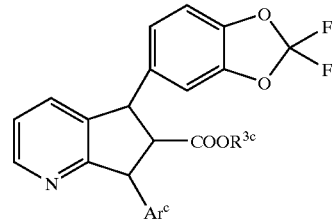

[XII]

wherein $R^{3c}$ is a $C_1$–$C_6$ alkyl group, and $Ar^c$ is the same as defined above, with an oxidizing agent to obtain a compound represented by formula [XIII]:

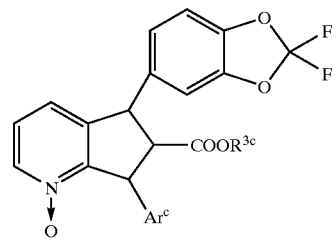

[XIII]

wherein $Ar^c$ and $R^{3c}$ are the same as defined above, then reacting the compound represented by formula [XIII] with a compound represented by formula [XIV]:

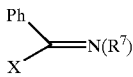

wherein $R^7$ is a $C_1$–$C_6$ alkyl group, a $C_1$–$C_6$ cycloalkyl group or an aryl $C_1$–$C_6$ alkyl group, and X is a halogen atom, to obtain a compound represented by formula [XV]:

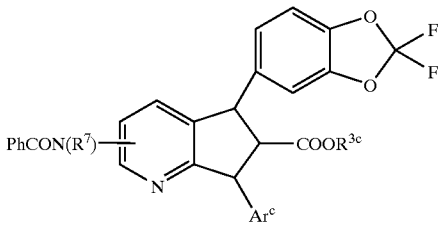

wherein $Ar^c$, $R^{3c}$ and $R^7$ are the same as defined above, then if necessary, subjecting the compound represented by formula [XV] to debenzoylation and/or dearyl $C_1$–$C_6$ alkylation, to obtain a compound represented by formula [XVI]:

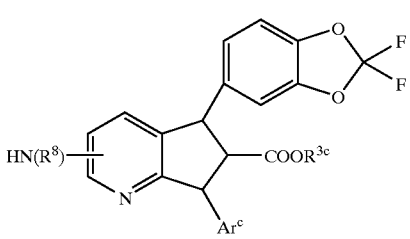

wherein $R^8$ is a hydrogen atom or an amino-protecting group, a $C_1$–$C_6$ alkyl group, a $C_1$–$C_6$ cycloalkyl group or an aryl $C_1$–$C_6$ alkyl group, and $Ar^c$ and $R^{3c}$ are the same as defined above, then if necessary, subjecting the compound represented by formula [XVI] to one or two reactions in appropriate combination selected from the group consisting of $C_1$–$C_6$ alkylation, $C_3$–$C_8$ cycloalkylation, $C_3$–$C_8$ cycloalkyl $C_1$–$C_6$ alkylation, $C_2$–$C_6$ alkanoylation, aroylation, sulfonylation, $C_1$–$C_6$ alkylsulfonylation, aryl $C_1$–$C_6$ alkylation, arylsulfonylation, aryl $C_1$–$C_6$ alkylsulfonylation and $C_4$–$C_7$ cyclic imination, and if necessary, subjecting the resulting compound to desired synthetically equivalent conversion of a functional group and/or removal of a protecting group, or conversion into a pharmaceutically acceptable salt thereof.

11. A composition comprising a compound represented by formula [I] or a pharmaceutically acceptable salt thereof:

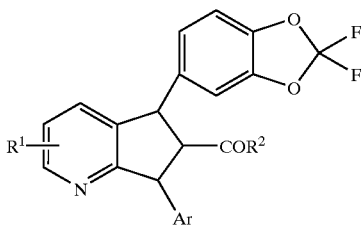

wherein Ar is a phenyl group, a thienyl group or a pyridyl group which may have one to three substituents selected from the group consisting of hydroxyl groups, amino groups, carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups, $R^1$ is a hydrogen atom, a hydroxyl group, a cyano group, a nitro group, a carboxyl group, an amino group, a halogen atom, a $C_1$–$C_6$ alkyl group, a $C_3$–$C_8$ cycloalkyl group, a $C_3$–$C_8$ cycloalkyl $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkylthio group, a formyl group, a $C_2$–$C_6$ alkanoyl group, an aroyl group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl)amino group, a $C_2$–$C_6$ alkanoylamino group, an aroylamino group, an N—($C_1$–$C_6$ alkyl)-N-(aroyl)amino group, a $C_1$–$C_6$ alkylsulfonylamino group, an aryl $C_1$–$C_6$ alkylamino group, an N-(aryl $C_1$–$C_6$ alkyl)-N-(aroyl)amino group, an arylsulfonylamino group, an aryl $C_1$–$C_6$ alkylsulfonylamino group, a $C_4$–$C_7$ cyclic imino group or a $C_1$–$C_6$ alkoxycarbonyl group, and $R^2$ is a hydroxyl group, an amino group, a $C_1$–$C_6$ alkoxy group, a mono- or di-$C_1$–$C_6$ alkylamino group, a $C_1$–$C_6$ alkylsulfonylamino group or an arylsulfonylamino or an aryl $C_1$–$C_6$ alkylsulfonylamino group which may have a $C_1$–$C_6$ alkyl group, as an active ingredient, and a pharmaceutically suitable carrier substance.

12. The composition according to claim 11, which is an agent for treatment of at least one disorder selected from the group consisting of hypertension, pulmonary hypertension, Raynaud's disease, acute renal failure, heart failure, myocardial infarction, angina pectoris, cerebral infarction, cerebral vasospasm, arteriosclerosis, asthma, gastric ulcer, diabetes, restenosis, prostatism, endotoxin shock, endotoxin-induced multiple organ failure and disseminated intravascular coagulation and cyclosporin-induced renal failure and hypertension.

13. The method according to claim 8, wherein said reacting a compound represented by formula [II] with an organic metal compound represented by formula [III], comprises reacting a compound of formula [II] with 1 to 4 equivalents of a compound of formula [III] in a solvent at a temperature ranging from –100° C. to room temperature for 0.5 to 4 hours.

14. The method according to claim 13, wherein the solvent is THF, $Et_2O$ or dimethoxyethane.

15. The method according to claim 8, wherein said reducing the compound represented by formula [IV], comprises treating said compound with 20 to 100 wt % of an appropriate hydrogenation catalyst in the presence of an acid under an atmosphere of hydrogen at a pressure of ranging from atmospheric pressure to 5 kg/cm² at a temperature ranging from room temperature to 50° C.

16. The method according to claim 15, wherein said acid is selected from the group consisting of acetic acid, sulfuric acid and perchloric acid.

17. The method according to claim 8, wherein said reducing the compound represented by formula [IV], comprises treating said compound with 5 to 15 equivalents of a mineral acid in a solvent mixture of an ethereal solvent and an alcoholic solvent in the presence of 5 to 15 equivalents of a metal at a temperature of ranging from –78° C. to room temperature.

18. The method according to claim 17, wherein said mineral acid is acetic acid or hydrochloric acid.

19. The method according to claim 17, wherein said ethereal solvent is THF, $Et_2O$ or dioxane.

20. The method according to claim 17, wherein said alcoholic solvent is selected from the group consisting of methanol, ethanol and tert-butanol.

21. The method according to claim 17, wherein said metal is zinc powder or iron powder.

22. The method according to claim 8, wherein said conversion of a functional group, comprises a method selected from the group consisting of reduction, oxidation, and $C_1$–$C_6$ alkylation.

23. The method according to claim 8, wherein said removal of a protecting group comprises a method selected from the group consisting of solvolysis, chemical reduction, and hydrogenation.

24. The method according to claim 9, wherein said reacting a compound represented by formula [VI] with an organic metal compound represented by formula [III], comprises reacting a compound of formula [VI] with 1 to 4 equivalents of a compound of formula [III] in a solvent at a temperature ranging from −100° C. to room temperature for 0.5 to 4 hours.

25. The method according to claim 24, wherein the solvent is THF, $Et_2O$ or dimethoxyethane.

26. The method according to claim 9, wherein said reacting a compound represented by formula [IX] with a compound represented by formula [X], comprises reacting a compound of formula [IX] with 1 to 5 equivalents of a compound of general formula [X] in an inert solvent at a temperature ranging from −100° C. to room temperature for 0.5 to 5 hours.

27. The method according to claim 26, wherein said inert solvent is THF or $Et_2O$.

28. The method according to claim 9, wherein said reducing the compound represented by formula [X], comprises treating said compound with 20 to 100 wt % of an appropriate hydrogenation catalyst in the presence of an acid under an atmosphere of hydrogen at a pressure of ranging from atmospheric pressure to 5 kg/cm² at a temperature ranging from room temperature to 50° C.

29. The method according to claim 28, wherein said acid is selected from the group consisting of acetic acid, sulfuric acid and perchloric acid.

30. The method according to claim 9, wherein said reducing the compound represented by formula [X], comprises treating said compound with 5 to 15 equivalents of a mineral acid in a solvent mixture of an ethereal solvent and an alcoholic solvent in the presence of 5 to 15 equivalents of a metal at a temperature of ranging from −78° C. to room temperature.

31. The method according to claim 30, wherein said mineral acid is acetic acid or hydrochloric acid.

32. The method according to claim 30, wherein said ethereal solvent is THF, $Et_2O$ or dioxane.

33. The method according to claim 30, wherein said alcoholic solvent is selected from the group consisting of methanol, ethanol and tert-butanol.

34. The method according to claim 30, wherein said metal is zinc powder or iron powder.

35. The method according to claim 9, wherein said conversion of a functional group, comprises a method selected from the group consisting of reduction, oxidation, and $C_1$–$C_6$ alkylation.

36. The method according to claim 9, wherein said removal of a protecting group comprises a method selected from the group consisting of solvolysis, chemical reduction, and hydrogenation.

37. The method according to claim 10, wherein said reacting a compound represented by formula [XII] with an oxidizing agent, comprises reacting a compound of formula [XII] with 1 to 3 equivalents of an oxidizing agent in a solvent at a temperature ranging from −40° C. to room temperature.

38. The method according to claim 37, wherein said oxidizing agent is metachloroperbenzoic acid or sodium periodate.

39. The method according to claim 37, wherein said solvent is methylene chloride or chloroform.

40. The method according to claim 10, wherein said reacting the compound represented by formula [XIII] with a compound represented by formula [XIV], comprises reacting a compound of formula [XIII] with 2 to 30 equivalents of a compound of formula [XIV] in a solvent at a temperature ranging from room temperature to the boiling point of the solvent.

41. The method according to claim 40, wherein said solvent is methylene chloride, chloroform or 1,2-dichloroethane.

42. The method according to claim 40, further comprising 10 to 50 equivalents of an inorganic base or an organic base.

43. The method according to claim 42, wherein said inorganic base is potassium hydrogencarbonate or cesium fluoride.

44. The method according to claim 42, wherein said organic base is triethylamine.

45. The method according to claim 10, wherein said conversion of a functional group, comprises a method selected from the group consisting of reduction, oxidation, and $C_1$–$C_6$ alkylation.

46. The method according to claim 10, wherein said removal of a protecting group comprises a method selected from the group consisting of solvolysis, chemical reduction, and hydrogenation.

47. The composition according to claim 12, wherein said disease is selected from the group consisting of heart failure, myocardial infarction, angina pectoris.

48. A method of inhibiting endothelin production in a patient in need thereof, comprising administering to said patient an effective dose to inhibit endothelin production of a compound represented by formula [I] or a pharmaceutically acceptable salt thereof:

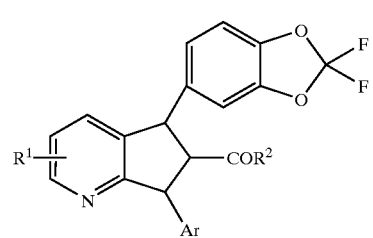

[I]

wherein Ar is a phenyl group, a thienyl group or a pyridyl group which may have one to three substituents selected from the group consisting of hydroxyl groups, amino groups, carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups, $R^1$ is a hydrogen atom, a hydroxyl group, a cyano group, a nitro group, a carboxyl group, an amino group, a halogen atom, a $C_1$–$C_6$ alkyl group, a $C_3$–$C_8$ cycloalkyl group, a $C_3$–$C_8$ cycloalkyl $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkylthio group, a formyl group, a $C_2$–$C_6$ alkanoyl group, an aroyl group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl)amino group, a $C_2$–$C_6$ alkanoylamino group, an aroylamino group, an N—($C_1$–$C_6$ alkyl)-N-(aroyl)amino group, a $C_1$–$C_6$ alkylsulfonylamino group, an aryl $C_1$–$C_6$ alkylamino group, an N-(aryl $C_1$–$C_6$ alkyl)-N-(aroyl)amino group, an arylsulfonylamino group, an aryl $C_1$–$C_6$ alkylsulfonylamino group, a $C_4$–$C_7$ cyclic imino group or a $C_1$–$C_6$ alkoxycarbonyl group, and $R^2$ is a hydroxyl group, an amino group, a $C_1$–$C_6$ alkoxy group, a mono- or di-$C_1$–$C_6$ alkylamino group, a $C_1$–$C_6$ alkylsulfonylamino group or an arylsulfonylamino or an aryl $C_1$–$C_6$ alkylsulfonylamino group which may have a $C_1$–$C_6$ alkyl group.

49. The method according to claim 48, wherein said compound is selected from the group consisting of (5S,6R,7R)-2-amino-carboxy-5-(2,2-difluoro-1,3-benzodioxol-5-yl)-7-[2-methylpropyl)-4-methoxyphenyl]cyclopenteno[1,2,b]pyridine, (5S,6R,7R)-6-carboxy-5-(2,2-difluoro-1,3-benzodioxol-5-yl)-7-(2-propyl-4-methoxyphenyl)-2-(methanesulfonylamino)cyclopenteno[1,2,b]pyridine, (5S,6R,7R)-6-carboxy-5-(2,2-difluoro-1,3-benzodioxol-5-yl)-7-[2-(3-hydroxy-2-methylpropyl)-4-methoxyphenyl]-2-(methanesulfonylamino)cyclopenteno[1,2,b]pyridine, (5S,6R,7R)-6-carboxy-5-(2,2-difluoro-1,3-benzodioxol-5-yl)-7-[2-(3-hydroxy-2-methylpropyl)-4-methoxyphenyl]-2-N-propylaminocyclopenteno[1,2,b]pyridine, (5S,6R,7R)-6-carboxy-5-(2,2-difluoro-1,3-benzodioxol-5-yl)-7-(2-propyl-4-methoxyphenyl)-2-N-isopropylaminocyclopenteno[1,2,b]pyridine, (5S,6R,7R)-6-carboxy-5-(2,2-difluoro-1,3-benzodioxol-5-yl)-7-(2-hydroxymethyl-4-methoxyphenyl)-2-N-isopropylaminocyclopenteno[1,2,b]pyridine, (5S,6R,7R)-6-carboxy-5-(2,2-difluoro-1,3-benzodioxol-5-yl)-7-[2-(1-hydroxyethyl)-4-methoxyphenyl]-2-N-isopropylaminocyclopenteno[1,2,b]pyridine, (5S,6R,7R)-6-carboxy-5-(2,2-difluoro-1,3-benzodioxol-5-yl)-7-[2-(2-hydroxy-2-methylpropyl)-4-methoxyphenyl]-2-N-isopropylaminocyclopenteno[1,2,b]pyridine, (5S,6R,7R)-6-carboxy-5-(2,2-difluoro-1,3-benzodioxol-5-yl)-7-[2-(3-hydroxy-2-methylpropyl)-4-methoxyphenyl]-2-N-isopropylaminocyclopenteno[1,2,b]pyridine, (5S,6R,7R)-6-carboxy-5-(2,2-difluoro-1,3-benzodioxol-5-yl)-7-[2-(3-hydroxy-2-methylpropoxy)-4-methoxyphenyl]-2-N-isopropylaminocyclopenteno[1,2,b]pyridine, (5S,6R,7R)-6-carboxy-7-[2-(1-carboxyethyl)-4-methoxyphenyl]-5-(2,2-difluoro-1,3-benzodioxol-5-yl)-2-N-isopropylaminocyclopenteno[1,2,b]pyridine, (5S,6R,7R)-6-carboxy-7-[2-(1-carboxybutyl)-4-methoxyphenyl]-5-(2,2-difluoro-1,3-benzodioxol-5-yl)-2-N-isopropylaminocyclopenteno[1,2,b]pyridine, (5S,6R,7R)-6-carboxy-7-[2-(2-carboxypropyl)-4-methoxyphenyl]-5-(2,2-difluoro-1,3-benzodioxol-5-yl)-2-N-isopropylaminocyclopenteno[1,2,b]pyridine, (5S,6R,7R)-6-carboxy-5-(2,2-difluoro-1,3-benzodioxol-5-yl)-7-[2-(1-carbamoylethyl)-4-methoxyphenyl]-2-N-isopropylaminocyclopenteno[1,2,b]pyridine, (5S,6R,7R)-6-carboxy-5-(2,2-difluoro-1,3-benzodioxol-5-yl)-7-{2-[1-(N-methylaminocarbonyl)ethyl]-4-methoxyphenyl}-2-N-isopropylaminocyclopenteno[1,2,b]pyridine, (5S,6R,7R)-6-carboxy-5-(2,2-difluoro-1,3-benzodioxol-5-yl)-7-{2-[1-(N,N-dimethylaminocarbonyl)ethyl]-4-methoxyphenyl}-2-N-isopropylaminocyclopenteno[1,2,b]pyridine, (5S,6R,7R)-6-carboxy-5-(2,2-difluoro-1,3-benzodioxol-5-yl)-7-[2-(3-hydroxy-2-methylpropoxy)phenyl]-2-N-isopropylaminocyclopenteno[1,2,b]pyridine, (5S,6R,7R)-6-carboxy-5-(2,2-difluoro-1,3-benzodioxol-5-yl)-7-[2-(3-hydroxy-2-methylpropoxy)-4-fluorophenyl]-2-N-isopropylaminocyclopenteno[1,2,b]pyridine, (5S,6R,7R)-6-carboxy-5-(2,2-difluoro-1,3-benzodioxol-5-yl)-7-(2-hydroxymethyl-4-methoxyphenyl)-2-N-butylaminocyclopenteno[1,2,b]pyridine, (5S,6R,7R)-6-carboxy-5-(2,2-difluoro-1,3-benzodioxol-5-yl)-7-[2-(3-hydroxy-2-methylpropyl)-4-methoxyphenyl]-2-N-butylaminocyclopenteno[1,2,b]pyridine, (5S,6R,7R)-6-carboxy-5-(2,2-difluoro-1,3-benzodioxol-5-yl)-7-[2-(3-hydroxy-2-methylpropoxy)-4-methoxyphenyl]-2-N-butylaminocyclopenteno[1,2,b]pyridine, (5S,6R,7R)-6-carboxy-7-[2-(1-carboxyethyl)-4-methoxyphenyl]-5-(2,2-difluoro-1,3-benzodioxol-5-yl)-2-propylaminocyclopenteno[1,2,b]pyridine, (5S,6R,7R)-6-carboxy-7-[2-(1-carboxyethyl)-4-methoxyphenyl]-5-(2,2-difluoro-1,3-benzodioxol-5-yl)-2-butylcyclopenteno[1,2,b]pyridine, (5S,6R,7R)-6-carboxy-7-[2-(1-carboxybutyl)-4-methoxyphenyl]-5-(2,2-difluoro-1,3-benzodioxol-5-yl)-2-butylcyclopenteno[1,2,b]pyridine, (5S,6R,7R)-6-carboxy-5-(2,2-difluoro-1,3-benzodioxol-5-yl)-7-{2-[1-(N,N-dimethylaminocarbonyl)ethyl]-4-methoxyphenyl}-2-butylcyclopenteno[1,2,b]pyridine and (5S,6R,7R)-5-(2,2-difluoro-1,3-benzodioxol-5-yl)-7-{2-[1(N,N-dimethylaminocarbonyl)ethyl]-4-methoxyphenyl}-2-N-isopropylamino-6-methanesulfonylaminocarbonylcyclopenteno[1,2,b]pyridine, or a pharmaceutically acceptable salt thereof.

50. The method according to claim 48, wherein said compound is selected from the group consisting of (5S,6R,7R)-6-carboxy-5(2,2-difluoro-1,3-benzodioxol-5-yl)-7-(2-propyl-4-methoxyphenyl)-2-(methanesulfonylamino)cyclopenteno[1,2,b]pyridine, (5S,6R,7R)-6-carboxy-5-(2,2-difluoro-1,3-benzodioxol-5-yl)-7-[2-(3-hydroxy-2-methylpropyl)-4-methoxyphenyl]-2-N-isopropylaminocyclopenteno[1,2,b]pyridine, (5S,6R,7R)-6-carboxy-7-[2-(1-carboxyethyl)-4-methoxyphenyl]-5-(2,2-difluoro-1,3-benzodioxol-5-yl)-2-N-isopropylaminocyclopenteno[1,2,b]pyridine, (5S,6R,7R)-6-carboxy-7-[2-(1-carboxybutyl)-4-methoxyphenyl]-5-(2,2-difluoro-1,3-benzodioxol-5-yl)-2-N-isopropylaminocyclopenteno[1,2,b]pyridine, (5S,6R,7R)-6-carboxy-5-(2,2-difluoro-1,3-benzodioxol-5-yl)-7-{2-[1-(N,N-dimethylaminocarbonyl)ethyl]-4-methoxyphenyl)-2-N-isopropylaminocyclopenteno[1,2,b]pyridine, (5S,6R,7R)-6-carboxy-5-(2,2-difluoro-1,3-benzodioxol-5-yl)-7-[2-(3-hydroxy-2-methylpropyl)phenyl]-2-N-isopropylaminocyclopenteno[1,2,b]pyridine, (5S,6R,7R)-6-carboxy-7-[2-(1-carboxyethyl)-4-methoxyphenyl]-5-(2,2-difluoro-1,3-benzodioxol-5-yl)-2-propylcyclopenteno[1,2,b]pyridine and (5S,6R,7R)-6-carboxy-7-[2-(1-carboxyethyl)-4-methoxyphenyl]-5-(2,2-difluoro-1,3-benzodioxol-5-yl)-2-butylcyclopenteno[1,2,b]pyridine, or a pharmaceutically acceptable salt thereof.

51. The method according to claim 48, wherein said compound is (5S,6R,7R)-6-carboxy-5(2,2-difluoro-1,3-benzodioxol-5-yl)-7-[2-(3-hydroxy-2-methylpropyl)-4-methoxyphenyl]-2-N-isopropylaminocyclopenteno[1,2,b]pyridine or a pharmaceutically acceptable salt thereof.

52. The method according to claim 48, wherein said compound is (5S,6R,7R)-6-carboxy-5(2,2-difluoro-1,3-benzodioxol-5-yl)-7-[2-(3-hydroxy-2-methylpropyl)-4-methoxyphenyl]-2-N-isopropylaminocyclopenteno[1,2,b]pyridine or a pharmaceutically acceptable salt thereof, wherein said inhibiting endothelin production treats a disease selected from the group consisting of heart failure, myocardial infarction, angina pectoris.

53. The method according to claim 48, wherein said compound is (5S,6R,7R)-6-carboxy-5(2,2-difluoro-1,3- benzodioxol-5-yl)-7-[2-(2-carboxypropyl)-4-methoxyphenyl]-2-isopropylaminocyclopenteno[1,2,b]pyridine or a pharmaceutically acceptable salt thereof.

54. The method according to claim 48, wherein said compound is (5S,6R,7R)-6-carboxy-5(2,2-difluoro-1,3-benzodioxol-5-yl)-7-[2-(2-carboxypropyl)4-methoxyphenyl]-2-isopropylaminocyclopenteno[1,2,b]pyridine or a pharmaceutically acceptable salt thereof, wherein said inhibiting endothelin production treats a disease selected from the group consisting of heart failure, myocardial infarction, angina pectoris.

55. The method according to claim 48, wherein said administering to said patient an effective dose comprises oral administration or parenteral administration.

56. The method according to claim 55, wherein said effective dose by said oral administration ranges from 0.1 to 100 mg/kg body weight/day.

57. The method according to claim 55, wherein said effective dose by said parenteral administration ranges from 0.01 to 10 mg/kg body weight/day.

58. The method according to claim 48, wherein said inhibiting endothelin production treats a disease selected from the group consisting of hypertension, pulmonary hypertension, Raynaud's disease, acute renal failure, heart failure, myocardial infarction, angina pectoris, cerebral infarction, cerebral vasospasm, arteriosclerosis, asthma, gastric ulcer, diabetes, restenosis, prostatism, endotoxin shock, endotoxin-induced multiple organ failure and disseminated intravascular coagulation and cyclosporin-induced renal failure and hypertension.

59. The method according to claim 48, wherein said inhibiting endothelin production treats a disease selected from the group consisting of heart failure, myocardial infarction, angina pectoris.

60. A method of treating a disease selected from the group consisting of hypertension, pulmonary hypertension, Raynaud's disease, acute renal failure, heart failure, myocardial infarction, angina pectoris, cerebral infarction, cerebral vasospasm, arteriosclerosis, asthma, gastric ulcer, diabetes, restenosis, prostatism, endotoxin shock, endotoxin-induced multiple organ failure and disseminated intravascular coagulation and cyclosporin-induced renal failure and hypertension, comprising administering to a patient in need thereof an effective dose to treat said disease of a compound represented by formula [I] or a pharmaceutically acceptable salt thereof:

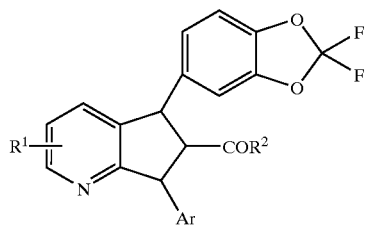

[I]

wherein Ar is a phenyl group, a thienyl group or a pyridyl group which may have one to three substituents selected from the group consisting of hydroxyl groups, amino groups, carboxyl groups, carbamoyl groups, halogen atoms, $C_1$–$C_6$ alkyl groups, $C_2$–$C_6$ alkenyl groups, $C_2$–$C_6$ alkynyl groups, $C_1$–$C_6$ alkoxy groups, $C_1$–$C_6$ alkoxycarbonyl groups, mono- and di-$C_1$–$C_6$ alkylamino groups and mono- and di-$C_1$–$C_6$ alkylaminocarbonyl groups, $R^1$ is a hydrogen atom, a hydroxyl group, a cyano group, a nitro group, a carboxyl group, an amino group, a halogen atom, a $C_1$–$C_6$ alkyl group, a $C_3$–$C_8$ cycloalkyl group, a $C_3$–$C_8$ cycloalkyl $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkylthio group, a formyl group, a $C_2$–$C_6$ alkanoyl group, an aroyl group, a mono- or di-$C_1$–$C_6$ alkylamino group, a $C_3$–$C_8$ cycloalkylamino group, a $C_3$–$C_8$ cycloalkyl $C_1$–$C_6$ alkylamino group, an N—($C_1$–$C_6$ alkyl)-N—($C_3$–$C_8$ cycloalkyl)amino group, a $C_2$–$C_6$ alkanoylamino group, an aroylamino group, an N—($C_1$–$C_6$ alkyl)-N-(aroyl)amino group, a $C_1$–$C_6$ alkylsulfonylamino group, an aryl $C_1$–$C_6$ alkylamino group, an N-(aryl $C_1$–$C_6$ alkyl)-N-(aroyl)amino group, an arylsulfonylamino group, an aryl $C_1$–$C_6$ alkylsulfonylamino group, a $C_4$–$C_7$ cyclic imino group or a $C_1$–$C_6$ alkoxycarbonyl group, and $R^2$ is a hydroxyl group, an amino group, a $C_1$–$C_6$ alkoxy group, a mono- or di-$C_1$–$C_6$ alkylamino group, a $C_1$–$C_6$ alkylsulfonylamino group or an arylsulfonylamino or an aryl $C_1$–$C_6$ alkylsulfonylamino group which may have a $C_1$–$C_6$ alkyl group.

61. The method according to claim 60, wherein said disease is selected from the group consisting of heart failure, myocardial infarction, and angina pectoris.

62. The method according to claim 60, wherein said compound is selected from the group consisting of wherein said compound is selected from the group consisting of (5S,6R,7R)-2-amino-carboxy-5-(2,2-difluoro-1,3-benzodioxol-5-yl)-7-[2-(3-hydroxy-2-methylpropyl)-4-methoxyphenyl]cyclopenteno[1,2,b]pyridine, (5S,6R,7R)-6-carboxy-5-(2,2-difluoro-1,3-benzodioxol-5-yl)-7-(2-propyl-4-methoxyphenyl)-2-(methanesulfonylamino)cyclopenteno[1,2,b]pyridine, (5S,6R,7R)-6-carboxy-5-(2,2-difluoro-1,3-benzodioxol-5-yl)-7-[2-(3-hydroxy-2-methylpropyl)-4-methoxyphenyl]-2-(methanesulfonylamino)cyclopenteno[1,2,b]pyridine, (5S,6R,7R)-6-carboxy-5-(2,2-difluoro-1,3-benzodioxol-5-yl)-7-[2-(3-hydroxy-2-methylpropyl)-4-methoxyphenyl]-2-N-propylaminocyclopenteno[1,2,b]pyridine, (5S,6R,7R)-6-carboxy-5-(2,2-difluoro-1,3-benzodioxol-5-yl)-7-(2-propyl-4-methoxyphenyl)-2-N-isopropylaminocyclopenteno[1,2,b]pyridine, (5S,6R,7R)-6-carboxy-5-(2,2-difluoro-1,3-benzodioxol-5-yl)-7-(2-hydroxymethyl-4-methoxyphenyl)-2-N-isopropylaminocyclopenteno[1,2,b]pyridine, (5S,6R,7R)-6-carboxy-5-(2,2-difluoro-1,3-benzodioxol-5-yl)-7-[2-(1-hydroxyethyl)-4-methoxyphenyl]3-2-N-isopropylaminocyclopenteno[1,2,b]pyridine, (5S,6R,7R)-6-carboxy-5-(2,2-difluoro-1,3-benzodioxol-5-yl)-7-[2-(2-hydroxy-2-methylpropyl)-4-methoxyphenyl]-2-N-isopropylaminocyclopenteno[1,2,b]pyridine, (5S,6R,7R)-6-carboxy-5-(2,2-difluoro-1,3-benzodioxol-5-yl)-7-[2-(3-hydroxy-2-methylpropyl)-4-methoxyphenyl]-2-N-isopropylaminocyclopenteno[1,2,b]pyridine, (5S,6R,7R)-6-carboxy-5-(2,2-difluoro-1,3-benzodioxol-5-yl)-7-[2-(3-hydroxy-2-methylpropoxy)-4-methoxyphenyl]-2-N-isopropylaminocyclopenteno[1,2,b]pyridine, (5S,6R,7R)-6-carboxy-7-[2-(1-carboxyethyl)-4-methoxyphenyl]-5-(2,2-difluoro-1,3-benzodioxol-5-yl)-2-N-isopropylaminocyclopenteno[1,2,b]pyridine, (5S,6R,7R)-6-carboxy-7-[2-(1-carboxybutyl)-4-methoxyphenyl]-5-(2,2-difluoro-1,3-benzodioxol-5-yl)-2-N-isopropylaminocyclopenteno[1,2,b]pyridine, (5S,6R,7R)-6-carboxy-7-[2-(2-carboxypropyl)-4-methoxyphenyl]-5-(2,2-difluoro-1,3-benzodioxol-5-yl)-2-N-isopropylaminocyclopenteno[1,2,b]pyridine, (5S,6R,7R)-6-carboxy-5-(2,2-difluoro-1,3-benzodioxol-5-yl)-7-[2-(1-carbamoylethyl)-4-methoxyphenyl]-2-N-isopropylaminocyclopenteno[1,2,b]pyridine, (5S,6R,7R)-6-carboxy-5-(2,2-difluoro-1,3-benzodioxol-5-yl)-7-{2-[1-(N-methylaminocarbonyl)ethyl]-4-methoxyphenyl}-2-N- isopropylaminocyclopenteno[1,2,b]pyridine, (5S,6R,7R)-6-carboxy-5-(2,2-difluoro-1,3-benzodioxol-5-yl)-7-{2-[1-(N,N-dimethylaminocarbonyl)ethyl]-4-methoxyphenyl}-2-N-isopropylaminocyclopenteno[1,2,b]pyridine, (5S,6R,7R)-6-carboxy-5-(2,2-difluoro-1,3-benzodioxol-5-yl)-7-[2-(3-hydroxy-2-methylpropoxy)phenyl]-2-N-isopropylaminocyclopenteno[1,2,b]pyridine, (5S,6R,7R)-6-carboxy-5-(2,2-difluoro-1,3-benzodioxol-5-yl)-7-[2-(3-hydroxy-2-methylpropoxy)-4-fluorophenyl]-2-N-isopropylaminocyclopenteno[1,2,b]pyridine, (5S,6R,7R)-6-carboxy-5-(2,2-difluoro-1,3-benzodioxol-5-yl)-7-(2-hydroxymethyl-4-methoxyphenyl)-2-N-butylaminocyclopenteno[1,2,b]pyridine, (5S,6R,7R)-6-carboxy-5-(2,2-difluoro-1,3-benzodioxol-5-yl)-7-[2-(3-hydroxy-2-methylpropyl)-4-methoxyphenyl]-2-N-butylaminocyclopenteno[1,2,b]pyridine, (5S,6R,7R)-6-carboxy-5-(2,2-difluoro-1,3-benzodioxol-5-yl)-7-[2-(3-hydroxy-2-methylpropoxy)-4-methoxyphenyl]-2-N-butylaminocyclopenteno[1,2,b]pyridine, (5S,6R,7R)-6-carboxy-7-[2-(1-carboxyethyl)4-methoxyphenyl]-5-(2,2-difluoro-1,3-benzodioxol-5-yl)-2-propylaminocyclopenteno[1,2,b]pyridine, (5S,6R,7R)-6-carboxy-7-[2-(1-carboxyethyl)4-methoxyphenyl]-5-(2,2-difluoro-1,3-benzodioxol-5-yl)-2-butylcyclopenteno[1,2,b]pyridine, (5S,6R,7R)-6-carboxy-7-[2-(1-carboxybutyl)-4-methoxyphenyl]-5-(2,2-difluoro-1,3-benzodioxol-5-yl)-2-butylcyclopenteno[1,2,b]pyridine, (5S,6R,7R)-6-carboxy-5-(2,2-difluoro-1,3-benzodioxol-5-yl)-7-{2-[1-(N,N-dimethylaminocarbonyl)ethyl]-4-methoxyphenyl}-2-butylcyclopenteno[1,2,b]pyridine and (5S,6R,7R)-5-(2,2-difluoro-1,3-benzodioxol-5-yl)-7-{2-[1(N,N-dimethylaminocarbonyl)ethyl]-4-methoxypheny)}-2-N-isopropylamino-6-methanesulfonylaminocarbonylcyclopenteno[1,2,b]pyridine, or a pharmaceutically acceptable salt thereof.

63. The method according to claim 60, wherein said compound is selected from the group consisting of (5S,6R,7R)-6-carboxy-5(2,2-difluoro-1,3-benzodioxol-5-yl)-7-(2-propyl-4-methoxyphenyl)-2-(methanesulfonylamino)cyclopenteno[1,2,b]pyridine, (5S,6R,7R)-6-carboxy-5-(2,2-difluoro-1,3-benzodioxol-5-yl)-7-[2-(3-hydroxy-2-methylpropyl)-4-methoxyphenyl]-2-N-isopropylaminocyclopenteno[1,2,b]pyridine, (5S,6R,7R)-6-carboxy-7-[2-(1-carboxyethyl)-4-methoxyphenyl]-5-(2,2-difluoro-1,3-benzodioxol-5-yl)-2-N-isopropylaminocyclopenteno[1,2,b]pyridine, (5S,6R,7R)-6-carboxy-7-[2-(1-carboxybutyl)4-methoxyphenyl]-5-(2,2-difluoro-1,3-benzodioxol-5-yl)-2-N-isopropylaminocyclopenteno[1,2,b]pyridine, (5S,6R,7R)-6-carboxy-5-(2,2-difluoro-1,3-benzodioxol-5-yl)-7-{2-[1-(N,N-dimethylaminocarbonyl)ethyl]-4-methoxyphenyl)-2-N-isopropylaminocyclopenteno[1,2,b]pyridine, (5S,6R,7R)-6-carboxy-5-(2,2-difluoro-1,3-benzodioxol-5-yl)-7-[2-(3-hydroxy-2-methylpropyl)phenyl]-2-N-isopropylaminocyclopenteno[1,2,b]pyridine, (5S,6R,7R)-6-carboxy-7-[2-(1-carboxyethyl)-4-methoxyphenyl]-5-(2,2-difluoro-1,3-benzodioxol-5-yl)-2-propylcyclopenteno[1,2,b]pyridine and (5S,6R,7R)-6-carboxy-7-[2-(1-carboxyethyl)-4-methoxyphenyl]-5-(2,2-difluoro-1,3-benzodioxol-5-yl)-2-butylcyclopenteno[1,2,b]pyridine, or a pharmaceutically acceptable salt thereof.

64. The method according to claim 60, wherein said compound is (5S,6R,7R)-6-carboxy-5(2,2-difluoro-1,3-benzodioxol-5-yl)-7-[2-(3-hydroxy-2-methylpropyl)-4-methoxyphenyl]-2-N-isopropylaminocyclopenteno[1,2,b]pyridine or a pharmaceutically acceptable salt thereof.

65. The method according to claim 60, wherein said compound is (5S,6R,7R)-6-carboxy-5(2,2-difluoro-1,3-benzodioxol-5-yl)-7-[2-(3-hydroxy-2-methylpropyl)-4-methoxyphenyl]-2-N-isopropylaminocyclopenteno[1,2,b]pyridine or a pharmaceutically acceptable salt thereof, wherein said inhibiting endothelin production treats a disease selected from the group consisting of heart failure, myocardial infarction, angina pectoris.

66. The method according to claim 60, wherein said compound is (5S,6R,7R)-6-carboxy-5(2,2-difluoro-1,3-benzodioxol-5-yl)-7-[2-(2-carboxypropyl)-4-methoxyphenyl]-2-isopropylaminocyclopenteno[1,2,b]pyridine or a pharmaceutically acceptable salt thereof.

67. The method according to claim 60, wherein said compound is (5S,6R,7R)-6-carboxy-5(2,2-difluoro-1,3-benzodioxol-5-yl)-7-[2-(2-carboxypropyl)-4-methoxyphenyl]-2-isopropylaminocyclopenteno[1,2,b]pyridine or a pharmaceutically acceptable salt thereof, wherein said inhibiting endothelin production treats a disease selected from the group consisting of heart failure, myocardial infarction, angina pectoris.

68. The method according to claim 60, wherein said administering to said patient an effective dose comprises oral administration or parenteral administration.

69. The method according to claim 68, wherein said effective dose by said oral administration ranges from 0.1 to 100 mg/kg body weight/day.

70. The method according to claim 68, wherein said effective dose by said parenteral administration ranges from 0.01 to 10 mg/kg body weight/day.

\* \* \* \* \*